(12) United States Patent
Abou Shousha

(10) Patent No.: US 10,386,645 B2
(45) Date of Patent: Aug. 20, 2019

(54) DIGITAL THERAPEUTIC CORRECTIVE SPECTACLES

(71) Applicant: UNIVERSITY OF MIAMI, Miami, FL (US)

(72) Inventor: Mohamed Abou Shousha, Pembroke Pines, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 0 days.

(21) Appl. No.: 16/144,995

(22) Filed: Sep. 27, 2018

(65) Prior Publication Data

US 2019/0094552 A1 Mar. 28, 2019

Related U.S. Application Data

(60) Provisional application No. 62/563,770, filed on Sep. 27, 2017.

(51) Int. Cl.
| | | |
|---|---|---|
| *G02B 27/01* | (2006.01) | |
| *A61B 3/113* | (2006.01) | |
| *A61B 3/00* | (2006.01) | |

(52) U.S. Cl.
CPC ........ *G02B 27/0172* (2013.01); *A61B 3/0091* (2013.01); *A61B 3/113* (2013.01); *G02B 27/0179* (2013.01); *G02B 2027/014* (2013.01); *G02B 2027/0138* (2013.01); *G02B 2027/0141* (2013.01); *G02B 2027/0178* (2013.01); *G02B 2027/0187* (2013.01)

(58) Field of Classification Search
CPC ............ G02B 27/0172; G02B 27/0179; G02B 2027/0178; G02B 2027/014; G02B 2027/0138; G02B 2027/0141; G02B 2027/0187; A61B 3/0091; A61B 3/113
See application file for complete search history.

(56) References Cited

U.S. PATENT DOCUMENTS

| | | | |
|---|---|---|---|
| 5,359,675 | A | 10/1994 | Siwoff |
| 5,589,897 | A | 12/1996 | Sinclair et al. |
| 5,831,667 | A | 11/1998 | Siminou |
| 5,841,511 | A | 11/1998 | D'Souza et al. |
| 6,152,565 | A | 11/2000 | Liu et al. |
| 7,195,353 | B2 | 9/2007 | Blum et al. |
| 7,686,450 | B2 | 3/2010 | Heiberger |
| 8,135,227 | B2 | 3/2012 | Lewis et al. |

(Continued)

OTHER PUBLICATIONS

International Search Report and Written Opinion from International Application No. PCT/US18/52313 dated Nov. 20, 2018.

(Continued)

*Primary Examiner* — Maurice L. McDowell, Jr.
(74) *Attorney, Agent, or Firm* — Pillsbury Winthrop Shaw Pittman LLP

(57) ABSTRACT

Devices for testing, identifying, and compensating for ocular pathologies affecting the vision of a patient are provided in the form of digital therapeutic corrective spectacles that provided personalized, customized visual field corrected/enhancement. The devices include wearable spectacles with one or more digital monitors that are used to recreate an entire visual field as a digitized corrected image or that include custom-reality glasses that can be used to overlay a visual scene with generated image to correct or enhance the visual field of the subject.

30 Claims, 39 Drawing Sheets

(56) References Cited

U.S. PATENT DOCUMENTS

| | | |
|---|---|---|
| 8,494,298 B2 | 7/2013 | Lewis et al. |
| 9,516,283 B2 | 12/2016 | Hilkes et al. |
| 9,618,748 B2 | 4/2017 | Munger et al. |
| 9,952,434 B2 | 4/2018 | Jiao et al. |
| 9,955,862 B2 | 5/2018 | Freeman et al. |
| 10,058,454 B2 | 8/2018 | Chayet et al. |
| 10,111,583 B1 | 10/2018 | Freeman et al. |
| 10,127,706 B2 | 11/2018 | Jones et al. |
| 10,129,520 B2 | 11/2018 | Munger et al. |
| 2003/0174284 A1 | 9/2003 | Stewart |
| 2009/0153796 A1 | 6/2009 | Rabner |
| 2010/0149073 A1 | 6/2010 | Chaum et al. |
| 2012/0200595 A1 | 8/2012 | Lewis et al. |
| 2013/0169929 A1 | 7/2013 | Fateh |
| 2013/0215147 A1 | 8/2013 | Hilkes et al. |
| 2013/0329190 A1 | 12/2013 | Lewis et al. |
| 2014/0003762 A1 | 1/2014 | Macnamara |
| 2014/0132629 A1 | 5/2014 | Pandey et al. |
| 2014/0198017 A1 | 7/2014 | Lamb et al. |
| 2014/0210970 A1 | 7/2014 | Dalal et al. |
| 2015/0193984 A1 | 7/2015 | Bar-Zeev et al. |
| 2015/0277121 A1 | 10/2015 | Fridental |
| 2015/0355481 A1 | 12/2015 | Hilkes et al. |
| 2016/0104453 A1 | 4/2016 | Borenstein et al. |
| 2016/0262608 A1 | 9/2016 | Krueger |
| 2016/0270656 A1 | 9/2016 | Samec et al. |
| 2017/0000345 A1 | 1/2017 | Samec et al. |
| 2017/0001032 A1 | 1/2017 | Samec et al. |
| 2017/0007111 A1 | 1/2017 | Samec et al. |
| 2017/0007115 A1 | 1/2017 | Samec et al. |
| 2017/0007116 A1 | 1/2017 | Samec et al. |
| 2017/0010470 A1 | 1/2017 | Samec et al. |
| 2017/0017083 A1 | 1/2017 | Samec et al. |
| 2017/0092007 A1 | 3/2017 | Goldberg et al. |
| 2017/0273552 A1 | 9/2017 | Leung et al. |
| 2018/0012414 A1 | 1/2018 | Lewis et al. |
| 2018/0088323 A1 | 3/2018 | Bao et al. |
| 2018/0125716 A1 | 5/2018 | Cho et al. |

OTHER PUBLICATIONS

Notification of the International Search Report and the Written Opinion of the International Searching Authority, dated Nov. 20, 2018, in corresponding International Application No. PCT/2018/053213.

"Augmented-View for Restricted Visual Field: Multiple Device Implementations," by Vargas-Martin, et al., Optometry and Vision Science, Nov. 2002, vol. 79, No. 11, pp. 715-723. I I.

"Clinical Performance of Electronic, Head-mounted, Low-vision Devices," by Culharn, et al., Ophthalmic and Physiological Optics 2004, vol. 24, pp. 281-290. "Conformal and Other Image Warpings for Reading with Field Defect," by Juday, et al., SPiE vol. 2239 Visual Information Processing Iii (1994), pp. 92-102. I . . .1 —.

"Evaluation of a Prototype Minified Augmented-View Device for Patients with Impaired Night Vision," by Bowers, et al., Ophthalmic and Physiological Optics 2004, vol. 24, pp. 296-312.

"The Programmable Rernapper: Clinical Applications for Patients with Field Defects," by Loshin, et al., Optometry and Vision Science 1989, vol. 66., No. 6, pp. 389-395. 1 1.

Non-Final Office Action dated May 10, 2019 in related U.S. Appl. No. 16/367,687, 12 pages.

Non-Final Office Action dated May 16, 2019 in related U.S. Appl. No. 16/367,751, 13 pages.

Centroid of largest component

Any point between the centroid of largest component and the closet to the center Center of largest inscribed circle Any point between the center of the circle and the closet to the center Center of largest inscribed square Any point between the center of the square and the closet to the center

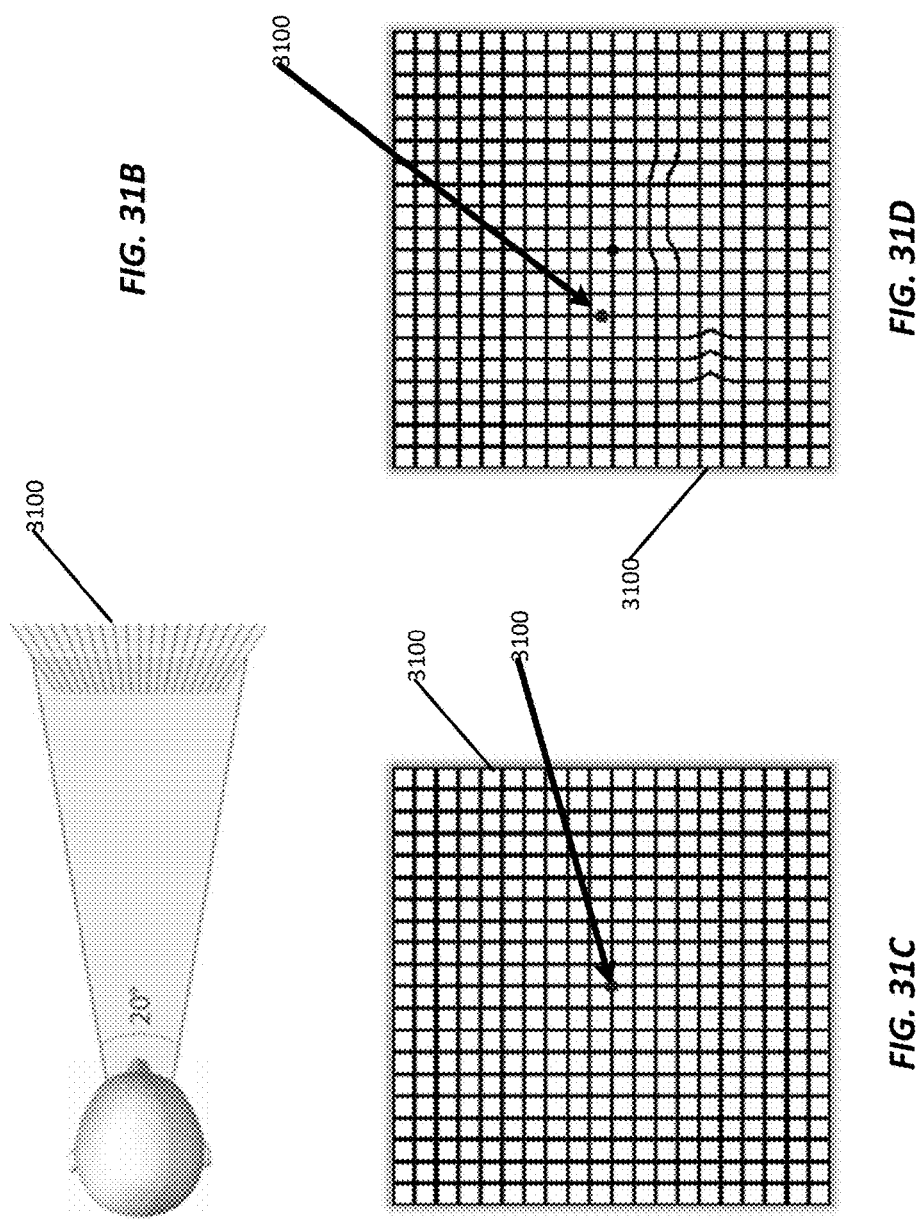

DIGITAL THERAPEUTIC CORRECTIVE SPECTACLES

CROSS-REFERENCE TO RELATED APPLICATIONS

The present application claims the benefit of U.S. Provisional Application No. 62/563,770, entitled "Digital Therapeutic Corrective Spectacles", filed on Sep. 27, 2017, which is hereby incorporated by reference herein in its entirety.

FIELD OF THE INVENTION

The present disclosure relates to techniques for compensating for visual impairments in the visual field, visual aberrations, and visual alignment errors of a user, and, more particularly, to wearable devices that correct for the aforementioned visual impairments and supplying corrections to the users.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Patients with ocular pathologies such as optic nerve pathologies and/or retinal pathologies (e.g., patients with glaucoma) have variable localized reduction in visual sensitivity of their visual field. That means that in some areas of their visual field the image is dimmer than other areas. This dimming within the visual field results because more intense illumination is required to stimulate the eye in the affected areas compared to unaffected areas, and is the result of the eye pathology. Patients will describe this dimming as having a cloud or blur over a part of their visual field. When the pathology progresses, the affected areas of the visual field can lose more and more of their ability to see and may eventually become totally blind.

Visual field diagnostic devices have been used to test the visual field sensitivity of a patient by projecting a light that is initially faint and then if the patient does not indicate that he/she is seeing it, the intensity increases more and more until the patient indicates that he/she sees the light. The sensitivity of the projected area is then recorded. If the patient does not see the light even with the maximum illumination intensity, then this area of the visual field is identified as blind.

Refractive errors negatively affect vision. Those refractive errors are caused by irregularities in the refractive elements of the eye. They result in blurry vision that is partly correctable by glass spectacles and contact lenses. That is the reason why some subjects see more than others and some have better quality of vision than others. Spectacles made out of glass as well as contact lenses only come in certain increments and would only correct regular errors of refraction e.g. regular astigmatism. Those regular errors of refraction are called lower order aberrations. Higher order aberrations are errors of refraction that are not correctable by spectacles or by contact lenses. Additionally, higher order aberrations are dynamic and not fixed. They change according to the pupil size, the accommodation state of the eye and direction of gaze.

Current techniques for treating presbyopia include single vision, bifocal and multifocal reading spectacles, and multifocal contact lenses. With the multifocal or bifocal spectacles, the patient will look through specific areas of the glass to get the required correction. With multifocal contact lenses, the light is diffracted into multiple focal points, improving the depth of focus but at the expense of decreasing the quality of vision. All those techniques are not very convenient and limit the near vision.

Double vision results from misalignment of the line of vision of patient. Double vision is dynamic and not static, meaning that it increases and decreases towards one or multiple gazes. So, if the subject has limitation in bringing the right eye outwards then the double vision will increase when the patient is looking to the right and might decrease when the subject is looking to the left.

Anisometropia (unequal refractive power of both eyes of a subject) is not uncommon, especially after eye surgery or trauma. It is one of the indications of cataract surgery per Medicare. Corrective glass spectacles are unable to correct for anisometropia. That is because the corrective glass spectacles produce two images, one to each eye, with unequal sizes (aniseikonia) and the brain could not fuse those two images into a binocular single vision. That problem is simply because the lenses of glass spectacles are either convex, magnify the image or concave, minify the image. The amount of magnification or minification depends on the amount of correction.

Lenses of glass spectacles are either convex, magnify the image or concave, minify the image. That affects the visual field of subjects. Glasses spectacles correct the refractive error of the patient but also produce distortion in the image being viewed.

Subjects with anisocoria have unequal pupil size and that can be congenital, acquired from an eye disease or following surgery or trauma. Those subjects have light sensitivity from a single eye and that eye cannot tolerate the light brightness tolerated by the healthy eye.

There is a need for an optical device that can compensate for the aforementioned visual impairments.

SUMMARY

In exemplary embodiments, the present techniques provide devices for testing, identifying, and/or compensating for one or more ocular pathologies affecting the vision of a patient. These ocular pathologies include, for example, pathologies of the optic nerve such as glaucoma, optic neuritis, and optic neuropathies, pathologies of the retina such as macular degeneration, retinitis pigmentosa, pathologies of the visual pathway as microvascular strokes and tumors and other conditions such as presbyopia, strabismus, high and low optical aberrations, monocular vision, anisometropia and aniseikonia, light sensitivity, anisocorian refractive errors, and astigmatism. In some exemplary embodiments, the present techniques provide devices for enhancing a field of view to a subject, such as modification of: a horizontal, vertical, and/or diagonal angle of view; light provided to one or more regions; size of objects in one or more regions; and/or location of objects in one or more regions.

In exemplary embodiments, the systems and devices described herein may include a wearable spectacles device configured to test, identify, compensate for visual impairments, and/or enhance aspects of a subjects vision or field of view. Some such embodiments may be configured to provide personalized customized visual correction to the subject using them. In one example, the spectacles device comprises digital therapeutic corrective spectacles (also termed herein "DTS"). Spectacles may also include, by way of example, glasses, sunglasses, and eyewear.

In an aspect a vision system may include a wearable spectacle device. The system may further include an image processing device having a processor and a memory. The image processing device may store instructions on the memory, wherein the instructions, when executed, cause the processor to execute a testing mode and/or a vision mode.

In one example, the system may further include a pupil tracking sensor configured to track a pupil physical condition and/or line of sight of a subject. In a further example, the pupil tracking sensor comprises one or more inward directed image sensors. In the above or another example, the system may include vision field sensor configured to capture a vision field in the vision mode.

In any of the above or another example, the instructions when executed by the processor may cause the processor to, in a testing mode, (i) instruct a display by the wearable spectacles device of a plurality of testing stimuli to the subject over one or more testing locations in a testing visual field, (ii) instruct the inward directed image sensor to capture position indications of the pupil physical condition and/or line of sight during the displaying of the plurality of testing stimuli over the one or more testing locations, and (iii) determine one or more affected regions in the testing visual field and determine one or more vision pathologies of the subject, wherein the plurality of stimuli differ in contrast levels with respect to each other and with respect to a baseline contrast level.

In any of the above or another example, the instructions when executed by the processor may cause the processor to, in the visioning mode, correct the image of the vision field to enhance a field of view and/or compensate for the one or more affected regions and instruct a display by the wearable spectacles device of the corrected image to the subject using the wearable spectacle device.

In any of the above or another example, the image processing device stores instructions that, when executed, cause the processor to: in the visioning mode, instruct the vision field camera to capture the image of the visual field, process the image in response to the determined one or more affected regions in the testing visual field, correct the image to compensate for the one or more affected regions, and instruct a display by the wearable spectacles device of the corrected image to the subject as a digital image.

In any of the above or another example, the digital spectacles may further comprise a first digital monitor and a second digital monitor each configured to display one of the plurality of stimuli to a respective eye of the subject in the testing mode. In any of the above or another example, the vision field camera comprises a first vision field camera and second vision field camera, the first vision field camera corresponding to the first digital monitor and the second vision field camera corresponding to the second digital monitor. In any of the above or another example, the pupil physical condition is selected from one or more of (i) pupil movement of one or more pupils, (ii) a limbus, (iii) a line of sight, and/or (iv) a visual axis of the subject. In any of the above or another example, the vision field camera comprises at least one vision field camera that extends inwardly from an outer surface of the wearable spectacle. In any of the above or another example, the vision field camera comprises at least one vision field camera that extends outwardly from an outer surface of the wearable spectacle. In any of the above or another example, in the visioning mode, the vision field camera captures continuous images of the visual field.

In any of the above or another example, the plurality of testing stimuli comprise at least one testing image of text or of an object. In any of the above or another example, the one or more affected regions comprises regions of reduced vision sensitivity or higher or lower optical aberrations. In any of the above or another example, the one or more affected regions comprises regions of reduced brightness. In any of the above or another example, the plurality of stimuli differ in contrast levels with respect to each other and with respect to a baseline contrast level by at least 20 dB. In any of the above or another example, the plurality of stimuli differ in contrast levels with respect to each other and with respect to a baseline contrast level by at least 30 dB. In any of the above or another example, the image processing device stores instructions that, when executed, cause the processor to: in the testing mode, instruct a display by the wearable spectacles device of the plurality of testing stimuli to the subject in a descending or ascending contrast.

In another aspect, a vision system includes a wearable spectacle device, at least one digital monitor, at least one vision field camera, and an image processing device.

In some examples, the at least one digital monitor is configured to display an image to an eye of the subject. In one example, the at least one vision field camera may be configured to capture a plurality of monocular images of a scene, each monocular image being shifted from each other monocular image. In one example, the image processing device may include a processor and a memory, and be coupled to the at least one digital monitor. The image processing device may store instructions on the memory that when executed, cause the processor to combine the plurality of monocular images into a combined image having a field of view greater than a field of view of any one of the plurality of monocular images. In any of the above or another embodiment, the instructions may cause the processor to display the combined image to the at least one digital monitor for presenting the subject with widened field view of the scene.

In any of the above or another example, the image processing device stores instructions on the memory that, when executed, cause the processor to: combine the plurality of monocular images into the combined image by performing selective field shifting on at least one of the plurality of monocular images relative to the other plurality of monocular images to generate a widen peripheral region for the combined image. In any of the above or another example, the image processing device stores instructions on the memory that, when executed, cause the processor to: combine the plurality of monocular images into the combined image by performing peripheral selective field manipulation on at least one of the plurality of monocular images relative to the other plurality of monocular images.

In any of the above or another example, the peripheral selective field manipulation comprises performing a shrinking or an enlarging on a peripheral region or a central macular region of the plurality of monocular images. In any of the above or another example, the image processing device stores instructions on the memory that, when executed, cause the processor to: combine the plurality of monocular images into the combined image by identifying a defect field region in at least one of the plurality of monocular images, capturing the defect field region, and transferring the captured defect field region to a non-defect field region and forming the combined image to include the transferred captured defect field region for display to the subject.

In any of the above or another example, the image processing device stores instructions on the memory that, when executed, cause the processor to: combine the plurality of monocular images into the combined image by identifying a common central region of each of the plurality of monocular images and identifying divergent peripheral regions of the plurality of monocular images; and form the combined image to have a first region corresponding to the common central region and a second region formed by combining the divergent peripheral regions into a widen peripheral region that surrounds the first region. In any of the above or another example, the image processing device stores instructions on the memory that, when executed, cause the processor to: form the combined image such that the second region corrects for visual field defect and aberrations of an eye of the subject. In any of the above or another example, the at least one digital monitor comprises a first digital monitor and a second digital monitor each configured for displaying the combined image to a respective eye of the subject.

In any of the above or another example, the image processing device stores instructions on the memory that, when executed, cause the processor to perform a fisheye transformation on a first region of the plurality of monocular images to modify a radial component of the plurality of monocular images, according to:

$$r_{new} = r + ar^3$$

where is a constant.

In any of the above or another example, the image processing device stores instructions on the memory that, when executed, cause the processor to perform a conformal mapping transformation on the plurality of monocular images to modify the radial component according to:

$$r_{new} = r^\beta$$

where β is a constant power of the radial component and β>1

In any of the above or another embodiment, the image processing device may store instructions on the memory that, when executed, cause the processor to perform a polynomial transformation to map points from a wider annulus around a center of the plurality of monocular images to a thinner annulus, for forming the combined image.

In still another aspect, an apparatus may include a wearable spectacle having a housing. The wearable spectacle may have a controllable projector configured to project a patterned image onto the retina of the subject. The apparatus may further include an image processing device having a processor, memory, and an input device. The image processing device may be coupled to the controllable projector.

In some examples, the image processing device is configured to: (A) receive to the input device a visual scoring signal indicative of the patterned image experienced at the retina of the subject; (B) analyze the visual scoring signal, determine if a distortion experienced at the retina is present based on the visual scoring signal, and when a distortion is present, determine a pattern adjustment for the patterned image based on the visual scoring signal; and (C) adjust the patterned image based on the pattern adjustment to form a revised patterned image and project the revised patterned image onto the retina and repeat (A).

In any of the above or another example, the corrective imaging element is an adjusted intensity of the peripheral element relative to a central image region of the visible scene or an adjusted intensity of the central element relative to a peripheral image region of the visible scene. In any of the above or another example, the image processing device is configured to: adjust the position and/or composition of the corrective imaging element in response to detected movement of the eye of the subject. In any of the above or another example, the image processing device is configured to: identify one or more affected regions of one or both eyes of the subject; and determine the corrective imaging element that compensates for the one or more affected regions.

In yet another aspect, an apparatus may include a wearable spectacle device, the wearable spectacle device may include at least one optical element for passing an image of a visible scene to the subject. The wearable spectacle device may further include at least one digital monitor corresponding to the at least one optical element, the at least one digital monitor being configured to overlay a corrective imaging element over an image of the visible scene of the at least one optical element. The apparatus may also include an image processing device having a processor and a memory. The image processing device may be coupled to the at least one digital monitor.

In one example, the image processing device configured to generate the corrective imaging element as a peripheral element of the image of the visible scene to correct for a peripheral visual field defect or generate the corrective imaging element as a central element of the image of the visible scene to correct for a central visual field detect. In any of the above or another example, the image processing device may be configured to display the corrective image element over visible scene to the subject.

In any of the above or another example, the corrective imaging element is an adjusted intensity of the peripheral element relative to a central image region of the visible scene or an adjusted intensity of the central element relative to a peripheral image region of the visible scene. In any of the above or another example, the image processing device is configured to: adjust the position and/or composition of the corrective imaging element in response to detected movement of the eye of the subject. In any of the above or another example, the image processing device is configured to: identify one or more affected regions of one or both eyes of the subject; and determine the corrective imaging element that compensates for the one or more affected regions.

In any of the above or another example, the image processing device is configured to: in a testing mode, (i) instruct the at least one digital monitor to display a plurality of testing stimuli to the subject over one or more testing locations in a testing visual field, (ii) instruct an image sensor of the apparatus to capture position indications of the pupil physical condition and/or line of sight during the displaying of the plurality of testing stimuli over the one or more testing locations, and (iii) determine the one or more affected regions in the testing visual field and determine one or more vision pathologies of the subject. In any of the above or another example, the plurality of stimuli differ in contrast levels with respect to each other and with respect to a baseline contrast level.

In any of the above or another example, the at least one digital monitor is contained with a layer of the at least one optical element. In any of the above or another example, the layer is an inner layer or an outer layer of the at least one optical element.

BRIEF DESCRIPTION OF THE DRAWINGS

The figures described below depict various aspects of the system and methods disclosed herein. It should be understood that each figure depicts an example of aspects of the present systems and methods.

FIG. 31B schematically illustrates presentation of a reference image comprising a grid displayed to a subject or projected onto a cornea or retina of the subject via wearable spectacles according to various embodiments described herein;

FIG. 31C illustrates an example grid for manipulation by a subject according to various embodiments described herein;

FIG. 31D illustrates an example manipulation of the grid illustrated in FIG. 31C according to various embodiments described herein;

DETAILED DESCRIPTION

Figure 1A:
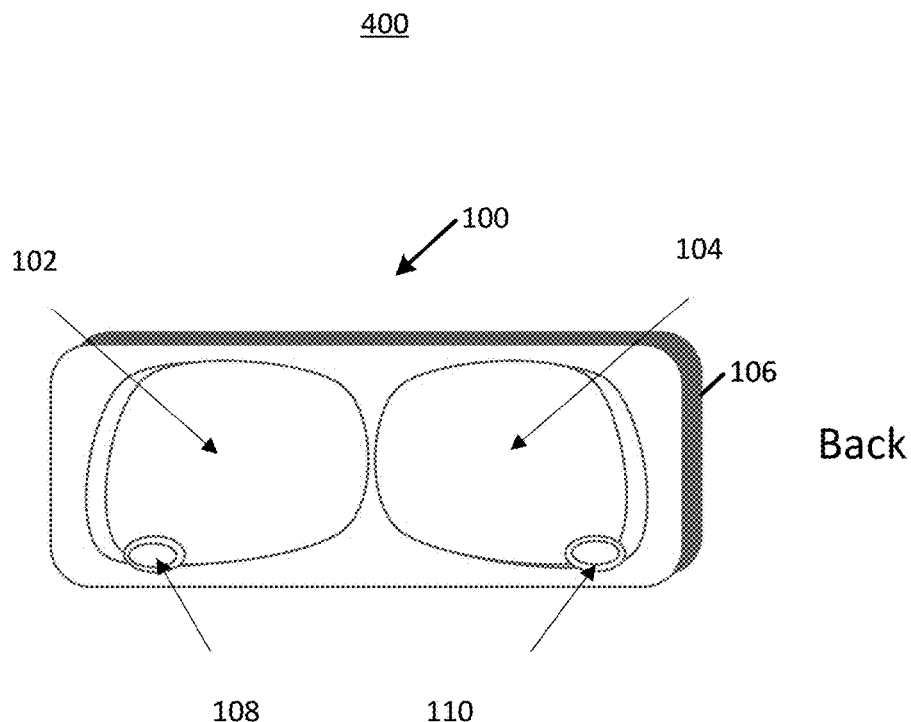
FIGS. 1A-1C illustrate views of an example spectacles device according to various embodiments described herein.

The present application provides techniques and devices for testing, identifying, and compensating for ocular pathologies affecting the visual field for a patient. These ocular pathologies include, for example, pathologies of the optic nerve such as glaucoma, optic neuritis, and optic neuropathies, pathologies of the retina such as macular degeneration, retinitis pigmentosa, pathologies of the visual pathway as microvascular strokes and tumors and other conditions such as presbyopia, strabismus, high and low optical aberrations, monocular vision, anisometropia and aniseikonia, light sensitivity, anisocorian refractive errors, and astigmatism.

The techniques herein provide vision systems, spectacle devices, and associated systems and devices thereof, for testing, enhancing, and/or correcting vision or a perception of a visual field.

One or more devices of the vision system may be configured for use within one or more of the systems described herein or may be configured for separate use. For example, in various embodiments, a vision system comprises a spectacle device. It will be appreciated that devices described herein may include one or more systems comprising one or more devices. Thus devices may include one or more associated systems or devices.

The vision system may include an image processing device (which may also be referred to as an image processor, computing device, or the like) configured to perform the herein described image processing operations of the vision system. As described herein, the image processing device may be fully or partially integrated with the spectacles device or may be fully or partially external, e.g., remote, to the spectacles device. Such external image processing devices may be configured for wired or wireless communication with the spectacles device.

Exemplary embodiments of the spectacle device includes a wearable spectacles device. Some embodiments of the spectacle device may employ digital aspects with respect to one or more of imaging, imaging processing, communication, display, or other functionalities described here. Various embodiments of the spectacles device, either alone or together with other systems or devices, may be configured to provide a personalized, customized visually corrected vision field to a subject. In some examples, a spectacles device may comprise digital therapeutic corrective spectacles (also termed herein "DTS"). One exemplary spectacles device may comprise wearable digital spectacles for use by individuals for purposes other than therapeutic correction. For example, the spectacles device may be configured to enhance normal vision, field of view, or perception thereof, of a subject, e.g., by increasing or decreasing field of view, modification of a horizontal, vertical, and/or diagonal angle of view, modification of light provided to one or more regions, modification of a size an object or regions within one or more regions of a field of view, and/or relocation of an object or region to another region of the field of view. The spectacle devices herein may be activated by voice activation, remote control (e.g., cellular phone) or body movement (e.g., winks or hard double blinks), in some examples.

Embodiments of vision systems or spectacle devices may include one or more digital monitors. Visions systems or spectacle devices may also include one or more image sensors. In some embodiments, image sensors may include one or more outward directed image sensors for imaging a viewing environment of the subject (which may also be referred to as a user, wearer, or patient), which may typically correspond to a field of view originating from the eyes of a subject, but which may be taken from other origination points in some configurations. Outward directed image sensors may comprise, for example, one or more cameras positioned to capture all or a portion of one or more fields of view, which may include more or less of a field of view relative to a human. In these or other embodiments, one or more image sensors may include one or more inward directed image sensors for imaging aspects of a subject such as a physical state of a pupil of the subject. For example, a spectacles device may include inward directed image sensors such as cameras (visible, infrared, etc.) that capture and track line of sight, limbus, pupil data for a subject, corneal data for a subject, retinal image, image of a pattern reflected on the cornea or the retina. Line of sight, also known as the visual axis, may be achieved by tracking the pupil, the limbus (which is the edge between the cornea and the sclera), or even track blood vessel on the surface of the eye or inside the eye. Thus, image sensors may be used to image limbus, blood vessels, as well as the pupil.

Some vision systems or spectacle devices may include one or more displays, which may be referred to as digital monitors. Digital monitors may include a monitor for generating a display on a screen, which may include projection onto a screen which may include heads-up display, or a monitor for projection of the display onto one or both eyes of a subject. For example, a spectacles device may include one or more digital monitors for display of images to the subject. These or other vision systems or spectacle devices may include projectors configured to display images to a subject by projecting images on a monitor, e.g., a screen such as a glass, or onto an eye of the subject, e.g., retinal projection. In some examples, the devices include a headset with two miniature external viewfinder cameras. Headsets may include, for example, a wearable spectacles device as described herein. In some examples, spectacle devices may include a spectacles device configured to recreate an entire visual field as a digitized corrected image to provide an optimized rendition of the visual field. In some examples, the vision systems or spectacle devices may include a spectacle device comprising an alternative reality (AR) or virtual reality (VR) headset. In these or other examples, the systems and devices may include spectacle devices wherein the visual field may be viewed by a user, but the visual field has been corrected by the introduction of a corrected image.

In some examples, a vision system or spectacles device may be configured to process and/or display images to correct lower and/or higher order aberrations and/or refractive errors and thus provide improved customized personalized vision to the subject. In some examples, systems or devices including a spectacles device may be configured to treat a myriad of ocular anomalies. Ocular anomalies includes, for example, various classes of diagnosable conditions, related to one or more of visual field defects, decreased vision effects, field of vision distortions, secondary effects, and double vision. The ocular anomalies that can be corrected through the operation of the systems or devices described herein may include, but are not limited to, one or more of presbyopia, double vision caused by strabismus, glaucoma, age related macular degeneration, monocular vision, anisometropia and aniseikonia, light sensitivity, and anisocoria, pathologies of the optic nerve such as glaucoma, optic neuritis, and optic neuropathies, pathologies of the retina such as macular degeneration, retinitis pigmentosa, pathologies of the visual pathway as microvascular strokes and tumors and other conditions such as presbyopia, strabismus, high and low optical aberrations, refractive errors, and astigmatism.

In exemplary embodiments, a vision system or spectacles device may be configured to provide an enhanced and/or corrected image displayed to a subject, either through digital recreation or through augmenting the visual field. In exemplary embodiments, the spectacles device may include one or more projectors configured to project a digital recreated or augmented image into the eye of the subject, projecting onto the retina, via retinal projection.

In exemplary embodiments, a vision system or spectacles devices may be configured to correct or enhance the field of view of the subject, e.g., correcting or increasing the angle of vision of the subject. In some examples, the central and peripheral view regions are affected differently (e.g., through zooming in or zooming out the images displayed or projected to the subject eye) to enhance the view angle of the subject or to increase the detail perceived by the subject.

In exemplary embodiments, a vision system or spectacles device may be configured to compensate for changes in the localized brightness of the visual field for a patient, e.g., as determined from visual field test results, which may be performed together with the spectacles devices or separate. The spectacles devices may be configured to compensate by providing increased brightness to areas of the visual field with lower sensitivity as compared to areas with normal sensitivity. In some examples, spectacle devices or associated systems are configured to register and track these lower sensitivity areas using the pupil and visual axes. The spectacle devices or associated systems herein employ compensation techniques for these lower sensitivity regions to provide a homogenous image from the perception of the subject. This compensation techniques remove the localized cloud of the subject with respect to the low sensitivity areas to improve visual performance and increase the functional visual field of the subject.

In exemplary embodiments, a vision system or spectacles device may include a testing mode, e.g., to identify and test aspects a subject's vision or functional visual field. In this or other embodiments, spectacle devices may include a visioning mode, e.g., to provide enhanced or corrected vision or visual field, which may be in real time and/or personalized to the subject. In some embodiments, spectacle devices or associated systems include both a testing mode and visioning mode, which may be configured to utilize follow-up or maintenance testing procedures for streamlined reprogramming of visioning mode processing as the subject's vision changes. In some embodiments of the spectacles device may include a programing interface configured to receive updates with respect to testing mode operations and/or visioning mode operations. For example, the programing interface may include a wired or wireless communication port including a receiver or transceiver. In some embodiments, the spectacles device may be configured to receive updates comprising testing results performed by a testing mode of the system or another system or device for integration with the visioning mode operations. In some embodiments, updates may include data or instructions provided by the subject, such as via a user interface in signal communication with the programing interface via the communication port. The data or instructions may be conveyed by the user via interactions with a user interface comprising a tablet, smart phone, computer, or a peripheral device in a testing mode, which may include a feedback mode, as described herein or during operation of a visioning mode, which may similarly include a feedback mode. Some embodiments may include a user interface mounted on a spectacle device such as a switch, touch sensor, capacitance sensor, or other interface through which a user may convey or adjust parameters with respect to the vision or corrective profile by which the visioning mode processes and presents images to the subject.

In exemplary embodiments, a vision system or spectacles device may include one or more outward directed image sensors, e.g., cameras, positioned to image a field of vision of the subject and display images on a monitor, e.g., display screen, glass of the spectacles, or project the images into an eye of the subject person wearing the spectacles device after processing the image. The processing of the image may comprise customizing the image to treat and/or correct for the aforementioned conditions or to enhance vision or functional visual field. As introduced above, spectacles devices may include or associate with one or more inward directed image sensors, e.g., cameras, that observe the subject eye, line of sight, pupil size, and/or position of the limbus to register and/or adjust for the aforementioned corrections or enhancements.

In exemplary embodiments, a vision system or spectacles device may be configured to correct for the lower and/or high order visual aberration in a dynamic manner. The techniques may detect the size of the pupil, accommodative status and change in line of sight and thus changes the visual aberration corrective profile accordingly. The higher and/or lower order aberrations may be captured in relation to the pupil size, state of accommodation and direction of gaze using aberrometer to allow the spectacles device to create such a dynamic corrective profile. The image projected to the subject by the techniques herein may be inversely distorted according to actual aberrations of the subject so that his/her own aberrations are re-inversed to provide the best vision. Some embodiments may implement techniques to detect the state of accommodation by detecting the signs of the near reflex, namely miosis (decrease the size of the pupil) and convergence (inward crossing of the pupil). For example, spectacles devices may include a pupil to detect pupil size and/or a line of sight tracker to detect direction of gaze. Those inputs allow the techniques to detect the correction profile to be displayed.

In exemplary embodiments, the present techniques may be implemented to provide vision correction that automatically autofocuses images displayed via the one or more monitors to provide near vision. To further augment and enhance near vision, the inward directed image sensors, e.g., cameras, may detect if the subject is trying to look at a near target by detecting signs of near reflex, miosis (decrease in pupil size) and convergence (inward movement of the eye), and automatically autofocus to provide better near vision. Near correction for reading a newspaper is different than that for reading from a computer monitor, for instance. Example spectacle devices and/or associated systems described herein may be configured to determine how far away an object is by quantifying the amount of the near reflex exerted by the subject and thus provide a corresponding focusing correction.

In exemplary embodiments, a vision system or spectacle device may be configured to correct for double vision secondary to strabismus in a dynamic manner. For example, pupil and line of sight tracking may operatively cooperate with inward directed image sensors to track pupil, limbus or eye structure such as blood vessels of the subject and line of sight. This tracking may be utilized to inform the displacement of images displayed to the subject, e.g., projected or displayed on one or more monitors or projected onto the eyes of the subject, in a dynamic way to compensate for the strabismus and to prevent double vision in all gazes.

In exemplary embodiments, a vision system or spectacle device may be configured to improve vision and safety of patients with visual field defects, such as glaucoma patients. Such subjects may have missing parts of visual fields. For instance, if a car or person is in a blind part of this subject vision, then that car or person is invisible for that subject. The vision systems and spectacles devices described herein may be implemented correct for these blind spots. For example, the visual field defect may be detected using a visual field testing mode of the vision system or spectacle device. In some examples, software executed by example systems and devices herein may be configured to redistribute images captured by an outward directed image sensor, e.g., camera, to the subject's actual functional visual field. The actual visual field may be dynamically projected in reference to the pupil or line of sight, e.g., utilizing data obtained by pupil and line of sight tracking. In other words, the present techniques may bring the picture of the car or person that is within the subject's blind spot to a position outside of the subject's blind spot, thereby, improving safety and functionality of those subjects.

In patients with age related macular degeneration or other conditions that affect the macula of the eye, who has central blind spot, the vision system or spectacle device may be configured to distribute an image or portion thereof to the peripheral or paracentral part of their functional visual field. The present techniques may project parts of the image of interest to healthy parts of the retina, for example, and avoid the unhealthy parts of the retina. In some examples, a vision system or spectacle device may include a testing mode to delineate seeing and blind parts of the visual field that is used during modification of the image to direct its distribution.

In monocular patients or patient having poor vision in one eye, the vision system or spectacles device may capture a normal binocular visual field and distribute the normal binocular visual field to the actual functional visual field of both eyes to provide the patient with the widest possible field of view. Indeed, these spectacles devices may be implemented to augment the visual field of a normal subject, for military engagement and other applications, to provide a subject with an enhanced visual field. For example, the spectacles device may be implemented to enhance a visual field of a subject in athletic applications, physician applications, driving applications, etc.

Anisometropia results from unequal refractive power of both eyes of a subject. In various embodiments, the vision system or spectacle device may be configured to correct for anisometriopia by modification of the image size to create images of equal sizes and displaying or projecting them to both eyes to avoid visual disturbances.

Unlike Lenses of glass spectacles that cause distortion to the visual field such as minification or magnification of the image of interest, the present techniques may be utilized to be independent of corrective lenses to not affect visual field of subjects.

In some examples, the vision system or spectacle device, may be configured to display or project light independent from the brightness of the surrounding environment. In one example, displayed or projected light may be adjusted automatically according to a size of a pupil as detected by the systems and/or devices or manually, e.g., via a user interface coupled to, e.g., in signal communication with, the spectacles device, as a patient requires. The pupil tends to constrict more in bright environment and dilate in less bright environment. As introduced above, the systems and devices herein may be configured to detect degree of constriction/dilation and adjust for brightness accordingly, which may be in a personalized and customized manner. Subjects with anisocoria, for example, may use the present techniques to allow for adjustment of brightness for each eye separately. In some examples, this is done automatically by the system or device, as it detects the pupil size.

FIG. 1A illustrates an example spectacles device 100 forming a wearable device for a subject. In some embodiments, the spectacles device 100 may be a part of a visioning system as described herein. The spectacles device 100 includes a left eyepiece 102 and a right eyepiece 104. Each eyepiece 102 and 104 may contain and/or associate with a digital monitor configured to display (or project) recreated images to a respective eye of the subject. In various embodiments, digital monitors may include a display screen, projectors, and/or hardware to generate the image display on the display screen. It will be appreciated that digital monitors comprising projectors may be positioned at other locations to project images onto an eye of the subject or onto an eyepiece comprising a screen, glass, or other surface onto which images may be projected. In one embodiment, the left eye piece 102 and right eyepiece 104 may be positioned with respect to the housing 106 to fit an orbital area on the subject such that each eyepiece 102, 104 is able to collect data and display/project image data, which in a further example includes displaying/projecting image data to a different eye.

Each eyepiece 102, 104 may further includes one or more inward directed sensors 108, 110, which may be inward directed image sensors. In an example, inward directed sensors 108, 110 may include infrared cameras, photodetectors, or other infrared sensors, configured to track pupil movement and to determine and track visual axes of the subject. The inward directed sensors 108, 110, e.g., comprising infrared cameras, may be located in lower portions relative to the eye pieces 102, 104, so as to not block the visual field of the subject, neither their real visual field nor a visual field displayed or projected to the subject. The inward directed sensors 108, 110 may be directionally aligned to point toward a presumed pupil region for better pupil and/or line of sight tracking. In some examples, the inward directed sensors 108, 110 may be embedded within the eye pieces 102, 104 to provide a continuous interior surface.

Figure 1B:
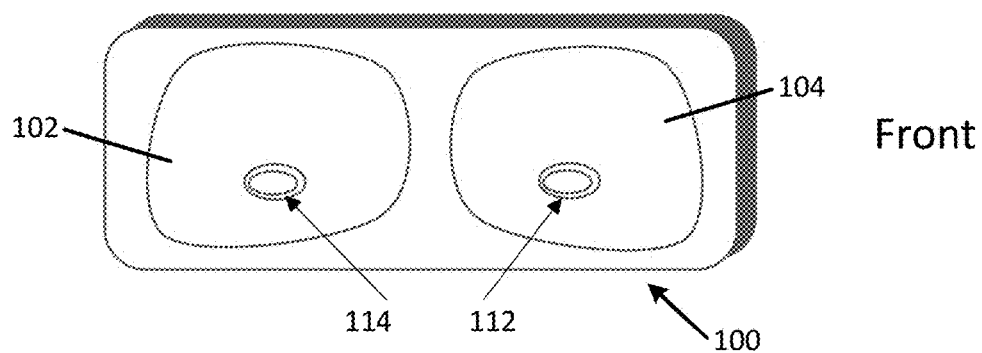

FIG. 1B illustrates a front view of the spectacles device 100, showing the front view of the eye pieces 102, 104, where respective outward directed image sensors 112, 114 comprising field of vision cameras are positioned. In other embodiments, fewer or additional outward directed image sensors 112, 114 may be provided. The outward directed image sensors 112. 114 may be configured to capture continuous images. The spectacles device 100 or associated vision system may be further configured to then correct and/or enhance the images, which may be in a customized manner based on the optical pathologies of the subject. The spectacles device 100 may further be configured to display the corrected and/or enhanced image to the subject via the monitors in a visioning mode. For example, the spectacles device may generate the corrected and/or enhanced image on a display screen associated with the eyepiece or adjacent region, project the image onto a display screen associated with the eyepiece or adjacent region, or project the image onto one or more eyes of the subject.

Figure 1C:
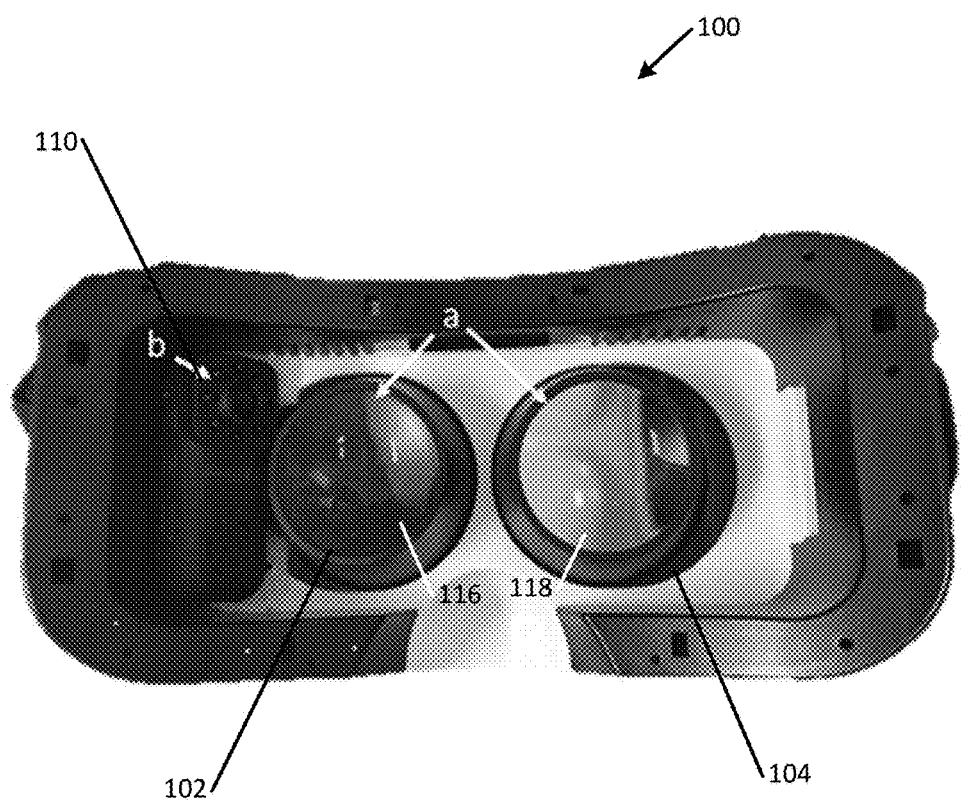

FIG. 1C is an image of an example constructed spectacles device 100 comprising eyepieces 102, 104 including two digital monitors, with focusing lens 116, 118 In this example, only one inward directed optical sensor 110 is included for pupil and line of sight tracking, however, in other examples, multiple inward directed optical sensors 110 may be provided.

In exemplary embodiments, the spectacles device 100 may include a testing mode. In an example testing mode, the inward directed sensors 108, 110 track pupil movement and perform visual axis tracking (e.g., line of sight) in response to a testing protocol. In this or another example, the inward directed sensors 108, 110 may be configured to capture a reflection of a pattern reflected on the cornea and/or retina to detect distortions and irregularities of the cornea or the ocular optical system.

Testing mode may be used to perform a visual assessments to identify ocular pathologies, such as, high and/or low order aberrations, pathologies of the optic nerve such as glaucoma, optic neuritis, and optic neuropathies, pathologies of the retina such as macular degeneration, retinitis pigmentosa, pathologies of the visual pathway as microvascular strokes and tumors and other conditions such as presbyopia, strabismus, high and low optical aberrations, monocular vision, anisometropia and aniseikonia, light sensitivity, anisocorian refractive errors, and astigmatism. In the testing mode, data may be collected for the particular subject and used to correct captured images before those images are displayed, which may include projected as described herein, to the subject by the monitors.

In some examples, external sensors may be used to provide further data for assessing visual field of the subject. For example, data used to correct the captured image may be obtained from external testing devices such as visual field testing devices, aberromaters, electro-oculograms, or visual evoked potential devices. Data obtained from those devices may be combined with pupil or line of sight tracking for visual axis determinations to create the corrective profile of used to correct the images being projected of displayed to the viewer.

The spectacles device 100 may include a visioning mode, which may be in addition to or instead of a testing mode. In visioning mode, one or more outward directed image sensors 112, 114 capture images that are transmitted to an imaging processor for real-time image processing. The image processor may be embedded within, e.g., integrated or attached to, the spectacles device 100 or may be external thereto, such as associated with an external image processing device. The imaging processor may be a component of a visioning module and/or include a scene processing module as described elsewhere herein.

The spectacles device 100 may be communicatively coupled with one or more imaging processor through wired or wireless communications, such as through a wireless transceiver embedded within the spectacles device 100. An external imaging processor may include a computer such as a laptop computer, tablet, mobile phone, network server, or other computer processing devices, centralized or distributed, and may be characterized by one or more processors and one or more memories. In the discussed example, the captured images are processed in this external image processing device; however, in other examples, the captured images may be processed by an imaging processor embedded within the digital spectacles. The processed images, e.g., enhanced to improve functional visual field or other vision aspects and/or enhanced to correct for the visual field pathologies of the subject, are then transmitted to the spectacles device 100 and displayed by the monitors for viewing by the subject.

In an example operation of a vision system including the spectacles device, real-time image processing of captured images may be executed by an imaging processor, e.g., using a custom-built MATLAB (MathWorks, Natick, Mass.) code, that runs on a miniature computer embedded in the spectacles device. In other examples, the code may be run on an external image processing device or other computer wirelessly networked to communicate with the spectacles device. In one embodiment, the vision system, including the spectacles device, image processor, and associated instructions for executing visioning and/or testing modes, which may be embodied on the spectacles device alone or in combination with one or more external devices, e.g., laptop computer, may be operated in two modes, a visioning mode and a separate testing mode.

Figure 2:
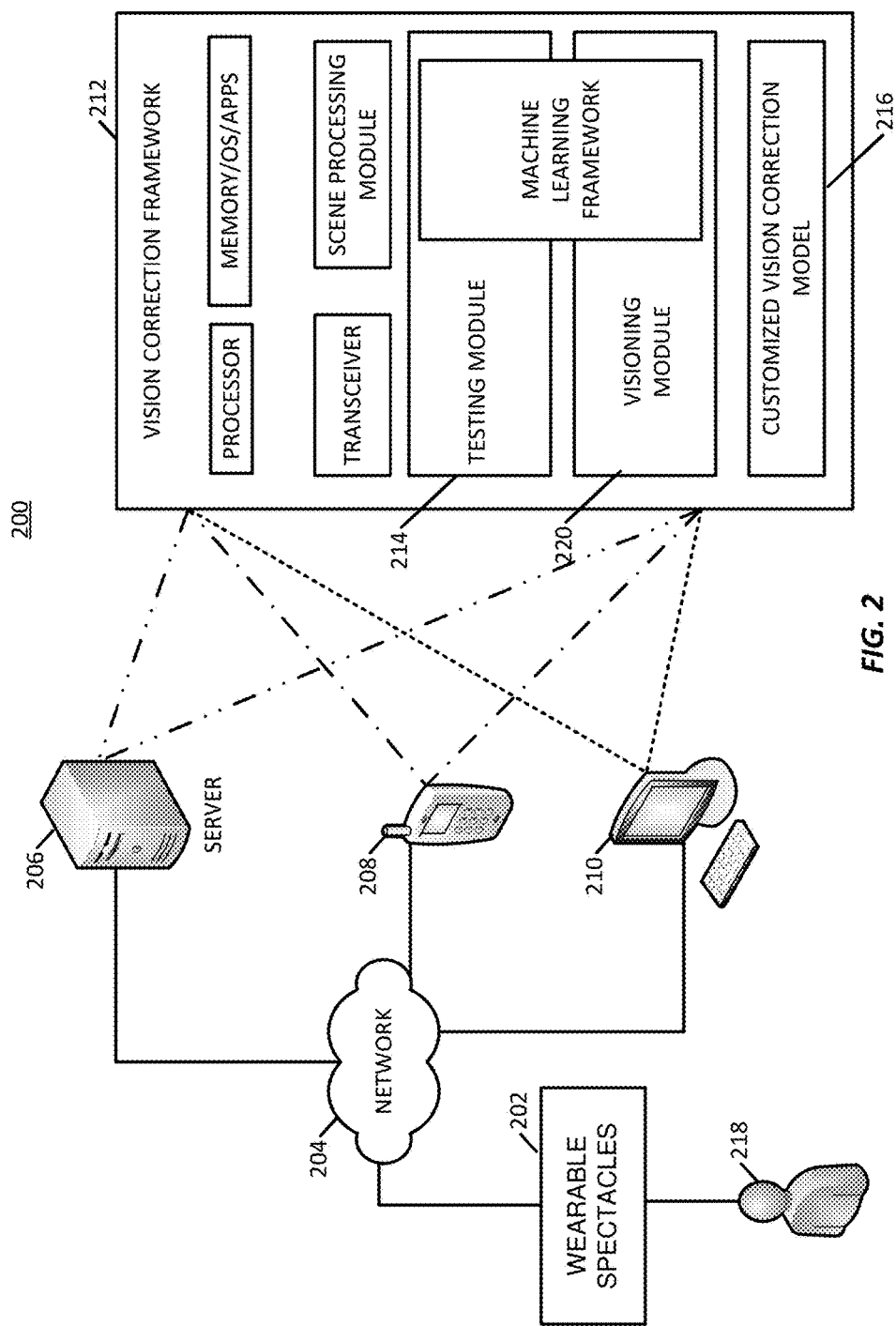
FIG. 2 schematically illustrates an example vision system according to various embodiments described herein.

FIG. 2 illustrates an example vision system 200 including a spectacles device 202 communicatively coupled to a network 204 for communicating with a server 206, mobile cellular phone 208, or personal computer 210, any of which may contain a visional correction framework 212 for implementing the processing techniques herein, such as image processing techniques, which may include those with respect to the testing mode and/or visioning mode. In the illustrated example, the visional correction framework 212 includes a processor and a memory storing an operating system and applications for implementing the techniques herein, along with a transceiver for communicating with the spectacles device 202 over the network 204. The framework 212 contains a testing module 214, which includes a machine learning framework in the present example. The machine learning framework may be used along with a testing protocol executed by the testing module, to adaptively adjust the testing mode to more accurately assess ocular pathologies, in either a supervised or unsupervised manner. The result of the testing module operation may include development of a customized vision correction model 216 for a subject 218. A visioning module 220, which in some embodiments may also include a machine learning framework having accessed customized vision correction models, to generate corrected visual images for display by the spectacles device 202. The vision correction framework 212 may also include a scene processing module which may process images for use during testing mode and/or visioning mode operations and may include operations described above and elsewhere herein with respect to a processing module. As described above and elsewhere herein, in some embodiments, the spectacle device 202 may include all or a portion of the vision correction framework 212.

In the testing mode, the spectacles device 100 or 202, and in particular the one or more inward directed image sensors comprising tracking cameras, which may be positioned along an interior of the spectacles device 100 or 202, may be used to capture pupil and visual axis tracking data that is used to accurately register the processed images on the subject's pupil and visual axis.

Figure 3:
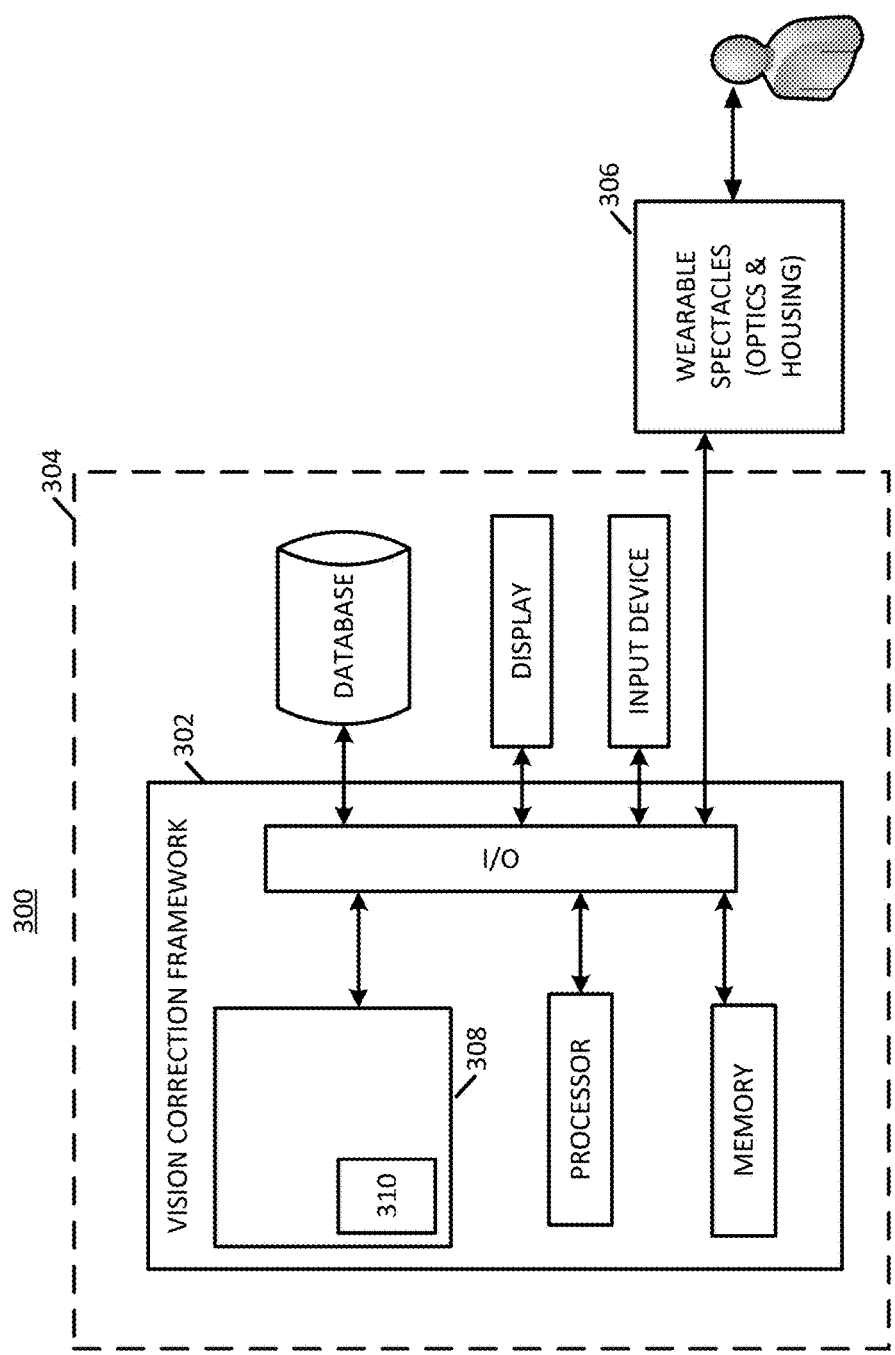
FIG. 3 schematically illustrates a device with a vision correction framework implemented on an image processing device and a wearable spectacles device according to various embodiments described herein.

FIG. 3 illustrates a vision system 300 comprising a vision correction framework 302. The vision correction framework 302 may be implemented on a image processing device 304 and a spectacles device 306 for placing on a subject. The image processing device 304 may be contained entirely in an external image processing device or other computer, while in other examples all or part of the image processing device 304 may be implemented within the spectacles device 306.

The image processing device 304 may include a memory 308 storing instructions 310 for executing the testing and/or visioning modes described herein, which may include instructions for collecting high-resolution images of a subject from the spectacles device 306. In the visioning mode, the spectacles device 306 may capture real-time vision field image data as raw data, processed data, or pre-processed data. In the testing mode, the spectacles device may project testing images (such as the letters "text" or images of a vehicle or other object) for testing aspects of a vision field of a subject.

The spectacles device 306 may be communicatively connected to the image processing device 304 through a wired or wireless link. The link may be through a Universal Serial Bus (USB), IEEE 1394 (Firewire), Ethernet, or other wired communication protocol device. The wireless connection can be through any suitable wireless communication protocol, such as, WiFi, NFC, iBeacon, Bluetooth, Bluetooth low energy, etc.

In various embodiments, the image processing device 304 may have a controller operatively connected to a database via a link connected to an input/output (I/O) circuit. Additional databases may be linked to the controller in a known manner. The controller includes a program memory, the processor (may be called a microcontroller or a microprocessor), a random-access memory (RAM), and the input/output (I/O) circuit, all of which may be interconnected via an address/data bus. It should be appreciated that although only one microprocessor is described, the controller may include multiple microprocessors. Similarly, the memory of the controller may include multiple RAMs and multiple program memories. The RAM(s) and the program memories may be implemented as semiconductor memories, magnetically readable memories, and/or optically readable memories, for example. The link may operatively connect the controller to the capture device, through the I/O circuit.

The program memory and/or the RAM may store various applications (i.e., machine readable instructions) for execution by the microprocessor. For example, an operating system may generally control the operation of the vision system 300 such as operations of the spectacles device 306 and/or image processing device 304 and, in some embodiments, may provide a user interface to the device to implement the processes described herein. The program memory and/or the RAM may also store a variety of subroutines for accessing specific functions of the image processing device described herein. By way of example, and without limitation, the subroutines may include, among other things: obtaining, from a spectacles device, high-resolution images of a vision field; enhancing and/or correcting the images; and providing the enhanced and/or corrected images for display to the subject by the spectacles device 306.

In addition to the foregoing, the image processing device 304 may include other hardware resources. The device may also include various types of input/output hardware such as a visual display and input device(s) (e.g., keypad, keyboard, etc.). In an embodiment, the display is touch-sensitive, and may cooperate with a software keyboard routine as one of the software routines to accept user input. It may be advantageous for the image processing device to communicate with a broader network (not shown) through any of a number of known networking devices and techniques (e.g., through a computer network such as an intranet, the Internet, etc.). For example, the device may be connected to a database of aberration data.

Example—"Text" Testing Mode

In an example implementation of the vision system, testing was performed on 4 subjects. A testing protocol included a display of text at different locations one or more display monitors of the spectacles device. To assess the subject's vision field of impaired regions, the word "text" was displayed on the spectacle monitors for each eye, and the subject was asked to identify the "text." Initially the "xt" part of the word "text" was placed intentionally by the operator on the blind spot of the subject. All 4 subjects reported only seeing "te" part of the word. The letters were then moved using software to control the display, specifically. The text "text" was moved away from the blind spot of the subject who was again asked to read the word. Subjects were able to read "text" stating that now the "xt" part of the word has appeared.

Figures 6A, 6B, 6C:
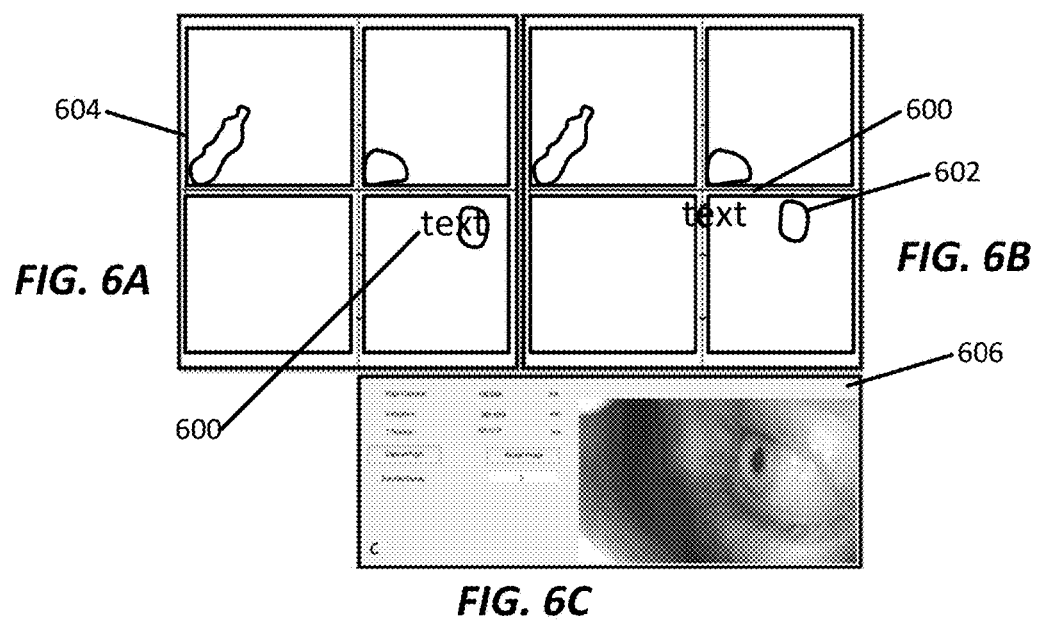
FIGS. 6A-6C illustrate an example assessment protocol for a testing mode process including pupil tracking according to various embodiments described herein.

An example of this assessment protocol of a testing mode is shown in FIGS. 6A-6C. As shown in FIGS. 6A & 6B, the code automatically detects the blind spots on a Humphrey visual field. The word "text" 600 is projected so that "xt" part of the word is in a blind spot 602 (FIG. 6A). The subject was asked to read the word. The word "text" 600 was then moved away from the blind spot 602 (FIG. 6B) and the subject was asked to read it again. The word "text" 600 can be displayed at different coordinates of the vision field of the subject, with the vision field divided into 4 coordinates in the illustrated example. This protocol allows for identification of multiple blind spots, including peripheral blind spot 604. The text may be moved around over the entire vision field of the subject, with the subject being asked to identify when all or portions of the text is not visible or partially visible or visible with a reduced intensity.

The pupil tracking functionalities described herein may include pupil physical condition (e.g., visual axis, pupil size, and/or limbus), alignment, dilation, and/or line of sight. Line of sight, also known as the visual axis, is a goal that can be achieved by one or more of tracking the pupil, the limbus (which is the edge between the cornea and the sclera), or even track blood vessel on the surface of the eye or inside the eye. Thus, pupil tracking may similarly include limbus or blood vessel tracking. The pupil tracking may be performed utilizing one or more inward facing image sensors as described herein.

In various embodiments, pupil tracking functionalities may be used for determination of parameters for registering the projected image on the visual field of the subject (FIG. 6C).

A GUI 606 display may be displayed to an operator. The GUI 606 may provide information related to the testing. For example, the GUI 606 shows measured visual field defects and the relative location of the image to the defects. The GUI 606 may be operable to allow automatic distribution of the images to the functional part of the visual field but may include buttons to allow the operator to override the automatic mode. The external image processing device may be configured to determine where this assessment text is to be displayed and may wirelessly communicate instructions to the digital spectacles to display the text at the various locations in the testing mode.

Example—"Image" Testing Mode

Figures 7A, 7B, 7C:
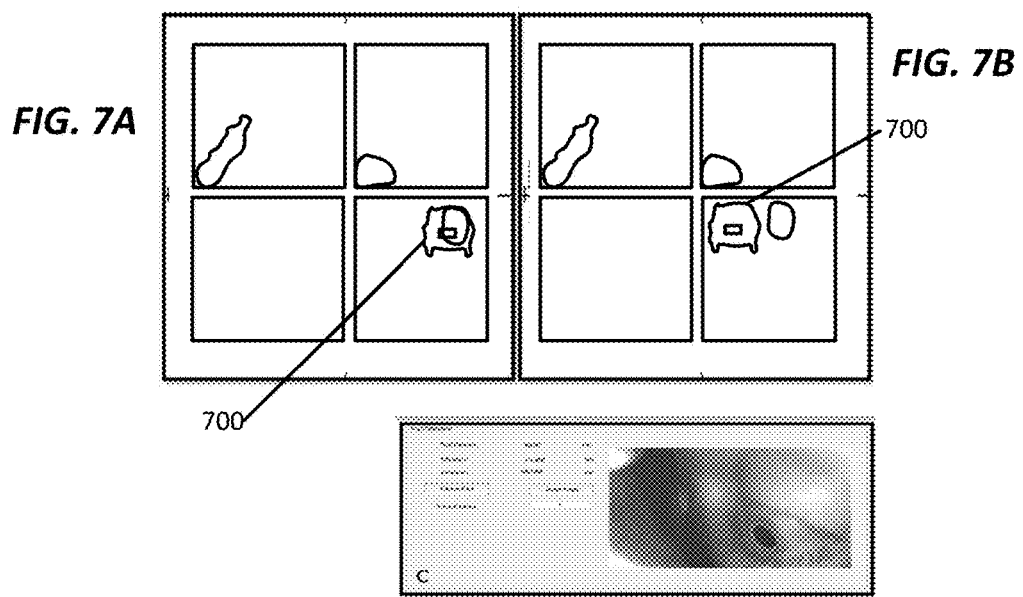
FIGS. 7A-7C illustrate an example assessment protocol for a testing mode process including pupil tracking according to various embodiments described herein.

FIGS. 7A-7C illustrate another example testing mode operation, where instead of "text" being used, the subject was tested to determine whether they could see a car 700 placed in different portions of the visual field, for pupil tracking and affected region determination. The pupil tracking functionality allows the vision system to register the projected image on the visual field of the subject.

Figure 4:
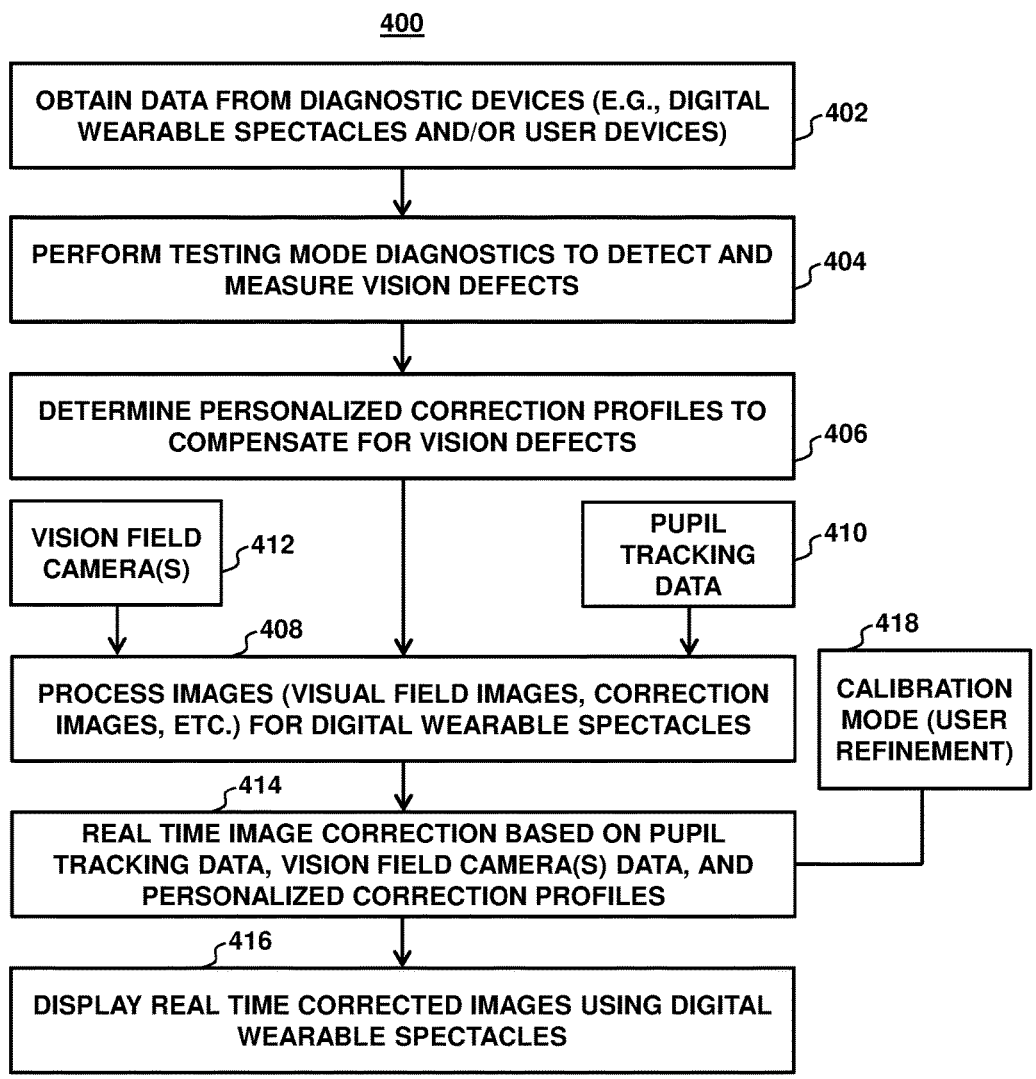
FIG. 4 illustrates an example process including a testing mode and a visioning mode according to various embodiments described herein.

FIG. 4 illustrates a process 400 illustrating an example implementation of both a testing mode and a subsequent visioning mode. At a block 402, in a testing mode, data is obtained from diagnostic devices like image sensors embedded within spectacles device and other user input devices, such as a cellular phone or tablet PC. At a block 404, testing mode diagnostics may be performed to detect and measure ocular anomalies from the received data, e.g., visual field defects, eye misalignment, pupil movement and size, images of patterns reflected from the surface of the cornea or the retina. In an example, a control program and algorithms were implemented using MATLAB R2017b (MathWorks, Inc., Natick, Mass., USA). In various embodiments, a subject or tester may be provided with an option to select to test each eye individually, or test both eye sequentially in one run. In some embodiments, the testing mode may include an applied fast thresholding strategy including contrast staircase stimuli covering central radius of 20 degrees or more using stimuli sequences at predetermined locations. For example, the testing mode may include an applied fast thresholding strategy include four contrast staircase stimuli covering the central 40 degrees' radius using 52 stimuli sequences at predetermined locations, as discussed further below regarding FIGS. 35A & 35B.

Figure 16:
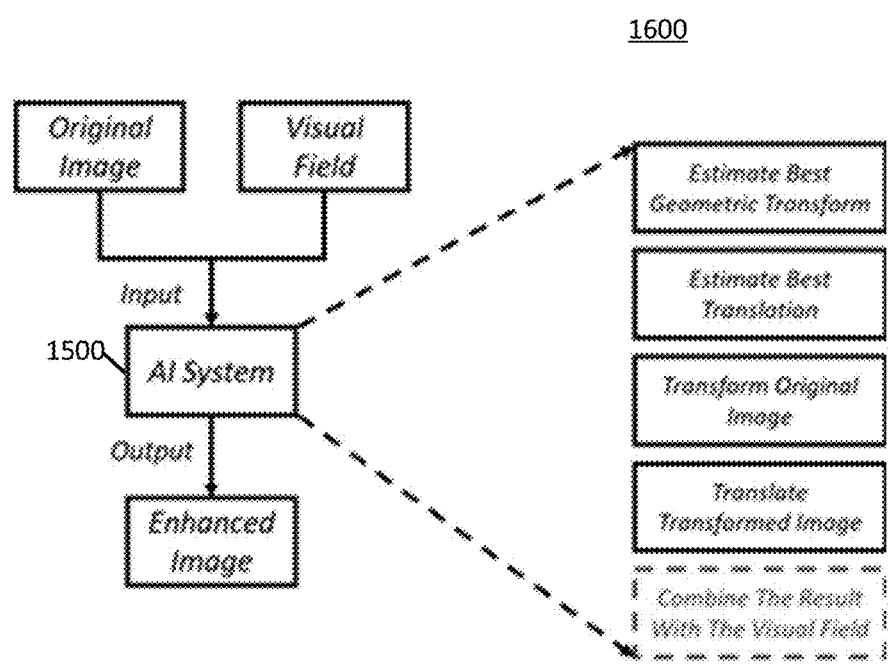
FIG. 16 illustrates a process of an AI system of a machine learning framework according to various embodiments described herein.

At a block 406, the determined diagnostic data may be compared to a database or dataset that stores correction profiles for compensating for identifiable ocular pathologies (see, e.g., FIG. 16 and related discussions).

The identified correction profiles may then personalized to the individual, for example, to compensate for differences in visual axis, visual field defects, light sensitivity, double vision, change in the size of the image between the two eyes, image distortions, decreased vision.

The personalized profiles may be used by a block 408, along with real-time data to process the images, e.g., using an image processor, scene processing module, and/or visioning module. The real-time data may include data detected by one or more inward directed image sensors 410, providing pupil tracking data, and/or from one or more outward directed image sensors comprising one or more vision field cameras 412 positioned to capture a visual field screen. At a block 414, real-time image correction may be performed and the images may be displayed (block 416) on the spectacles device, either as displayed recreated digital images, as augmented reality images passing through the spectacles device with corrected portions overlaid, or as images projected into the retinas of the subject. In some example, the operation of block 414 is performed in combination with a calibration mode 418 in which the user can tune the image correction using a user interface such as an input device that allows a user to control image and correction profiles. For example, users can displace the image of one eye to the side, up and down or cycloterted to alleviate double of vision. In the above or another example, a user may fine tune the degree of visual field transformation (for example fish eye, polynomial, or conformal) or translation to allow enlarging the field of vision without negatively impact the functional vision or cause unacceptable distortions, fine tune the brightness, and contrast, or invert colors).

Figure 5:
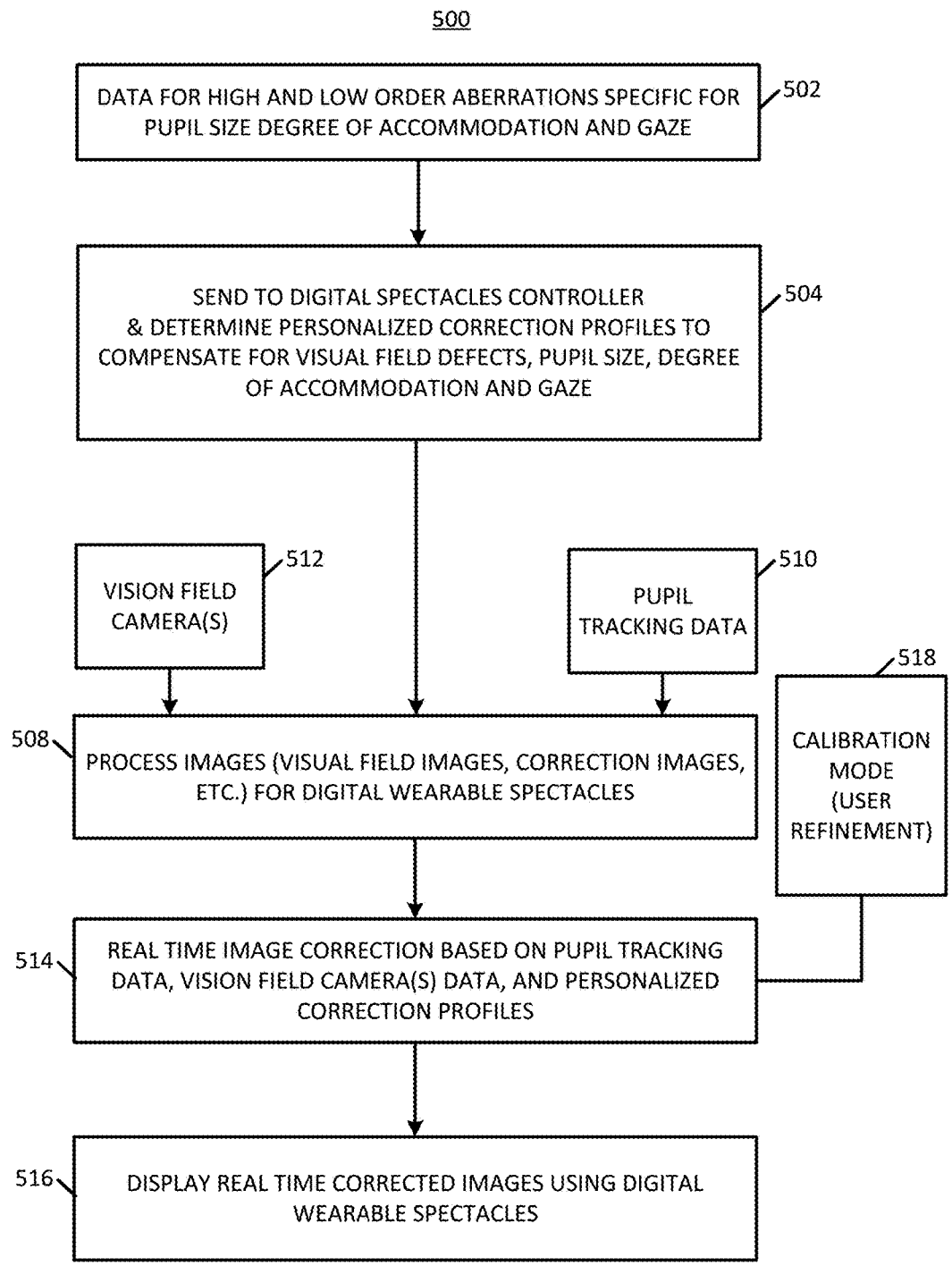
FIG. 5 illustrates an example process including a testing mode and a visioning mode according to various embodiments described herein.

FIG. 5 illustrates another example process 500, similar to that of process 400, for implementation of a testing mode and visioning mode. At a block 502, data for high and low order aberrations for pupil size, degree of accommodation, and gaze, are collected. In some embodiments, all or a portion of the data may be collected from an aberrometer or by capturing the image of a pattern or grid projected on the cornea and/or retina and comparing it to the reference image to detect aberrations of the cornea or the total ocular optical system, for example. The collected data may be sent to a vision correction framework, which, at a block 504, may determine personalized correction profiles similar to block 406 described above. Blocks 508-518 perform similar functions to corresponding blocks 408-418 in process 400.

Figure 8:
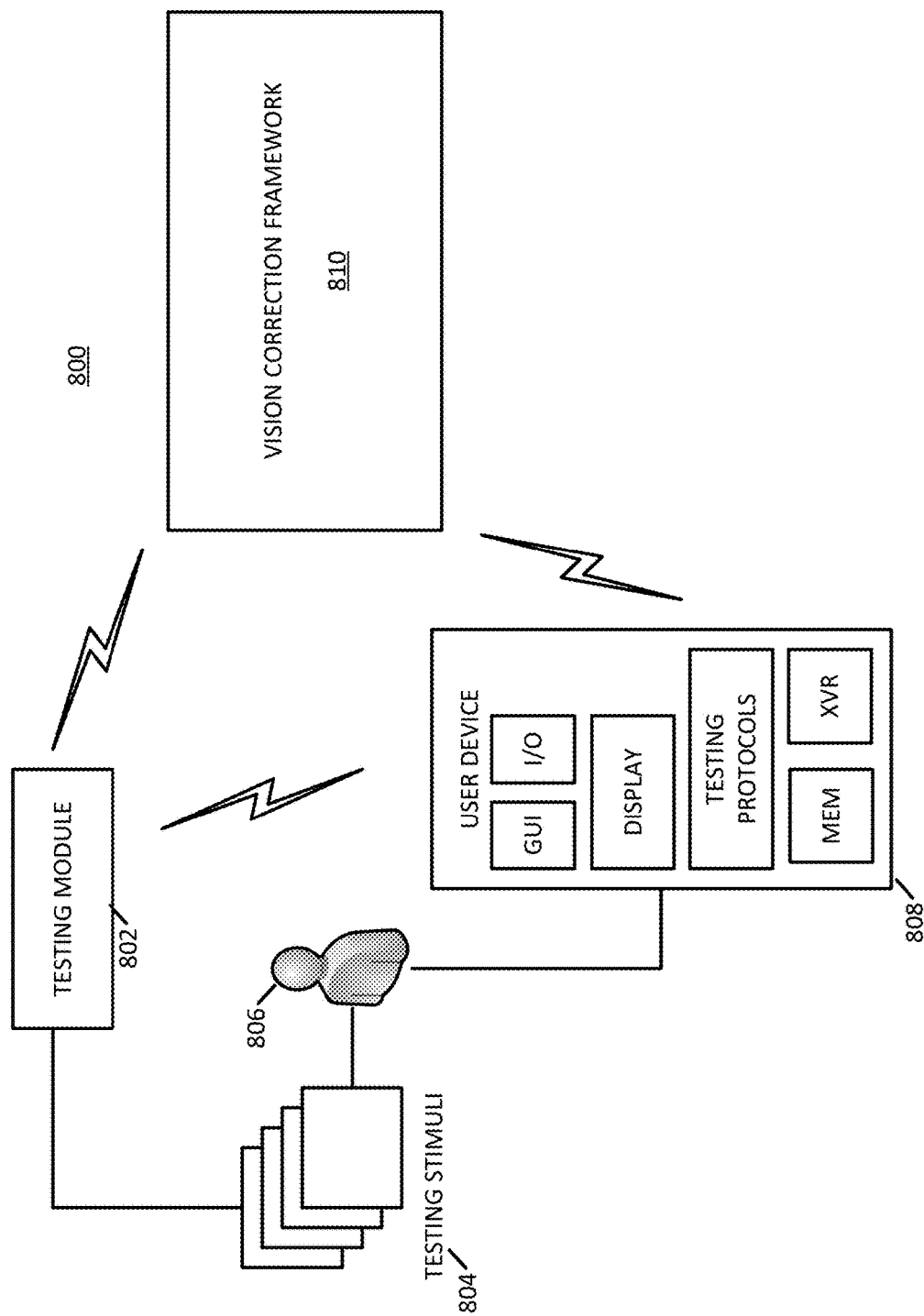
FIG. 8 schematically illustrates a workflow including a testing module that generates and presents a plurality of visual stimuli to a user through a wearable spectacles device according to various embodiments described herein.

FIG. 8 illustrates a workflow 800 showing a testing module 802 that generates and presents a plurality of visual stimuli 804 to a user 806 through the spectacles device. The user 804 has a user device 808 through which the user may interact to provide input response to the testing stimuli. In some examples, the user device 808 may comprise a joystick, electronic clicker, keyboard, mouse, gesture detector/motion sensor, computer, phone such as a smart phone, dedicated device, and/or a tablet PC through which that the user may interfaces to provide input response to the testing stimuli. The user device 808 may also include an processor and memory storing instructions that when executed by the processor generate display of a GUI for interaction by the user. The user device 808 may include a memory, a transceiver (XVR) for transmitting and receiving signals, and input/output interface for connecting wired or wirelessly with to a vision correction framework 810, which may be stored on a image processing device. The vision correction framework 810 may be stored on the spectacle device, on the user device, etc.—although in the illustrated example the framework 810 is stored on an external image processing device. The framework 810 receives testing mode information from the testing module 802 and user input data from the user device 808.

Figure 9:
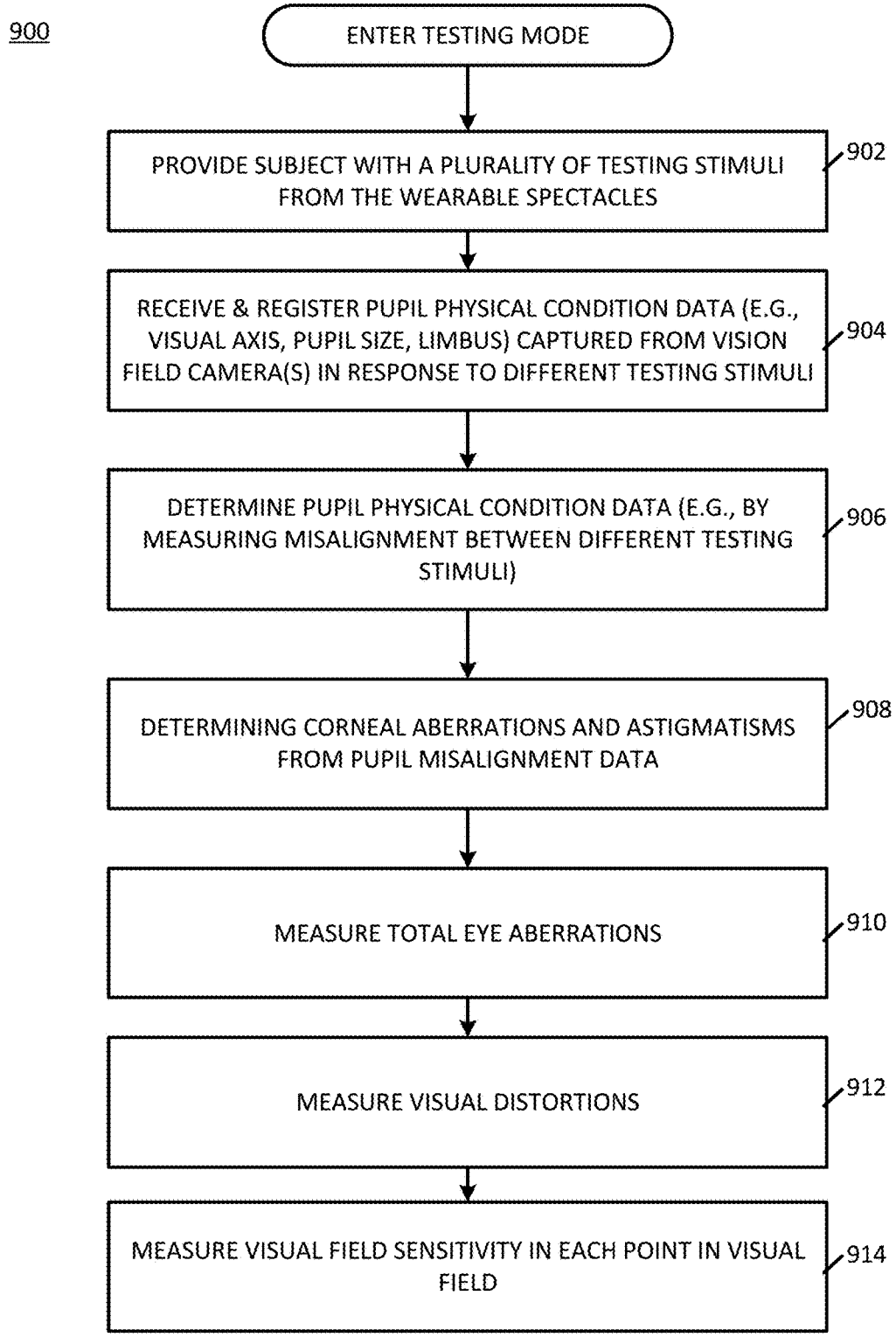
FIG. 9 illustrates a testing mode process according to various embodiments described herein.

FIG. 9 illustrates a testing mode process 900, as may be performed by the workflow 800. At a block 902, a subject is provided a plurality of testing stimuli according to a testing mode protocol. That stimuli may include images of text, images of objects, flashes of light, patterns such as grid patterns. The stimuli may be displayed to the subject or projected onto the retina and/or cornea of the subject. At a block 904, a vision correction framework may receive detected data from one or more inward directed image sensors, such as data corresponding to a pupil physical condition (e.g., visual axis, pupil size, and/or limbus). The block 904 may further include receiving user response data collected from the user in response to the stimuli. At a block 906, the pupil position condition may be determined across different stimuli, for example, by measuring position differences and misalignment differences between different stimuli.

At a block 908, astigmatism determinations may be made throughout the field of vision, which may include analysis of pupil misalignment data and/or eye aberrations (e.g., projecting references images on the retina and cornea and comparing the reflected images from the retinal or corneal surfaces to reference images).

At a block 910, total eye aberrations may be determined, e.g., by projecting reference images onto the retina and/or cornea and then comparing the reflected images from the retinal or corneal surfaces to reference images (see, e.g., FIGS. 31A, 32-34 and accompanying discussion.

At a block 912, visual distortions, such as optical distortions such as coma, astigmatism, or spherical aberrations or visual distortions from retinal diseases, may be measured throughout the field of vision.

At a block 914, the visual field sensitivity may be measured throughout the field of vision.

In various embodiments of the process of FIG. 9, one or more of blocks 904-914 may be optional.

Figure 10:
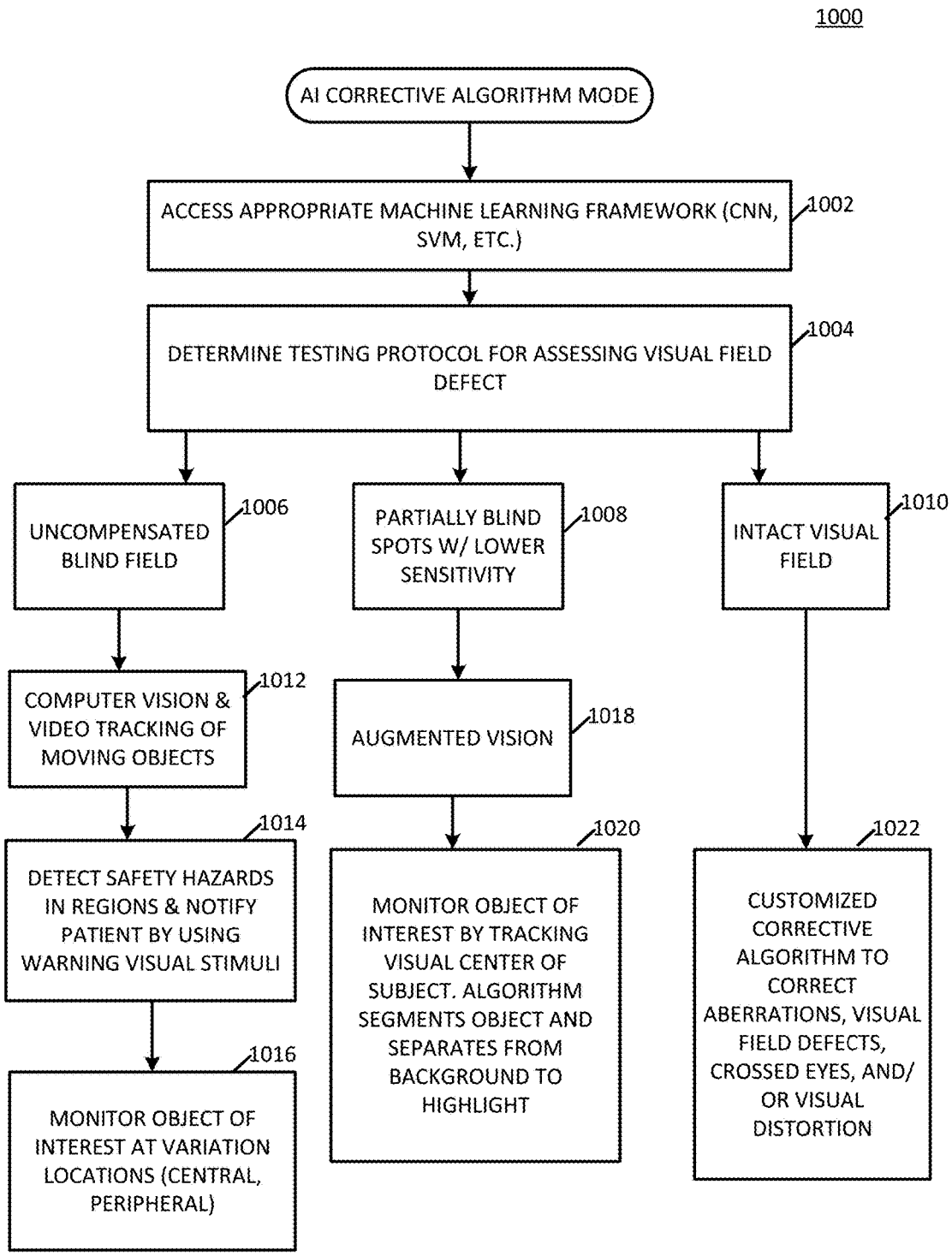
FIG. 10 illustrates a process for an artificial intelligence corrective algorithm mode that may be implemented as part of the testing mode according to various embodiments described herein.

In some examples, the vision systems herein can assess the data from the testing mode and determine the type of ocular anomaly and the type of correction needed. For example, FIG. 10 illustrates a process 1000 comprising an artificial intelligence corrective algorithm mode that may be implemented as part of the testing mode. A machine learning framework is loaded at a block 1002, example frameworks may include, dimensionality reduction, ensemble learning, meta learning, reinforcement learning, supervised learning, Bayesian, decision tree algorithms, linear classifiers, unsupervised learning, artificial neural networks, association rule learning, hierarchical clustering, cluster analysis, deep learning, semi-supervised learning, for example.

At a block 1004, a visual field defect type is determined. Three example field defects are illustrated: uncompensated blind field 1006, a partially blind spot with lower sensitivity 1008, and an intact visual field 1010. The block 1004 determines the visual field defect and then applies the appropriate correction protocol for the visioning mode. For example, for the uncompensated blind field 1006, at a block 1012, a vision correction framework tracks vision, such as through pupil tracking using inward directed image sensors and does video tracking of a moving object in the vision field, e.g., through outward directed image sensors such as external cameras. In the illustrated example, at a block 1014, safety hazards in regions of blind spots or that are moving into the regions of blind spots are detected by, for example, comparing the position of the safety hazard to a mapped vision field with defects as measured in the testing mode. At a block 1016, an object of interest may be monitored at various locations including a central location and a peripheral location.

In the example of a partially blind spot 1008, an augmented vision visioning mode may be entered at a block 1018, from which an object in the vision field is monitored by tracking a central portions of the vision field. At a block 1020, an image segmentation algorithm may be employed to separate the object from the vision field. An augmented outline may also be applied to the object and displayed to the user wherein the outline coincides with identified edges of the segmented object.

With respect to the intact vision field 1010, at a block 1022, a customized corrective algorithm may be applied to correct aberrations, visual field detects, crossed eyes, and/or visual distortion.

In exemplary embodiments, artificial intelligence (AI) may be used for testing mode and/or visioning mode. For example, the techniques may be built upon recognition that methods for image warping (transformation, translation and resizing) to improve visual field produce hundreds of different possible corrective profiles. Almost similar to a fingerprint, every patient's visual field defect is different. In some visual field defects, some image warping has been found to be acceptable to patients while others have not. Some image warping improves the visual field but decrease the central vision (e.g. minification in the center). Therefore, AI algorithms have been developed to address the varied conditions.

In an example, a vision correction framework having a machine learning framework with an AI algorithm may be used to create automatic personalized corrective profiles by applying transformation, translation, and resizing of the field of view to better fit it to the remaining functional visual field. The machine learning framework may include one or more of data collection, visual field classification, and/or regression models. To facilitate recording of participant responses, quantitative scores, and feedback, a graphical user interface (GUI) and data collection program may be used.

Figure 13:
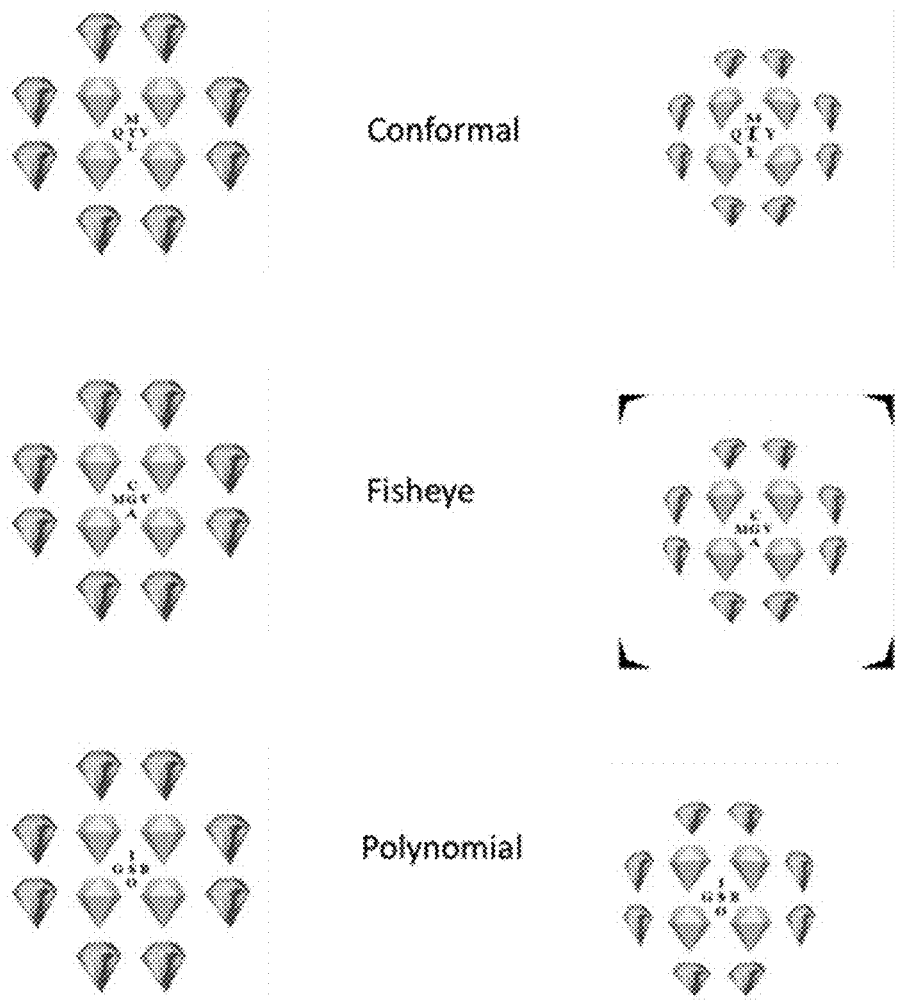
FIG. 13 illustrates examples of different correction transformations that may be applied to an image and presented to a subject according to various embodiments described herein.

With respect to transformations applied to images in the visioning mode, example transformations of the machine learning framework may include one or more of: 1) conformal mapping, 2) fisheye, 3) custom 4th order polynomial transformation, 4) polar polynomial transformation (using polar coordinates), or 5) rectangular polynomial transformation (using rectangular coordinates) (see, e.g., FIG. 13).

With respect to translations applied to images in the visioning mode, examples may include one or more of the following. For the center detection, weighted averaged of the best center and the closest point to the center may be used. For example, the closest point may be determined by finding the nearest point to the center location. The best center may be determined by one or more of the following: 1) the centroid of the largest component, 2) the center of the largest inscribed circle, square, rhombus, and/or rectangle, or 3) the center of the local largest inscribed circle, square, rhombus, and/or rectangle (see, e.g., FIG. 14). For example, the framework may search for the largest shape but alliteratively to avoid getting far from the macular vision region, the framework may substitute this by the weighted average of the closest point with the methods.

In various embodiments, the AI algorithm may be initially trained using simulated visual field defects. For example, to train the AI algorithm, a dataset of visual field defects may be collected. For example, in one experimental protocol a dataset of 400 visual field defects were obtained from patients with glaucoma. The dataset may be used to create simulated visual field defects on virtual reality glasses for presentation to normal subjects for grading. The resulting feedback obtained from the grading may then be used to train the algorithm.

For example, an AI algorithm that automatically fits an input image to areas corresponding to the intact visual field pattern for each patient individually may be used. In various embodiments, the algorithm may include at least three degrees of freedom to remap the images, although more or less degrees of freedom may be used. In one example, the degrees of freedom include transformation, shifting, and resizing. The added image transformation may preserve the quality of the central area of the image corresponding to the central vision, where acuity is highest, while condensing the peripheral areas with an adequate amount of image quality in the periphery. This may be applied such that the produced overall image content would be noticeable to the patient.

The image transformations included in the AI algorithm may include one or more of conformal, polynomial or fish eye transformations. In some embodiments, other transformations may be used. The machine learning techniques may be trained on a labeled dataset prior to performing their actual task. In one example, the AI algorithm may be trained on a visual field dataset that incorporates different types of peripheral defects. For example, in one experiment, the dataset included 400 visual field defect patterns. The training phase was then guided by normal participants to quantitatively score the remapped images generated by the AI algorithm.

Figure 11:
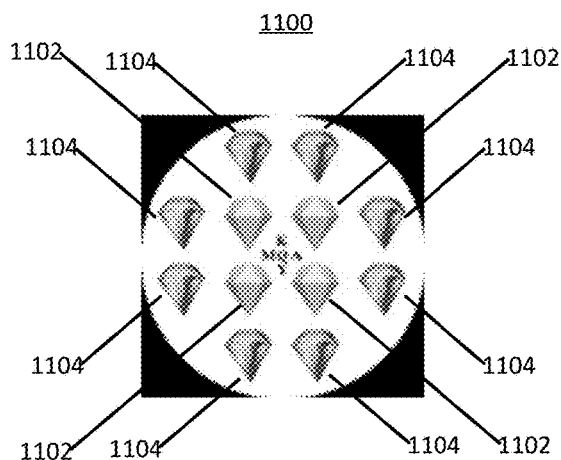
FIG. 11 shows a test image according to various embodiments described herein.

FIG. 11 shows an image 1100 of a test image (stimuli) according to one example. The test image 1100 may be designed to measure the acuity, the paracentral vision and/or the peripheral vision. The illustrated test image displays five letters at the central region, four internal diamonds 1102 at the paracentral region, and eight external diamonds 1104 at the peripheral region as shown in FIG. 11.

Figure 12:
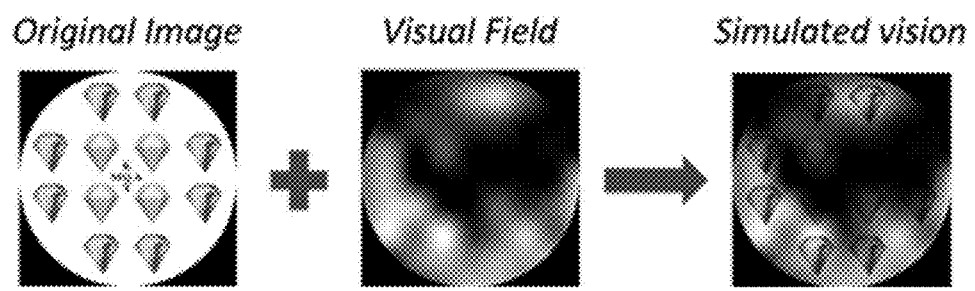
FIG. 12 illustrates development of a simulated vision image including overlaying an impaired visual field on a test image for presentation to a subject according to various embodiments described herein.
Figure 14:
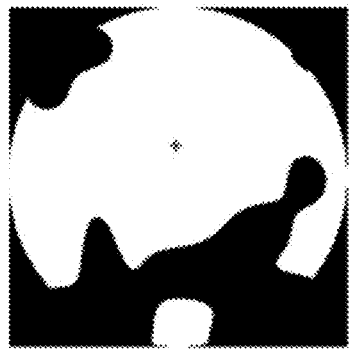
FIG. 14 illustrates example translation methods according to various embodiments described herein.
Figure 14:
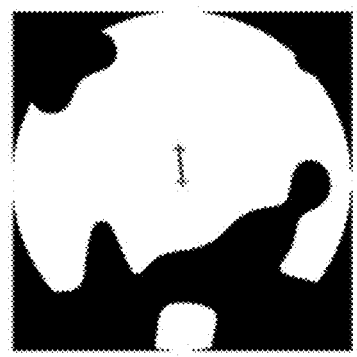
Figure 14:
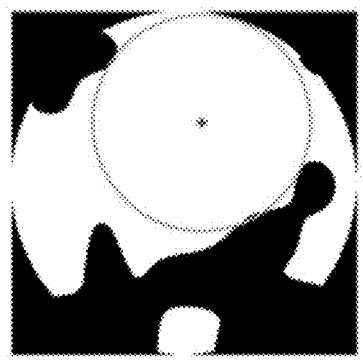
Figure 14:
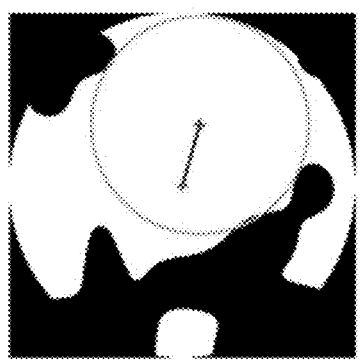
Figure 14:
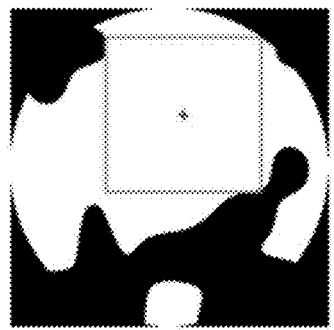
Figure 14:
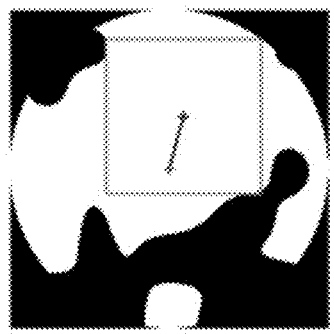

To be able to train the AI system, a volume of data is needed, as introduced above. As an initial step, defective binocular visual fields may be used to simulate binocular vision of patients as shown in FIG. 12. Next, the simulated vision may be presented to subjects through the spectacles device. In this way, the input image can be manipulated using different image manipulations then presented again to the subject to grade the modified vision. The corrected image may be further corrected and presented to the subject in a continually corrective process until an optimized corrected image is determined. FIG. 13 illustrates examples of different correction transformations that may be applied to the image and presented to the user. FIG. 14 illustrates an example of different translation methods (shifting the image to fit it in the intact visual field). The intact visual field is white and blind visual field is black.

Figure 15:
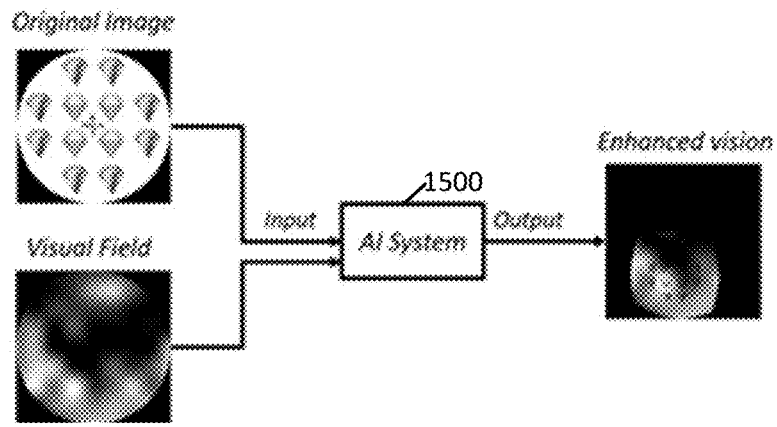
FIG. 15 schematically illustrates an example of a machine learning framework according to various embodiments described herein.

The AI system may be designed using machine learning models such as artificial neural networks and Support Vector Machines (SVM). In some examples, the AI system is designed to produce an output comprising an estimate the best image manipulation methods (i.e. geometric transformation and translation) through an optimization AI system. The vision system, in a visioning mode, may presents images manipulated according to the output image manipulation methods to the patient through a headset such that the patient experiences the best possible vision based on his defective visual field. The machine learning framework (also termed herein "AI System") of the vision correction framework may trained using the collected data, e.g., as described above and elsewhere herein. A block diagram of an example AI system 1500 is shown in FIG. 15.

Figure 17:
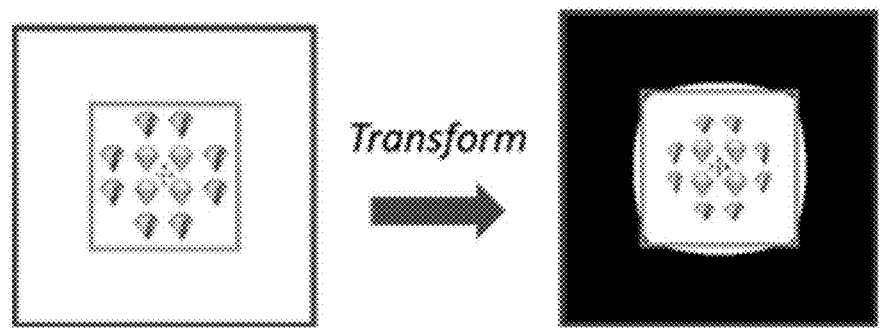
FIG. 17 illustrates an example transformation of a test image according to various embodiments described herein.
Figure 18:
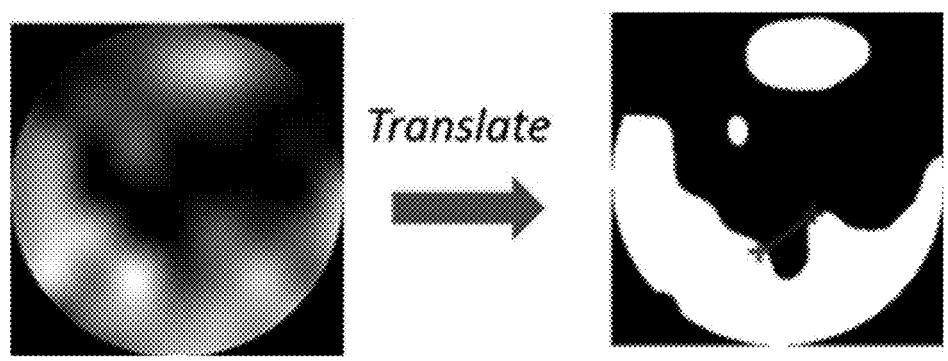
FIG. 18 illustrates an example translation of a test image according to various embodiments described herein.
Figure 19:
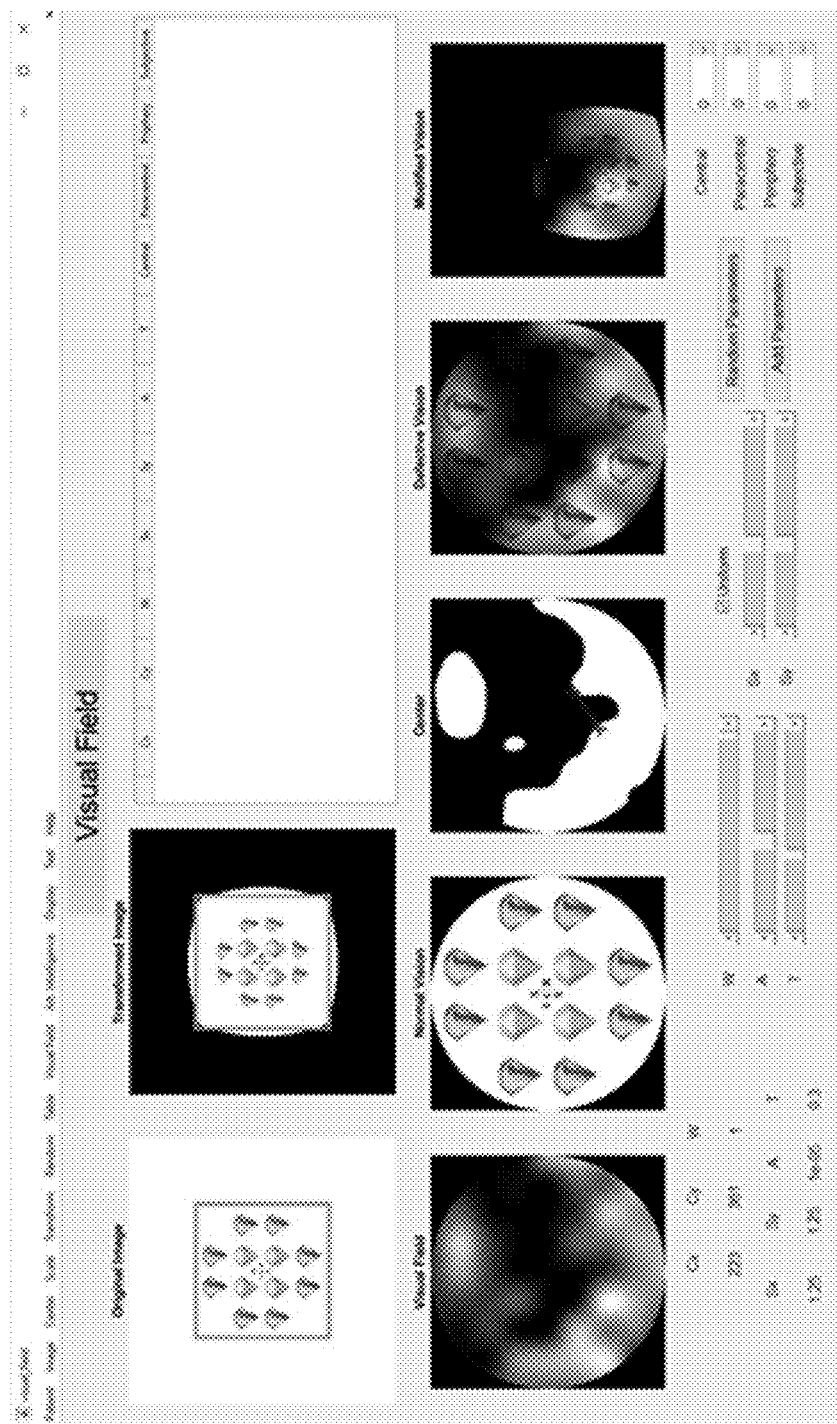
FIG. 19 is a graphical user interface illustrating various aspects of an implementation of an AI system according to various embodiments described herein.

A process 1600 of the AI system 1500 is shown in FIG. 16. The input to the system 1500 includes a test image and a visual field image. The AI system 1500 estimates the best geometric transform for the test image such that more details can be presented through the visual field. Then, AI system 1500 estimates the best translation for the test image such that the displayed image covers major parts of the visual field. Then, the test image is transformed and translated as shown in FIG. 17. and FIG. 18, respectively. Finally, the image is combined with the visual field again in case of the training only for the simulation purpose, but it is displayed directly to the patient in the testing phase. A screenshot of graphical user interface presenting a summary of visual field analysis, which may include a final implementation of the visual field AI system including parameters of the image transformation and translation to be applied to the image, is shown in FIG. 19.

Figure 20:
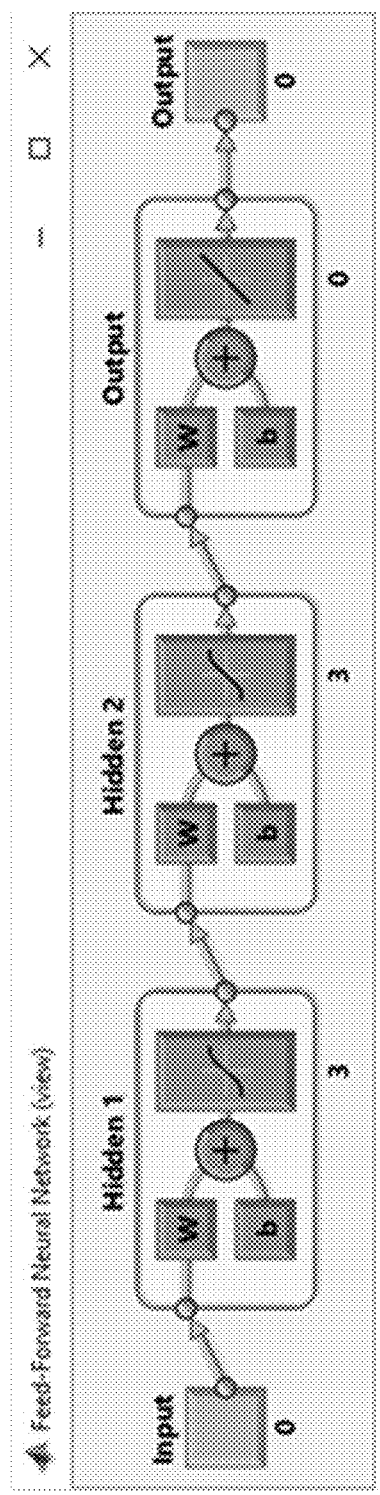
FIG. 20 schematically illustrates a framework for an AI system including a feed-forward neural network according to various embodiments described herein.
Figure 21:
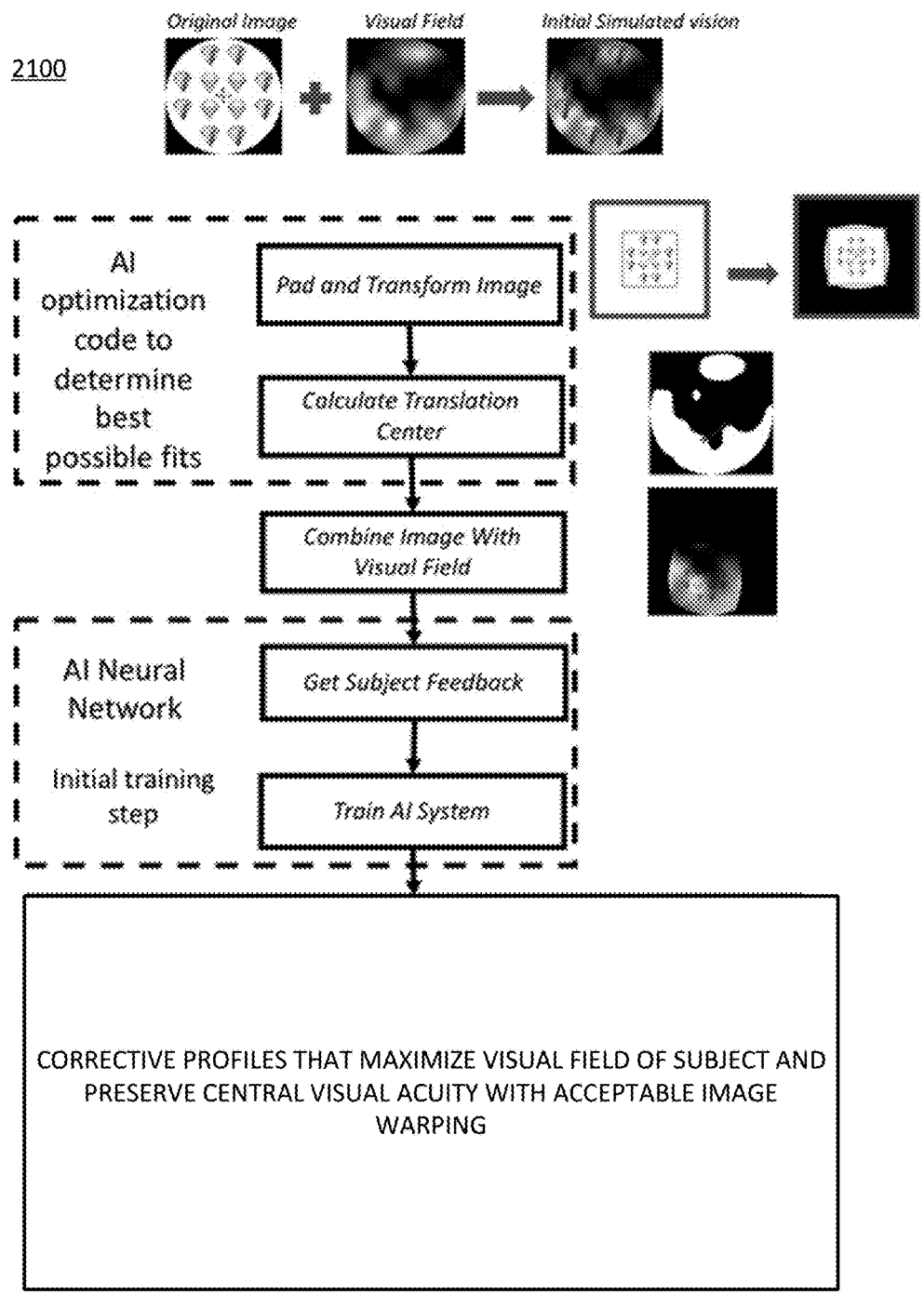
FIGS. 21 & 22 illustrate example testing mode processes of an AI system including an AI neural network and an AI algorithm optimization process, respectively, according to various embodiments described herein.
Figure 22:
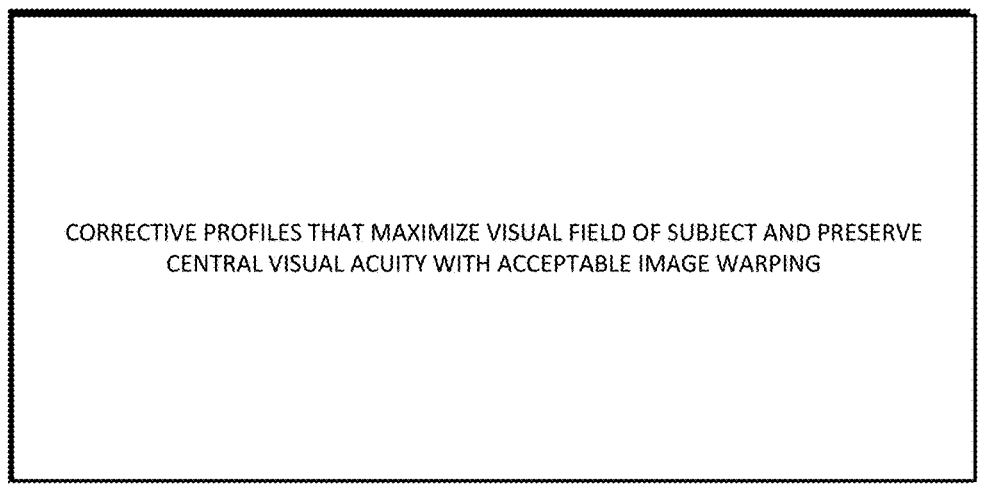
Figure 22:
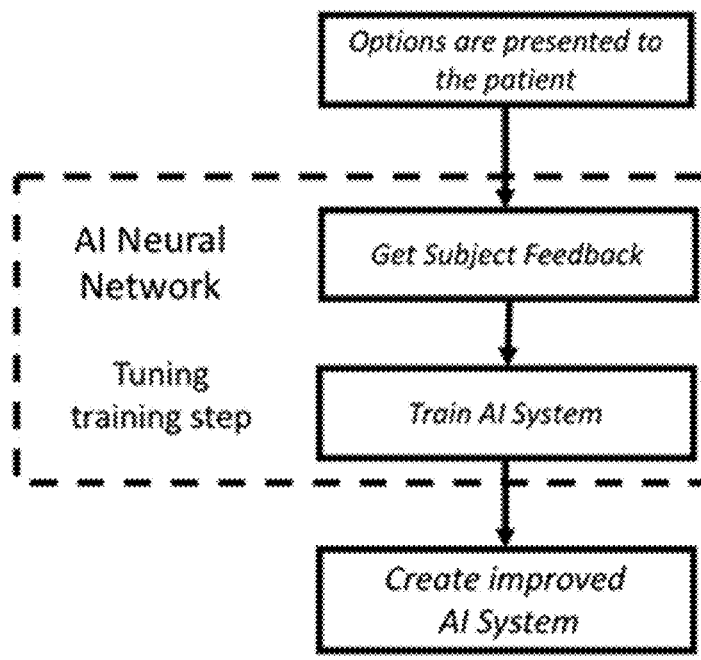

In example an implementation, an artificial neural network model was used to implement the machine learning framework ("AI system") on the vision correction framework. The AI system takes as the visual field image converted to a vector. The AI system gives as output the prediction of the parameters of the image transformation and the translation to be applied to the scene image. Then, the scene image is manipulated using these parameters. The AI system includes two hidden layers wherein each hidden layer includes three neurons (i.e. units) and one output layer. One such example AI system model is shown FIG. 20. This AI system may also extend to convolutional neural network model for even more accurate results, in other examples. FIGS. 21 and 22 illustrate example processes 2100 and 2200 of a testing mode application of an AI neural network and an AI algorithm optimization process using an AI neural network, respectively.

In various embodiments, the vision system includes a spectacles device and/or an image processing device. Embodiments of the vision system may include the image processing device alone. The image processing device and functionalities thereof, such as those associated with the vision correction framework described herein, may be configured for use with the spectacles devices described herein or with other devices or may be used for diagnosis of conditions and/or processing of enhanced real-time displays, which may or may not be associated with a display of processed image data. For example, in one embodiment, the image processing device may be configured for processing image data for enhancement of a visional field for pilots. The enhanced visual field may be provided to the pilot using a spectacles device described herein, e.g., which may be incorporated into a helmet visor including a single or multiple displays of the enhanced visual field to the pilot. In some examples, the spectacles device are goggles. The enhanced visual field may also be displayed across a windshield or canopy of the aircraft as a display screen or monitor, which may include glass, film, and/or layers wherein their transparency is controllable as described herein.

In any of the above or another example, the image processing device may be configured for processing images with respect to a testing mode and/or visioning mode as described herein (see, e.g., FIGS. 4, 5, 9, 10, 15, 16, 20-23). In some examples, the image processing device may include a vision correction framework configured to perform one or more operations with respect to the testing mode and/or visioning mode (see, e.g., FIGS. 2, 3, 8). In any of the above or another example, the vision correction framework includes a machine learning framework, which may include an AI corrective algorithm (see, e.g., FIGS. 2, 10-23). The vision system may comprise any hardware, software, and/or network configuration described herein (see, e.g., FIGS. 1A-3, 8, 21, 22, 24, 25).

In any of the above or another example, the image processing device may be integrated with the spectacles device. Integration may be full or partial. The image processing device may also be external to the spectacles device, which may be full or partial. In one example, the image processing device and/or vision correction framework may be distributed, e.g., via a network or communication protocol. For example, the image processing device and/or vision correction framework and functionalities thereof may be distributed among two or more of a user device such as a smart phone, laptop, tablet, or dedicated device; the spectacles device such as an onboard processing system; and an external processing system such as a computer, PC, laptop, or server.

As introduced above, the vision system may include spectacles device and an image processing device. Some embodiments may include just the spectacles device or just the image processing device, which may include other associated systems and device.

Figure 23:
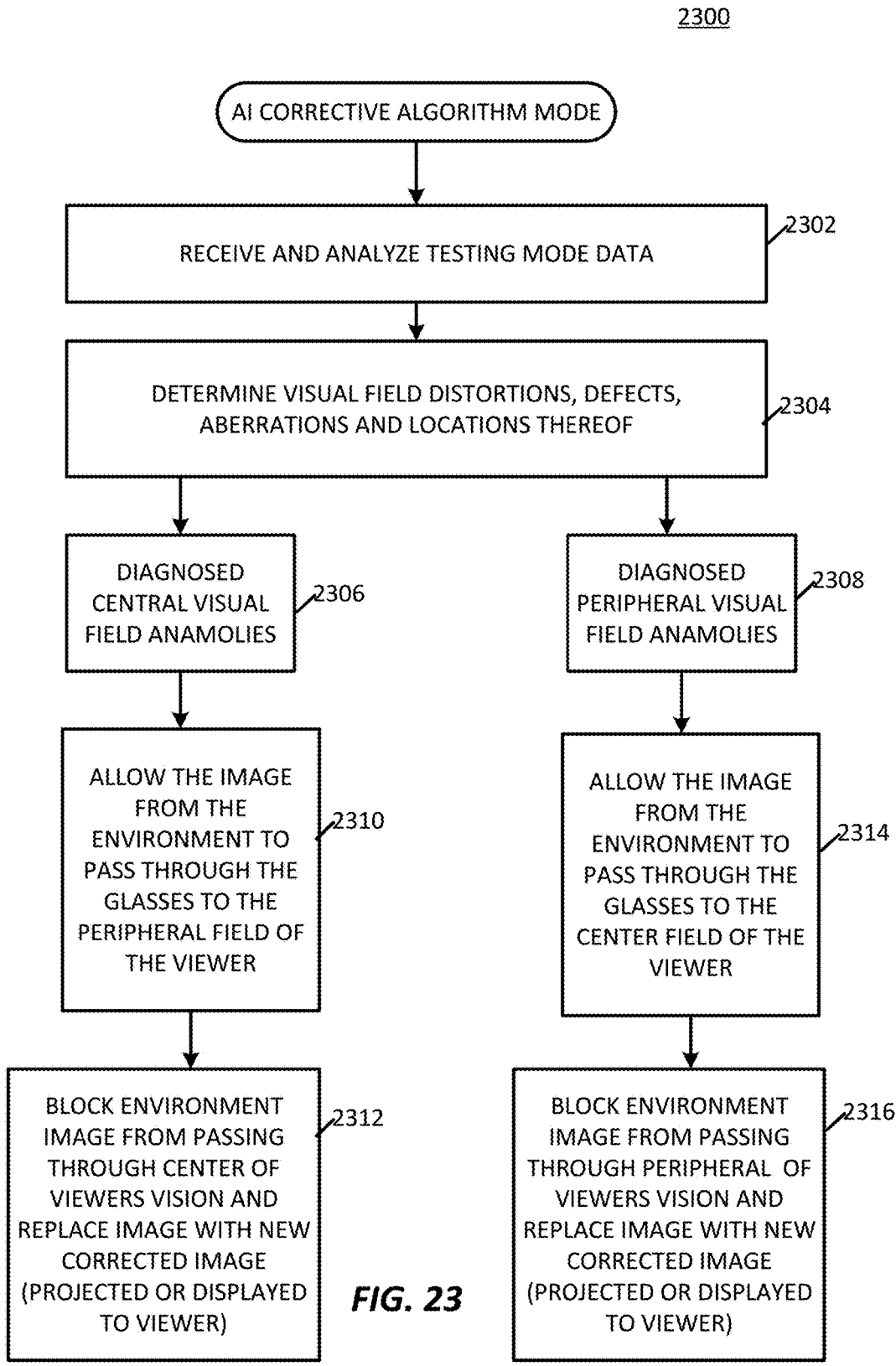
FIG. 23 illustrates an example process implementing testing and visioning modes according to various embodiments described herein.

In any of the above or another example, the spectacles device may be configured to selectively control transparency of a display area of a monitor, such as a screen, glass, film, and/or layered medium. For example, present techniques may be implemented in augmented reality (also termed herein custom reality) spectacles device. FIG. 23 illustrates an example process 2300 implementing testing and visioning modes. In an example, custom-reality spectacles device may use a macular (central) versus peripheral vision manipulation.

In some examples of custom reality spectacles device (see, e.g., FIGS. 40A-40C) include transparent glasses for overlaying corrected images onto a visible scene. The glasses may comprise a monitor comprising a screen having controllably transparency onto which images may be projected for display. In one example, the display comprises a heads-up display. In various embodiments, a custom reality spectacles device includes glasses having controllable layers for overlaying corrected images onto a scene visible through the glasses. The layers may comprise glass, ceramic, polymer, film, and/or other transparent materials arranged in a layered configuration. The controllable layers may include one or more electrically controlled layers that allow for adjusting the transparency over one or more portions of the visual field, for example, in pixel addressable manner. In one embodiment, may include pixels or cells that may be individually addressable, e.g., via an electric current, field, or light. The controllable layers may be layers that may be controlled to adjust contrast of one or more portions of the visual field, color filtering over portions, the zooming in/zooming out of portions, focal point over portions, transparency of the spectacles device surface that display the image to block or allow the light coming from the environment at a specific location of the visual field. If there is a portion of field of view (e.g., a portion of the peripheral vision or a portion of the macular vision or a portion, part of it is macular and part of it is peripheral) for manipulation to augment a subject's vision, then the transparency of that portion of the glass may be lowered to block the view of the environment through that portion of glass and to allow the patient to see more clearly the manipulated image displayed along that portion of the glass. In various embodiments, vision system or custom reality spectacles device may dynamically control transparency regions to allow a subject to naturally view the environment when redirecting eyes by eye movement rather than just head movement. For example, pupil tracking data, e.g., pupil and/or line of sight tracking, may be used to modify the portion of the glass having decreased transparency such that the decreased transparency region translates relative to the subject's eye.

Figures 40A, 40B, 40C:
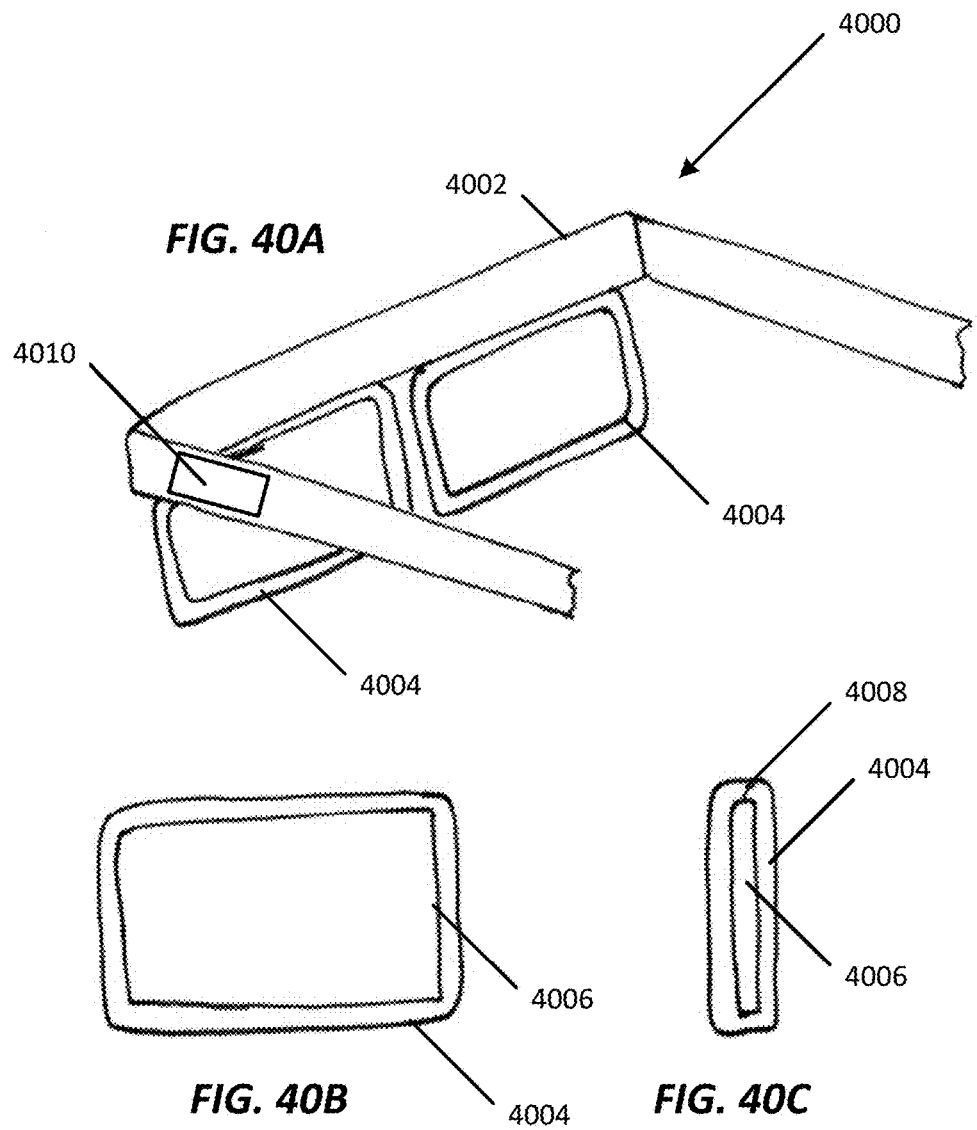
FIGS. 40A-40C illustrates an example custom reality spectacles device according to various embodiments described herein.

For example, the transparency of the glass in the spectacles device comprising custom-reality glasses may be controllably adjusted to block light from that portion of the visual field corresponding to where image correction is performed, e.g., at a central region or a peripheral region. Otherwise subject may see the manipulated image and see through it and perceive the underling actual visual field in that region. Such light blocking can be achieved by a photochromic glass layer within the spectacles device. Moreover, the spectacle device may change the position of the area where the glass transparency is reduced by measuring for eye (pupil) movement using inward directed image sensors, and compensating based on such movement by processing in the vision correction framework. In one example, the display screen of the monitor includes pixels or cells including electric ink technology and that may be individually addressed to cause an electric field to modify the arrangement of ink within a cell to modify transparency and/or generate a pixel of the display. In an example implementation, FIG. 40A shows custom-reality glasses 4000 formed for a frame 4002 and two transparent glass assemblies 4004. As shown in FIGS. 40B and 40C, the transparent glass assemblies 4004 have embedded, electronically controllable correction layers 4006 that may be controllable from fully transparent to fully opaque, that may be digital layers capable of generating a correction image to overlay or supplant a portion of the field of view of the glasses 4004. The correction layers 4006 may be connected, through an electrical connection 4008, to an image processing device 4010 on the frame 4002.

With specific reference to the process 2300 of FIG. 23, at a block 2302 testing mode data may be received by a vision correction framework, and at a block 2304 visual field distortions, defects, aberrations, and/or other ocular anomalies may be determined, along with their locations.

Figure 24:
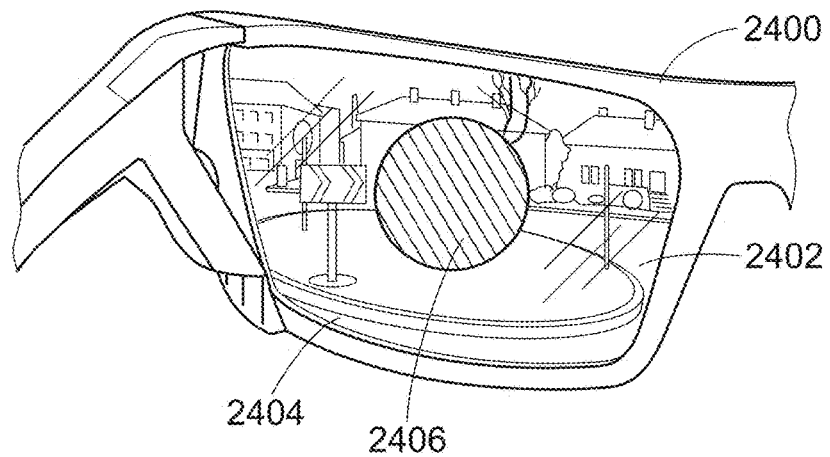
FIG. 24 illustrates a wearable spectacles device comprising custom reality wearable spectacles that allow an image from the environment to pass through a portion thereof wherein a peripheral field of a viewer is allowed to pass through and a central region is blocked according to various embodiments described herein.
Figure 25:
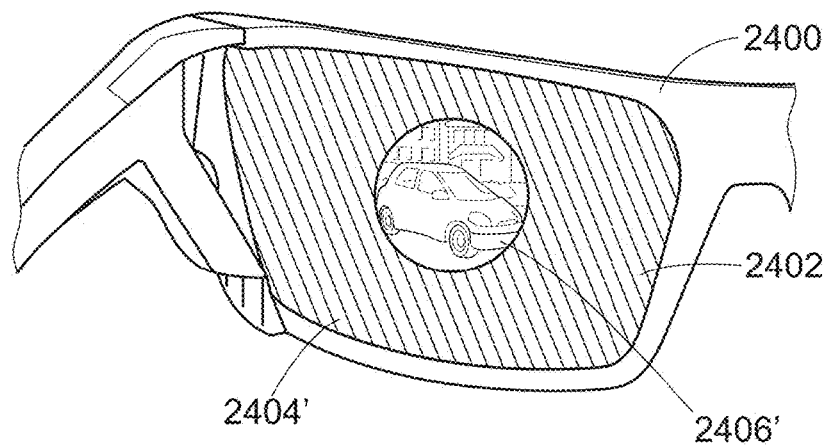
FIG. 25 illustrates a wearable spectacles device comprising custom reality wearable spectacles that allow an image from the environment to pass through a portion thereof wherein a central region of a viewer is allowed to pass through and a peripheral field region is blocked according to various embodiments described herein.

For diagnosed central vision field anomalies 2306, at a block 2308 the custom reality spectacles device may allow the image from the environment to pass through the glass thereof to a peripheral field of the viewer, e.g., as shown in FIG. 24. As shown, custom reality spectacles device 2400 may have a multi-layered glass viewfinder 2402. A peripheral region 2404 may be set as transparent to allow light passage there through, allowing the subject to view the actual un-corrected environment. At a block 2312, a central region 2406 of the environment may be blocked by the spectacles device 2400 and a corrected rendition of the central region may be presented by display to the user, for example, using corrections such as those of FIGS. 13, 14, 17, and 18.

For diagnosed peripheral visual field anomalies 2308, at a block 2314 a central region 2406' (see, FIG. 25) of the environment is allowed to pass through a transparent portion of the spectacles device 2400, and transparency of a peripheral region 2404' is modified to block such that a corrected peripheral version image may be displayed within peripheral region 2404', for example using the corrective transformations herein.

In other examples, the present techniques may be used to capture and enhance a binocular visual field, which may then be applied to both eyes to provide a subject with a corrected (or in some instances an enhanced) field of view. FIGS. 26-30 illustrate examples of binocular visual field expansion techniques.

Figure 26:
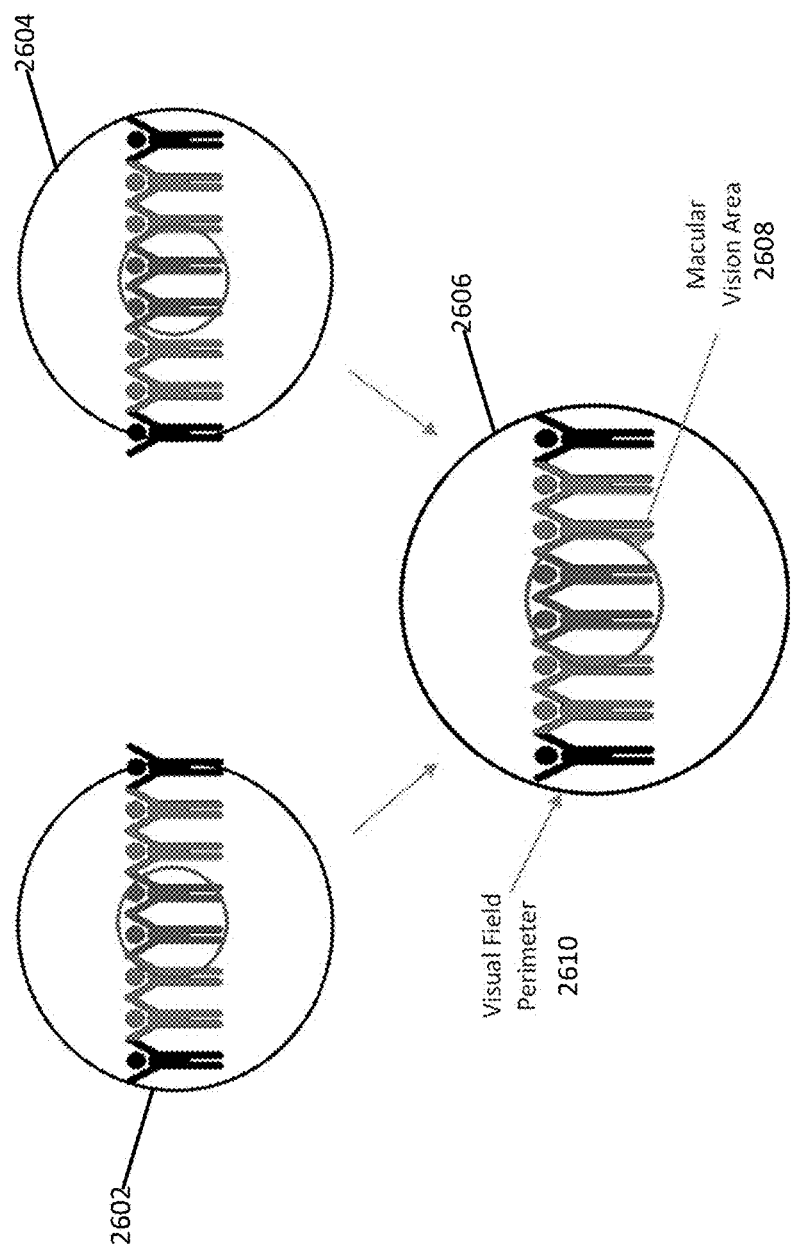
FIG. 26 illustrates a normal binocular vision for a subject where a monocular image from the left eye and from the right eye are combined into a single perceived image having a macular central area and a peripheral visual field area surrounding the central area.

FIG. 26 illustrates a normal binocular vision for a subject where a monocular image from the left eye 2602 and from the right eye 2604 are combined into a single perceived image 2606 having a macular central area 2608 and a peripheral visual field area 2610 surrounding the central area 2608. In some cases, however, a subject may have a tunnel vision condition, wherein the peripheral area 2610 is not visible to the subject, as in FIG. 27. As shown, for these cases, one or more objects do not appear within a field of view, resulting in a peripheral defect 2612 in the area 2610 where objects within the area 2610 are not seen by the patient.

Figure 27:
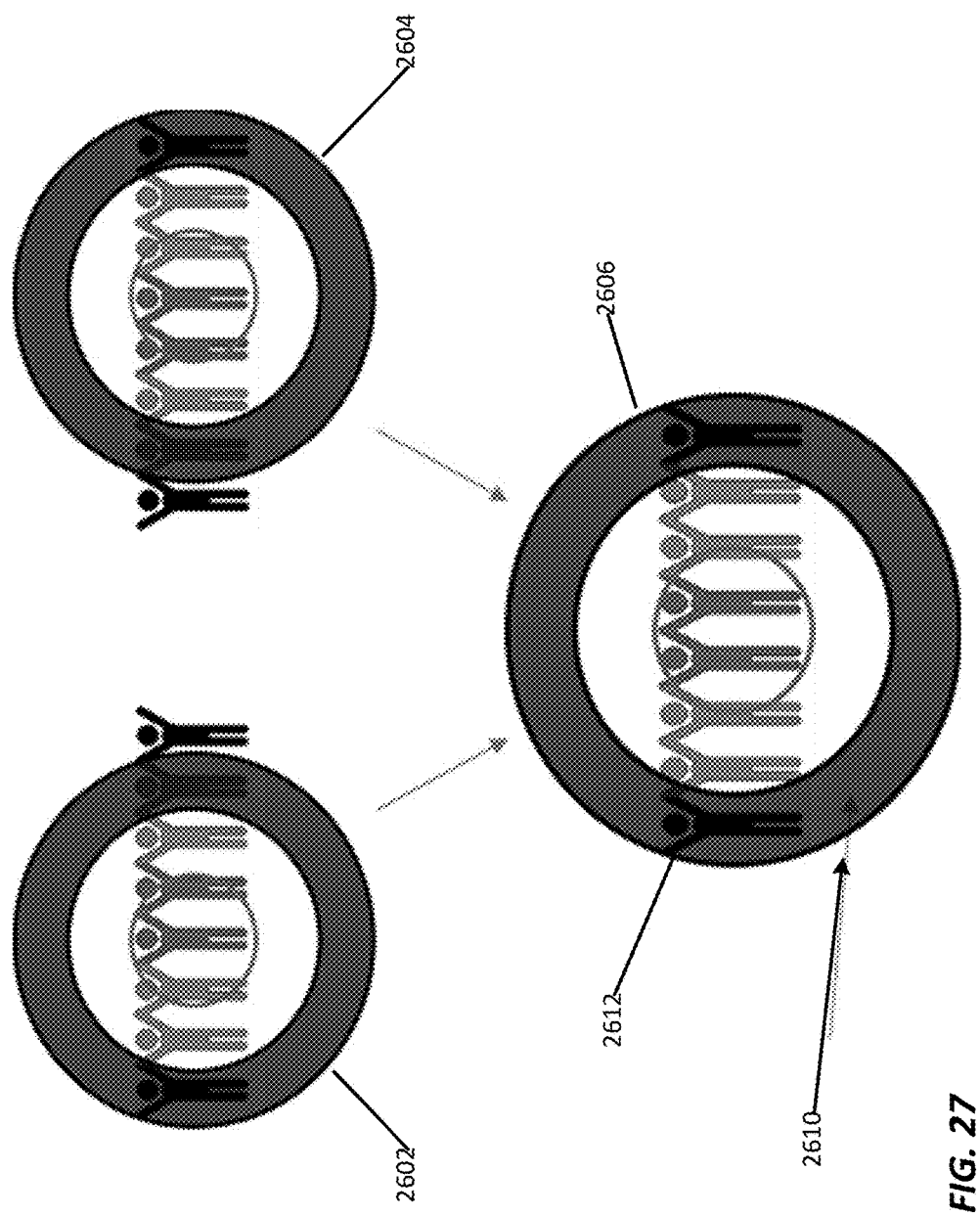
FIG. 27 illustrates a tunnel vision condition wherein a peripheral area is not visible to a subject.
Figure 28:
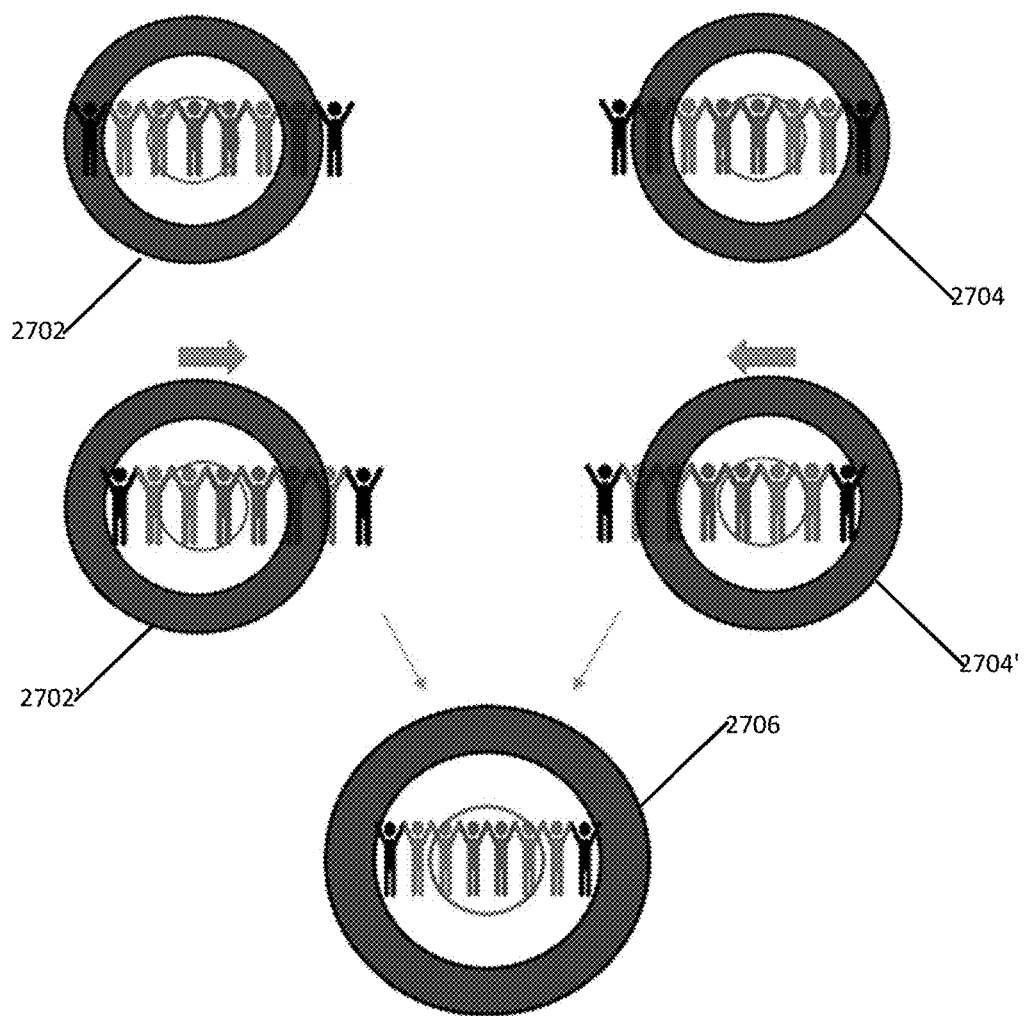
FIG. 28 illustrates an image shifting technique to enhance vision or to correct a tunnel vision condition according to various embodiments described herein.

In some examples, the defect in FIG. 27 may be corrected using a shifting image correction technique. As demonstrated in FIG. 28. Each visual field camera captures a monocular image 2702 and 2704, respectively, where each monocular image is different as it's capturing the visual scene from a slightly different (offset) position. The two captured monocular images 2702, 2704 are then shifted toward each other in the visual correction framework resulting in images 2702' and 2704'. These two shift images are then combined to generate a binocular image 2706 that captures the full periphery of the visual scene. For spectacles device having monitor displays, each display may display the corrected binocular image 2706 to the subject. In an example, as we demonstrated, this shifting transformation can increase the field of view of a subject by 5%, 10%, 15% or 20%, without producing double vision effects for the patient.

Figure 29:
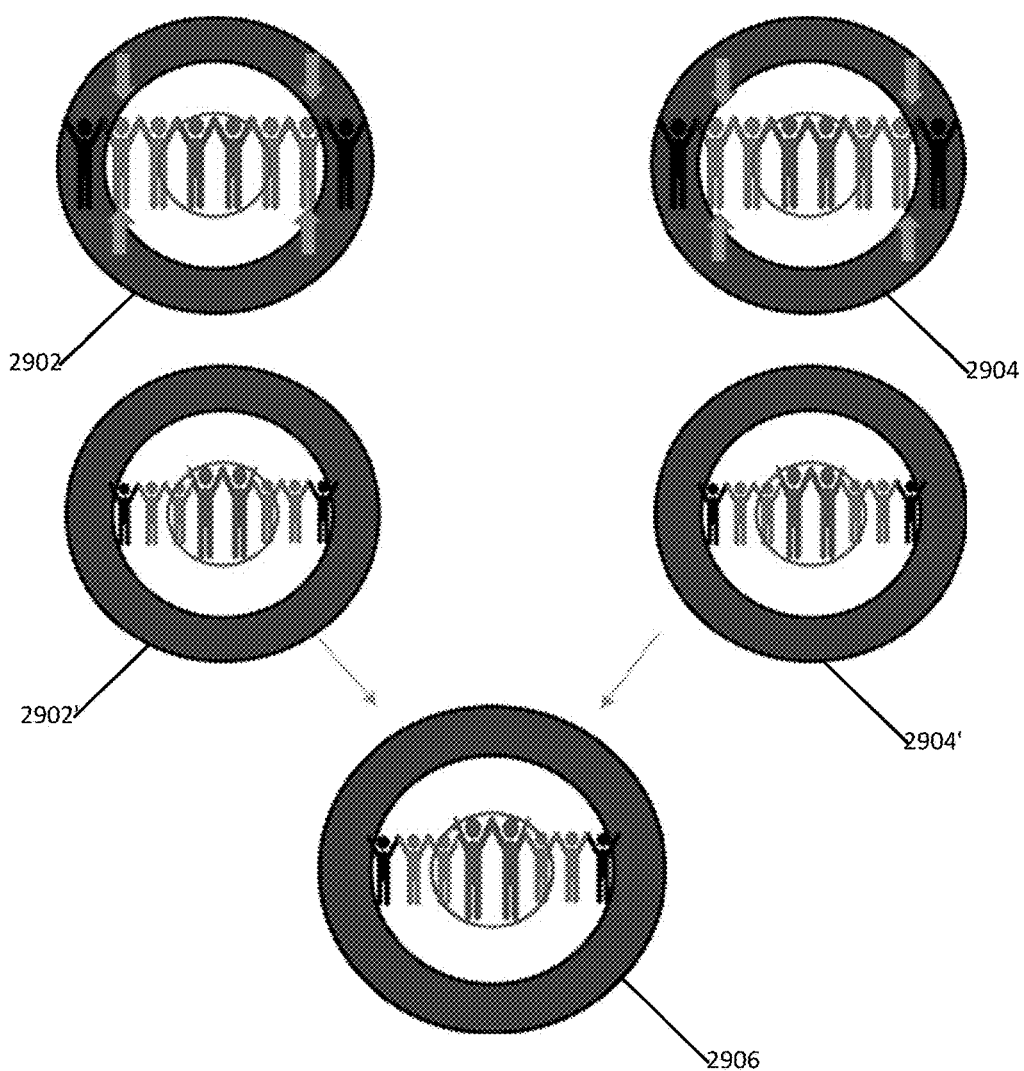
FIG. 29 illustrates an image resizing transformation technique to enhance vision or preserve central visual acuity while expanding the visual field according to various embodiments described herein.

FIG. 29 illustrates another binocular visual field correction process. In this example, captured monocular images 2902 and 2904 are resized, for example, only in peripheral areas, while keeping the macular central area (central 20 degrees) unchanged, resulting in corrected images 2902', 2904'. Such resizing transformation will preserve the visual acuity in the center while expanding the visual field. A combined binocular image 2906 captures the objects in the periphery that were missed before, and at the same time, keeps the details of the central macular area, as shown. The peripheral objects are clearly noticed by the subject even after resizing them, as the peripheral vision is not as sensitive as the central one. In an example, we demonstrated that shrinking of up to 20% of the image size can be performed without producing double vision effects for the patient. In various embodiments, the system may perform resizing of a peripheral region additionally or alternatively to resizing of a central area. For example, peripheral regions may be reduced in size while retaining the size of the macular central area, e.g., for glaucoma patients.

For macular degeneration, we can do the opposite. Leave the peripheral vision intact and enlarge the central.

Figure 30:
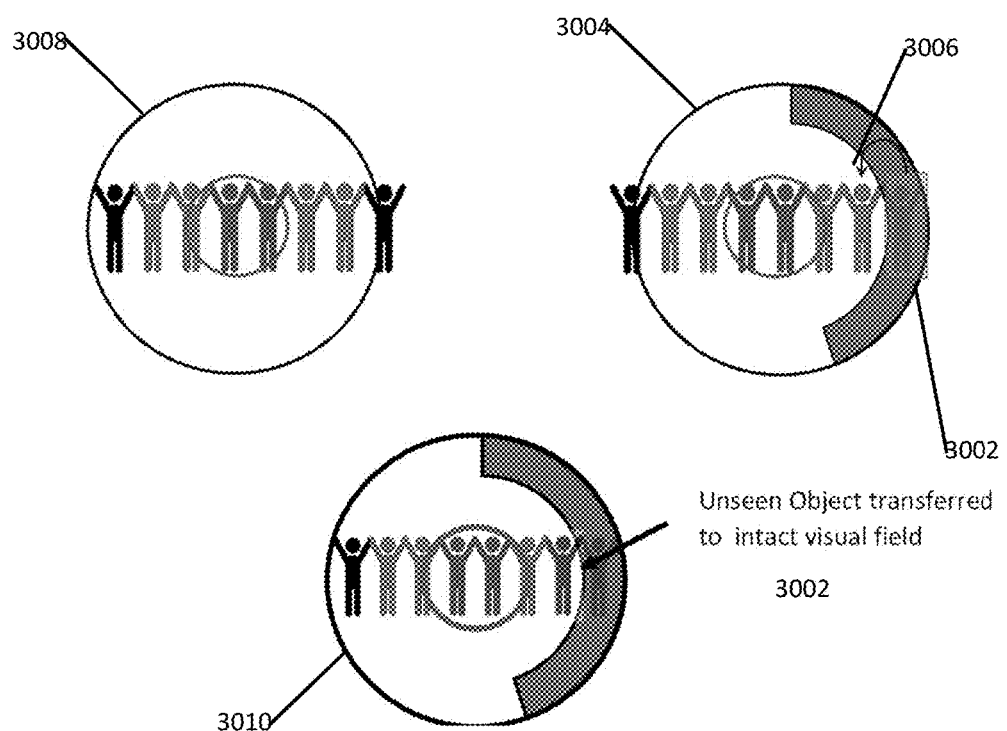
FIG. 30 illustrates a binocular view field expansion technique according to various embodiments described herein.

FIG. 30 illustrates another binocular visual field correction process. For patients with far peripheral defect in one eye, a missing object 3002 in a vision field 3004 of the defective eye can be transferred digitally to a mid peripheral field region 3006 of the vision field 3004, while other vision field 3008, that of the healthy eye, would otherwise cover this area, meaning that the combined binocular image 3010 displays the missing object 3002 within an intact vision field. The subject may notice visual confusion in the area, but the subject can adapt to isolate information in this area of the visual field according to a moving object or the changing environment.

Figure 31A:
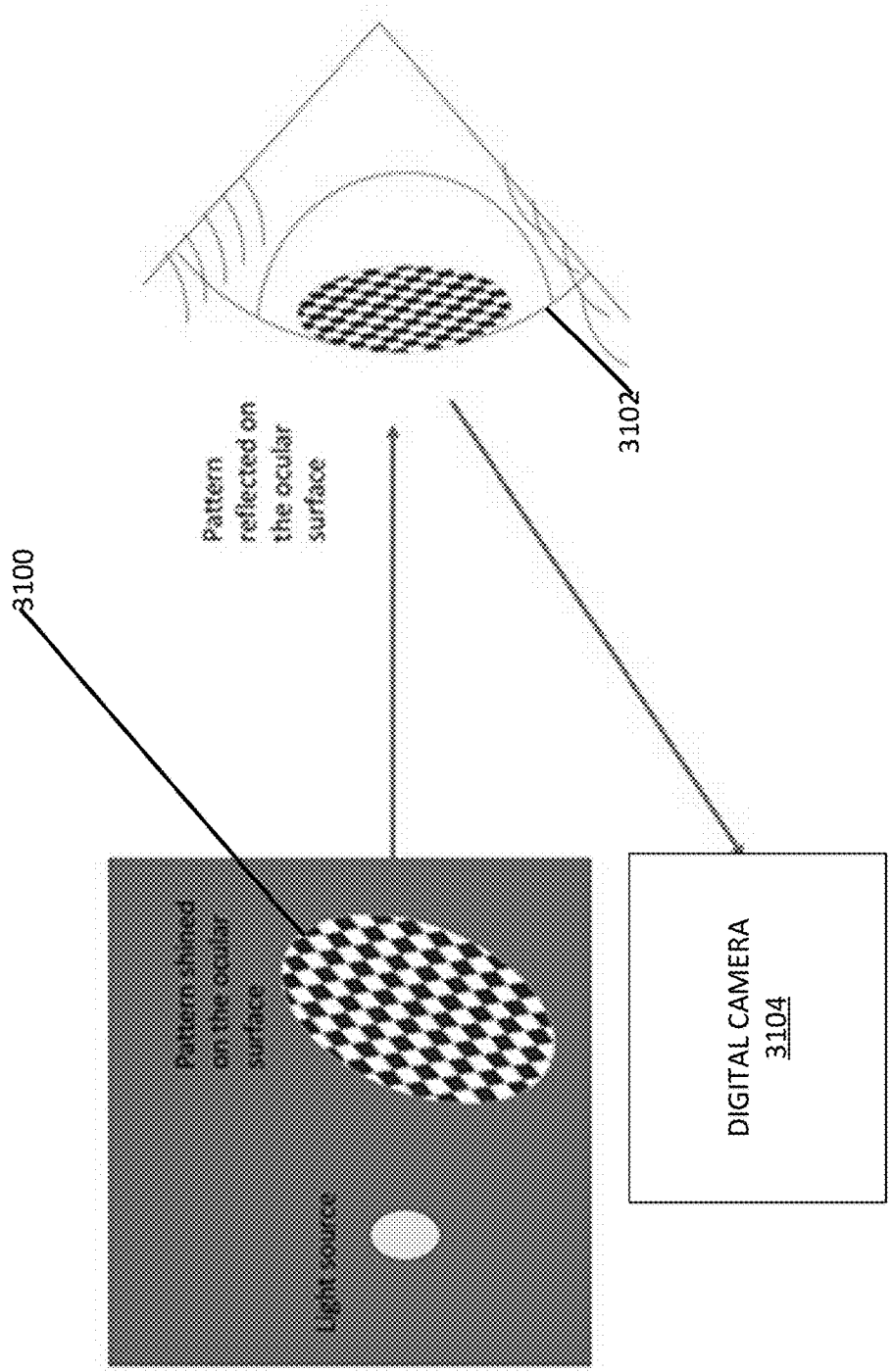
FIG. 31A illustrates a technique for assessing dry eye and corneal irregularities including projecting a pattern onto the corneal surface and imaging the corneal surface reflecting the pattern according to various embodiments described herein.
Figure 34:
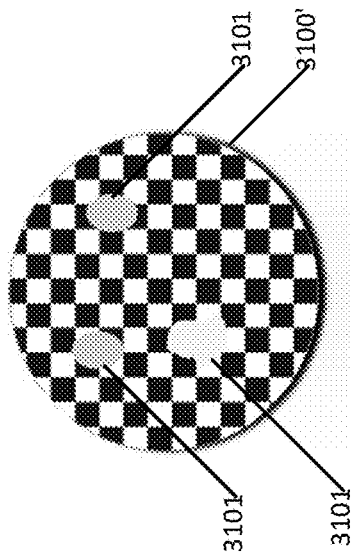
FIG. 34 illustrates an example of an abnormal pattern reflection according to various embodiments described herein.
Figure 32:
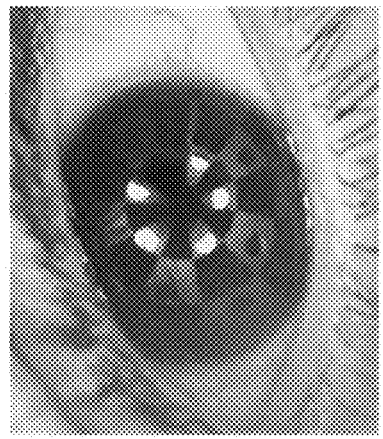
FIG. 32 is an image of a corneal surface reflecting a pattern projected onto the corneal surface according to various embodiments described herein.
Figure 33:
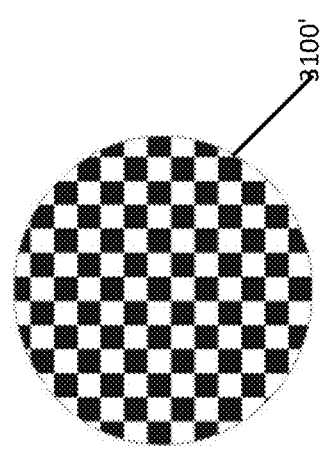
FIG. 33 illustrates an example of a normal pattern reflection according to various embodiments described herein.

In various examples of the testing mode, a pattern may be projected onto the retina, using a projection-based wearable spectacle. The pattern can be used to determine defects directly on the retina, as well as defects affecting the cornea. In an example, the projection pattern can be used to assess correct for dysmorphopsia in age related macular degeneration and other retinal pathologies. As shown in FIG. 31A, a digital projection of a pattern 3100 may be projected onto a subjects eye 3102. The pattern may be digitally generated on a projector positioned on an interior of the spectacles device. A digital camera 3104, such as an inward directed image sensor, which may also be positioned on an interior side of the spectacle device to capture an image of the pattern 3100 reflected from the eye 3102. That image capture may be, for example, captured from the corneal surface of the eye, as shown in FIG. 32. From the captured image of the pattern 3100', the vision correction framework may determine if the pattern looks normal, e.g., as depicted in FIG. 33 or exhibits anomalies, e.g., such as depicted in FIG. 34 (3101). The anomalies may be assessed and corrected for using one of the techniques described herein.

In some examples, the pattern 3100 may be a grid such as an Amsler grid or any known reference shape designed to allow for detecting a transformation needed to treat one or more ocular anomalies. That transformation may then be used to reverse-distort the image in real-time to allow better vision. For example, this technique may be employed using a virtual reality model or an augmented reality model. In an example implementation of FIG. 8, a vision system 800 may include a testing module 802. The testing module 802 may be associated with wearable spectacles or may be executed in combination with an external device as described elsewhere herein. The testing module 802 may present testing stimuli comprising an Amsler grid to a subject 806. The subject, via the user device 808 or other input device, may manipulate the image of the grid to improve distortions. The visual correction framework 810 may present the Amsler grid for further correction by the subject. When the subject has completed their manual correction, the vision correction framework 810 may generate the correction profile of the subject to apply to visual scenes when they are using the spectacles device. The described workflow of vision system 800 may similarly be applicable to other testing mode operations described herein.

FIG. 31B is a schematic illustration of the presentment of an Amsler grid 3100 (i.e., an example reference image) displayed as an image on a wearable spectacle (e.g., VR or AR headset). The Amsler grid 3100 may be displayed to or projected onto a cornea and/or retina of the subject. An example standard grid 3100 is shown in FIG. 31C. The same grid pattern may be displayed on a user device. The subject may manipulate the lines of the grid pattern, particularly the lines that appear curved, utilizing a keyboard, mouse, touch screen, or other input on a user device, which may include a user interface. The subject can specify an anchor point 3110 from which to manipulate the image. After specifying the anchor point, the subject can use the user device (e.g., arrow keys) to adjust the specified line, correcting the perceived distortion caused by their damaged macula. This procedure may be performed on each eye independently, providing a set of two modified grids.

Figures 31E, 31F:
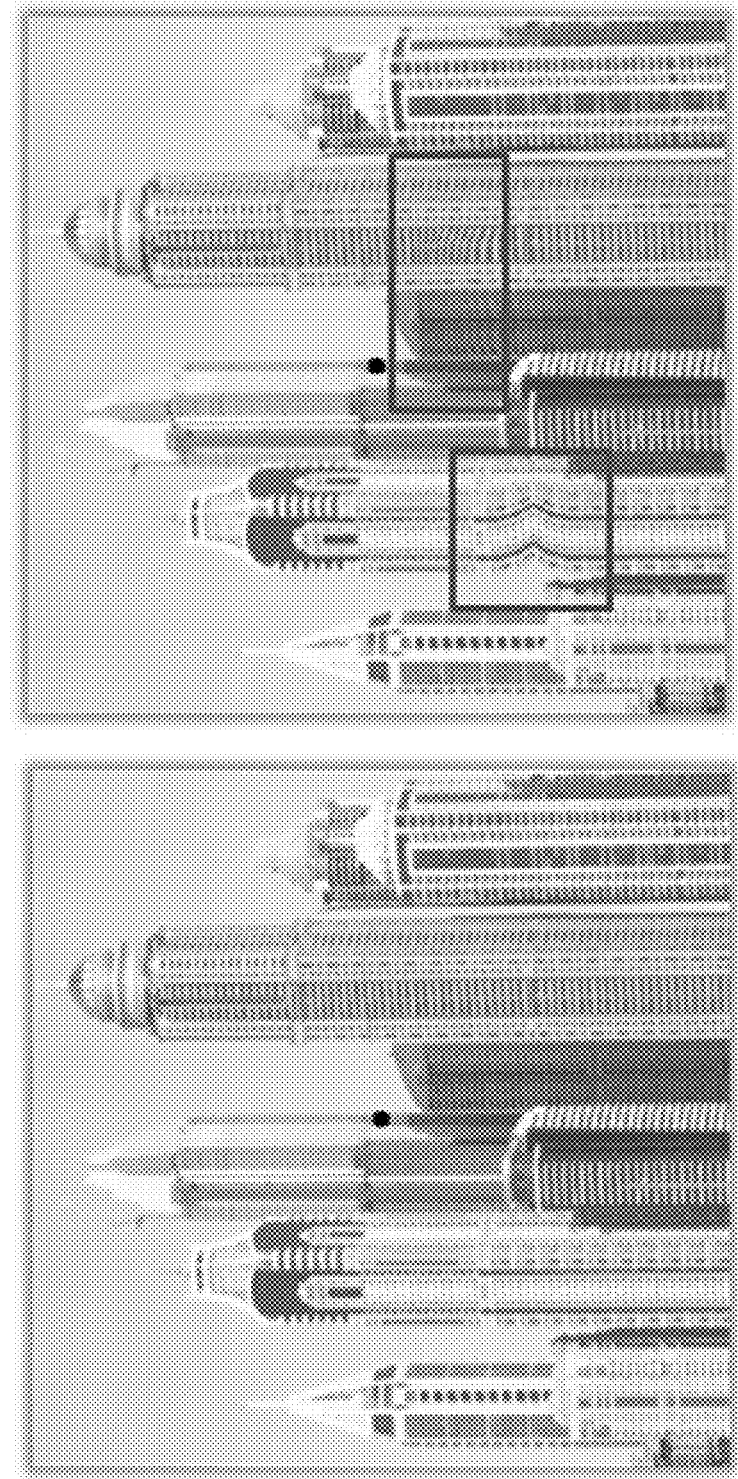
FIG. 31E illustrates a scene as it should be perceived by the subject according to various embodiments described herein.
FIG. 31F illustrates an example corrected visual field that when provided to a subject with a visual distortion determined by the grid technique results in that subject perceiving the visual field as shown FIG. 31E according to various embodiments described herein.

Once the subject completes the modification of the lines to appear straight, a vision correction framework takes the new grids and generate meshes of vertices corresponding to the applied distortions. These meshes, resulting from the testing mode, are applied to an arbitrary image to compensate for the patient's abnormalities. For example, each eye may be shown the modified image corresponding to the appropriate mesh, as part of confirmation of the testing mode. The subject can then indicated on the user device if the corrected images appear faultless which, if true, would indicate that the corrections were successful. For example, FIG. 31E illustrates an actual scene, as it should be perceived by the user. FIG. 31F illustrates a corrected visual field that when provided to a subject with a visual distortion determined by the Amsler grid technique, results in that subject seeing the visual field of FIG. 31F as the actual visual field of FIG. 31E.

Such correction may be performed in real time on live images to present the subject with a continuously corrected visual scene. The correction may be achieved real-time whether the spectacle device includes displays that generate the capture visual field or whether the spectacle device is custom-reality based and uses a correction layer to adjust for the distortion, as both cases may utilize the determined corrective meshes.

Figure 31G:
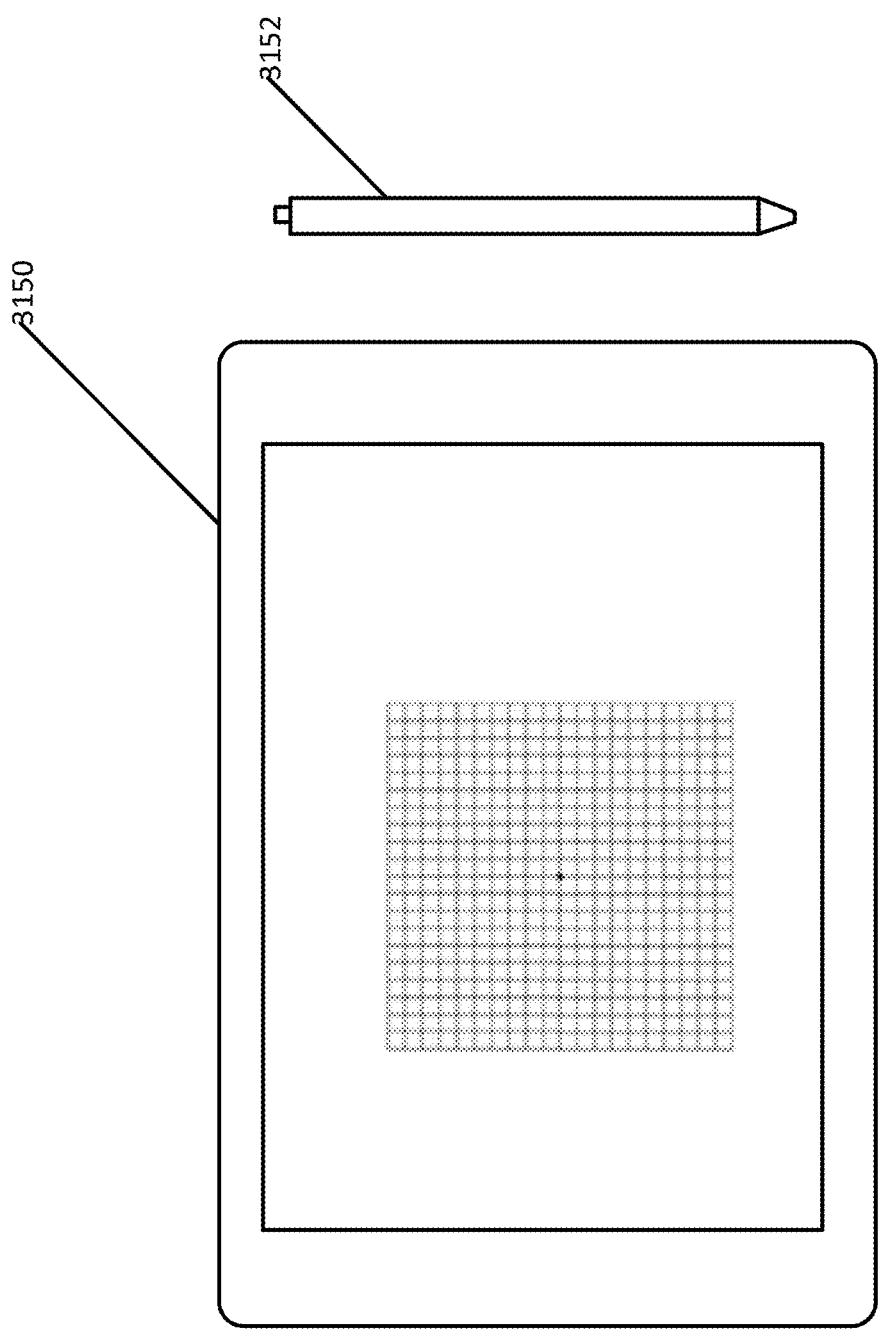
FIG. 31G illustrates a display including a manipulable grid onto which a subject may communicate distortions within a visual field according to various embodiments described herein.

In some examples, a reference image such as the Amsler pattern may be presented directly on a touch screen or tablet PC, such as 3150 (e.g., a tablet PC) shown in FIG. 31G. The Amsler pattern is presented on a display of the device 3150, and the subject may manipulate the lines that appear curved using a stylus 3152 to draw the corrections that are to be applied to the lines to make them appear straight. During the testing mode, after each modification, the grid may be redrawn to reflect the latest edit. This procedure may be performed on each eye independently, providing us a set of two modified grids. After the subject completes the testing mode modification, the tablet PC executes an application that creates and sends the mesh data to an accompanying application on the spectacles device to process images that apply the determined meshes.

Once the spectacles device receives the results of the testing mode modification, the spectacles device may apply them to an arbitrary image to compensate for the subject's abnormalities. The images that result from this correction may then be displayed. The display may be via an VR, AR headset. In one example, the display presents the images to the user via the headset in a holographical way. Each displayed image may correspond to the mesh created for each eye. If the corrected images seem faultless to the patient, the corrections may be considered successful and may be retained for future image processing. In some embodiments, of the testing mode, instead or in addition to presenting a single image modified according to the modified grids, a video incorporating the modifications may be presented. In one example, the video includes a stream of a camera's live video feed through the correction, which is shown to the subject.

The present techniques may be used in any number of applications, including for example for otherwise healthy subjects frequently affected by quick onset of optical pathologies, subjects such as soldiers and veterans. Loss of visual field compromises the ability of soldiers, veterans, other affected patients to perform their essential tasks as well as daily life activities. This visual disability compromises their independence, safety, productivity and quality of life and leads to low self-esteem and depression. Despite recent scientific advances, treatment options to reverse existing damage of the retina, optic nerve or visual cortex are limited. Thus, treatment relies on offering patients with visual aids to maximize their functionality. Current visual aids fall short in achieving those goals. This underlines the need for having better visual aids to improve visual performance, quality of life and safety. The techniques herein, integrated into spectacles device, are able to diagnose and mitigate common quick onset eye injuries, such as military-related eye injuries and diseases, that cause visual field defects, in austere or remote, as well as general, environments. The techniques herein are able to diagnose and quantify visual field defects. Using this data, the devices process, in real-time, patients' field of view and fits and projects corrected images on their remaining functional visual field. Thus, minimizing the negative effect of the blind (or reduced) part of visual field on patients' visual performance. Moreover, the fact that the spectacles device do not rely on another clinical device to diagnose visual field defects make them specifically useful in austere and remote environments. Similarly, the present techniques may be used to augment the visual field of normal subjects to have a better than normal visual field or vision.

The present techniques may correct for the lower and/or high order visual aberration in a dynamic manner. The present techniques may detect the size of the pupil, accommodative status and change in line of sight and process the visual image displayed or projected to the eye of the user using the corresponding visual aberration corrective profile. The higher and/or lower order aberrations may be captured in relation to the pupil size, state of accommodation and direction of gaze using aberrometer to allow the spectacles to create such a dynamic corrective profile. The image projected to the subject by the present techniques may be inversely distorted according to the actual aberrations of the subject so that his/her own aberrations are re-inversed to provide the best vision (see, e.g., FIGS. 31B-31F). The present techniques may detect the state of accommodation by detecting the signs of the near reflex, namely miosis (decrease the size of the pupil) and convergence (inward crossing of the pupil). The pupil tracker may include a pupil tracker to track the pupil and line of sight to detect the direction of gaze. Such inputs, as well as others described herein, may allow the present techniques to detect the correction profile to be displayed.

The present techniques may automatically autofocus the images displayed to provide near vision. To further augment and enhance near vision, the present techniques may use inward directed image sensors such as cameras to detect if the subject is trying to look at a near target by detecting the signs of the near reflex, which are miosis (decrease in pupil size and convergence (inward movement of the eye) and automatically provides better near vision. The present techniques also determine how far the object is by quantifying the amount of the near reflex exerted by the subject and thus provides the adequate correction for that.

The present techniques may correct for double vision secondary eye misalignment in a dynamic manner, meaning that as the present techniques track the pupil of the subject and line of sight or visual axes, it may displace the images in a real-time to provide a continuous compensation for eye misalignment and thus prevent double vision in all gazes.

The present techniques may include software that redistributes the image captured by the DTS vision field cameras to the subject's actual functional visual field. The actual visual field may be dynamically projected in reference to the pupil, line of sight or visual axes.

In patients with age related macular degeneration or other pathology of the human macula, who has central blind spot, the present techniques may be utilized to distribute the image to the peripheral or paracentral part of the functional visual field of a subject. The present techniques may project parts of the image of interest to healthy parts of the retina and avoid the unhealthy parts of the retina.

The present techniques may capture the normal binocular visual field and distribute that to both eyes actual functional visual field to provide the subject with the widest possible field of view.

Anisometropia resulting from unequal refractive power of the subject eyes may be corrected by the present techniques, e.g., through creating images with equal sizes and displaying them or project them to both eyes to avoid visual disturbances.

Unlike Lenses of glass spectacles that cause distortion to the visual field, such as minification or magnification of the image of interest, the present techniques may be utilized as to not affect a visual field of subjects because the visual field of display or the projection may be independent of corrective lenses.

The present techniques may display or project light independent from the brightness of the surrounding environment and can be adjusted automatically according to the size of the pupil as detected by the present techniques or manually as patient requires. The present techniques may detect pupil size and adjust for brightness in a personalized and customized manner. Subjects with anisocoria uses the present techniques to allow adjusting brightness for each eye separately. This also is done automatically by the present techniques as it detects the pupil size.

EXAMPLE

Figure 35A:
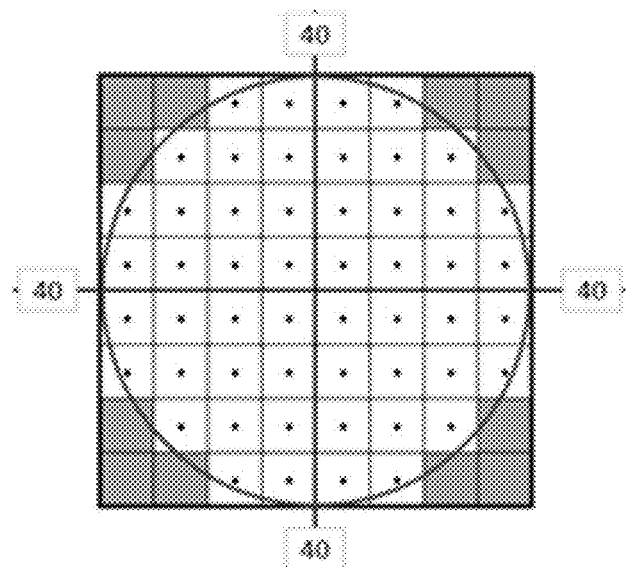
FIG. 35A illustrates a fast thresholding strategy for a testing mode including four contrast staircase stimuli covering a central 40 degree radius using 52 stimuli sequences at predetermined locations according to various embodiments described herein.

An example application of a present techniques in a visual field testing protocol is described. A testing mode applied a fast thresholding strategy utilizing four contrasting staircase stimuli covering the central 40 degrees' radius using 52 stimuli sequences at predetermined locations, as illustrated in FIG. 35A. In other examples, different numbers of contrast stimuli, coverage, and stimuli locations may be used. In this example, the stimuli was located at the center of each cell shown in the FIG. 35A. The twelve corner cells, where the stimuli are not visible because of the circular display's lens, were not tested. The spacing between each stimulus location was approximately 10 degrees apart. Each stimuli sequence contained four consecutive stimuli at different contrast levels with respect to the background. Stimuli contrast ranged between 33 dB down to 24 dB in steps of 3 dB in a descending order between each contrast level. Threshold values were recorded at the last seen stimulus. If the patient did not see any stimulus contrast at a specific location, the location is marked unseen and was given a value of 0 dB.

The background had a bright illumination (100 lux) while the stimuli were dark dots with different contrast degrees. Therefore, the test was a photopic test rather than a mesopic one. In some embodiments, back ground may be dark and stimuli may comprise bright illumination dots. Each stimulus was presented for a time period of approximately 250 msec, followed by a response waiting time period of approximately 300 msec. These time periods were also made adjustable through a control program according to the subject's response speed, which may be adjusted prior to testing based on pre-test demonstration or dynamically during testing, for example. Generally, a stimulus size of 0.44 degrees was used at the central 24 degrees' radius, which is equivalent to the standard Goldmann stimulus size III. The stimulus size at the periphery (between 24 and 40 degrees' radius) was doubled to be 0.88 degrees. The purpose of doubling the stimulus size in the peripheral vision was to overcome the degraded display lens performance at the periphery. This lens degradation effect was significant, as the normal human vision's acuity even deteriorates at the peripheral regions. The testing program also had the ability for the stimulus size to be changed for the different patient cases.

The fixation target (pattern) of FIG. 35A was located in the center of the screen for each eye tested. This target was designed as a multicolor point, rather than a unicolor fixation point as routinely used in the traditional Humphrey tests. This color changing effect helped grab the attention of the subject and made target focusing easier for them. The frequency of the color changes was asynchronous with the stimulus appearance, so that the subject would not relate both events together and falsely responds. The testing protocol also had the ability for the fixation target size to be changed according to the patient's condition. In addition, the eye/pupil tracking system may be used to check the subject's eye fixation at different time intervals. The eye tracking system transmits to the testing program the gaze vectors' direction, which informs the program if the subject is properly focused to the center or not.

Fixation checks were performed using the pupil/gaze data for each eye individually. Pupil/gaze data were acquired at different time instances and if the gaze direction vectors were at approximately 0 degrees then the subject is focusing on the center target, otherwise the program would pause waiting for fixation to restored. If the patient were out of fixation, no stimulus was shown and the test was halted until the participant gets back in fixation. Offset tolerance was allowed for minor eye movements at the fixation target. Fixation checks were performed for each stimuli's location at mainly two time events; before showing each stimulus in the stimuli sequence (i.e. prior to each stimulus contrast level of the four levels mentioned earlier), and before recording a response, whether the response was positive (patient saw the stimulus) or negative (patient did not see the stimulus). Negative responses were recorded at the end of the stimuli sequence interval in addition to the allowed response time. Checking fixation before showing the stimuli sequence was to ensure the patient was focusing on the fixation target. If the subjects were out of fixation, no stimulus was shown and the test was halted until the participant gets back in fixation.

Figure 35B:
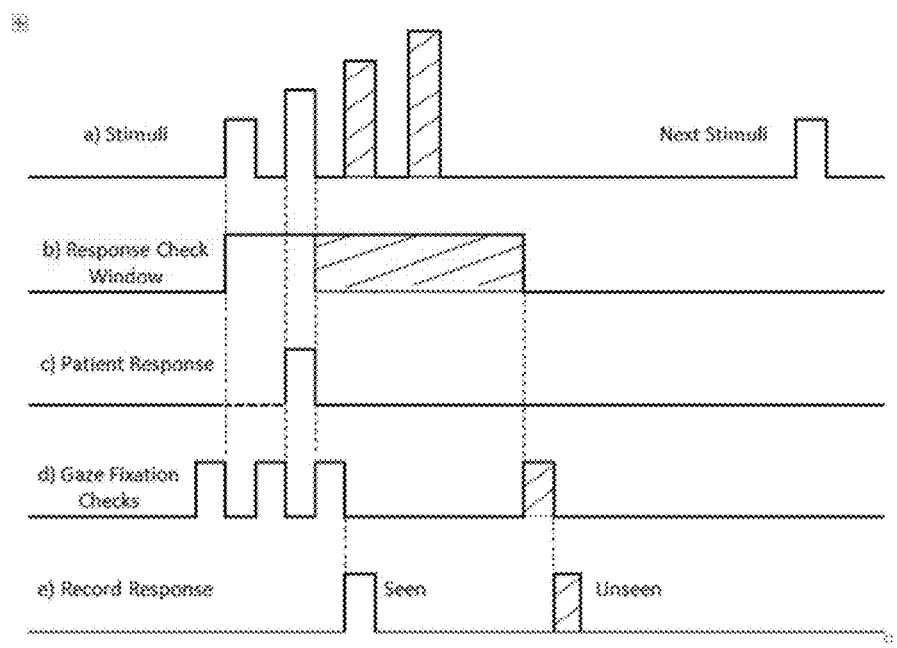
FIG. 35B shows a timing diagram showing five step (a-e) of a testing sequence at one stimulus location according to various embodiments described herein.

FIG. 35B shows a timing diagram showing the five step (a-e) of a testing sequence at one stimulus location.

In one example, a pupil tracking device, which may be separate or a component of a vision system or device thereof, may include inward directed image sensors and be configured to provide data instructing the image display device, e.g., monitor, which may include a projector, to change the location of the stimulus being projected according to line of sight movement. In this way, even if the subject is looking around and not fixating, the stimuli may move with the eyes of the subject and will continue testing the desired location of the visual field. Therefore, rather than halting the stimuli sequence when the subject is determined to be focused outside of the fixation target, the stimuli sequence may continue with a modification of the stimuli to correspond with the intended location within the subject's visual field within the sequences as repositioned based on a determination of the subject's current fixation point.

For each subject, the visual field test started by orienting the subject of how the test goes. The spectacles device was fitted on the patient to ensure that the subject could see the fixation target clearly, and if necessary, target size was adjusted accordingly. Eye tracking calibration was performed at one point, the fixation target. Following that, a demonstration mode was presented to the subject. This mode follows the same sequence as the main test, but with only fewer locations, seven locations in this instance, and without recording any responses. The purpose of this mode was to train the subject on the test. Additionally, this training mode helps the program operator to check for the eye tracking system accuracy, patient response speed, and the patient eye's location with respect to the mounted headset, to make sure that no error or deviation would occur during the full test.

Normal blind spots were then scanned for, by showing suprathreshold stimuli at four different locations spaced by 1 degree in the 15-degree vicinity. This step was beneficial to avoid rotational misfits between the headset and the subject's eyes.

Next, the 52 stimuli sequences were presented to the patient at the pre-specified locations with random order. The subject indicated responses by either actuating an electronic clicker or gesturing in response to a stimuli. After recording the subject's responses at all locations, the "unseen" points' locations were temporarily stored. A search algorithm was then employed to find the locations of all "seen" points on the perimeter of the "unseen" points' locations. Those two sets of points were then retested, to eliminate random response errors by the participant, and ensure continuity of the visual field regions. False positive responses, false negative responses and fixation losses (if any) were calculated and reported by the end of the test. Consequently, all the 52 responses were interpolated using a cubic method to generate a continuous visual field plot of the tested participant.

The visual field test was tried on 20 volunteer subjects using simulated field defects, by covering parts of the inner display lens of the spectacles device. The results were assessed on point by point comparison basis with an image showing the covered areas of the display. The 52 responses were compared at the approximate corresponding locations in the covered headset's display image, as a measure of testing accuracy. Summary of the calculated errors are listed in Table 1.

TABLE 1

Error calculations for the 20 cases simulated defects visual field measurements.

| | Left Eyes | | Right Eyes | | Total Error | |
|---|---|---|---|---|---|---|
| | Mean | SD | Mean | SD | Mean | SD |
| Error Points | 1.600 | 1.698 | 1.500 | 1.396 | 1.550 | 1.535 |
| Error Percentage | 3.137% | 3.329% | 2.941% | 2.736% | 3.039% | 3.009% |

On the other hand, visual field tests for the 23 clinical patients were compared with the most recent Humphrey Field Analyzer (HFA) test routinely made by the subject during their visits. The common 24 degrees central areas were matched and compared between the two field testing devices. The comparison and relative error calculations were based again on a point by point basis at the common central 24 degrees areas, where areas beyond this region were judged through continuity with the central area and lack of isolated response points. Summary of the calculated errors are listed in table 2.

TABLE 2

Error calculations for 23 patients visual field measurements.

| | Left Eyes | | Right Eyes | | Total Error | |
|---|---|---|---|---|---|---|
| | Mean | SD | Mean | SD | Mean | SD |
| Error Points | 3.059 | 2.277 | 3.063 | 2.016 | 3.061 | 2.120 |
| Error Percentage | 7.647% | 5.692% | 7.656% | 5.039% | 7.652% | 5.301% |

An image remapping process was then performed, which involved finding new dimensions and a new center for the displayed images to be shown to the patient. The output image fits in the bright visual field of a subject's eye by resizing and shifting the original input image.

The visual field was binarized by setting all seen patient responses to ones, and keeping the unseen responses to zeros, this resulted in a small binary image of 8×8 size. In other embodiments, smaller or larger binary images sizes may be used. Small regions containing at most 4 connected pixels, were removed from the binary visual field image. The 4 connected pixels represented a predetermined threshold value for determination of small regions, although larger or smaller threshold values may be used in some embodiments. Those small regions were not considered in the image fitting process. The ignored small regions represent either the normal blind spots, insignificant defects, or any random erroneous responses that might have occurred during the subject's visual field test.

Based on this interpolated binary field image, the bright field's region properties were calculated. Calculated properties for the bright regions included: 1) bright areas in units of pixels, 2) regions' bounding box, 3) weighted area centroid, and 4) a list of all pixels constituting the bright regions of the visual field. A bounding box was taken as the smallest rectangle enclosing all pixels constituting the bright region. A region's centroid was calculated as the center of mass of that region calculated in terms of horizontal and vertical coordinates. The values of this property correspond to the output image's new center, which corresponds to an amount of image shift required for mapping.

Figure 36:
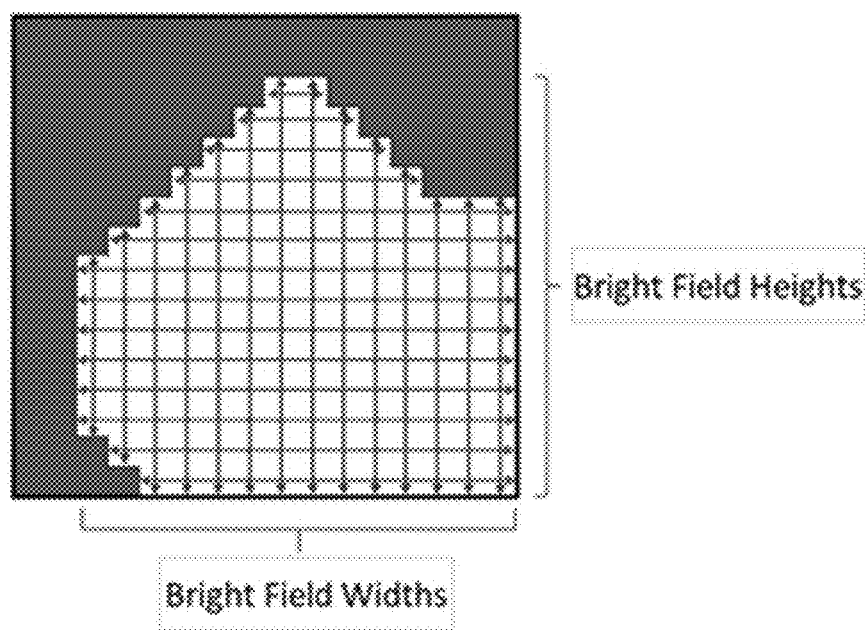
FIG. 36 illustrates calculation of widths and heights of pixels bounding the largest bright field according to various embodiments described herein.
Figure 37:
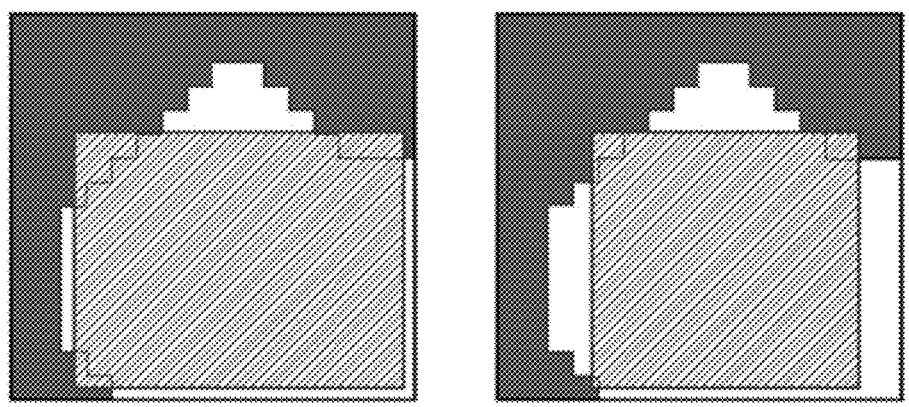
FIG. 37 illustrate a width map and height map according to various embodiments described herein.

Using a list of pixels constituting the largest bright field, the widths and heights of all pixels bounding the bright field were calculated, as shown in FIG. 36. For each row in the bright field, the two bounding pixels were found and their vertical coordinates were subtracted to get the field's width $BF_{width}$ at that specific row. This width calculation was iterated for all rows establishing the considered bright field to calculate $BF_{widths}$. The same iteration process may be applied on a column basis to calculate $BF_{heights}$. Afterwards, either one of two scaling equations may be used to determine the new size of the mapped output image; $Width_{map}$ and $Height_{map}$, as shown in FIG. 37.

The $Width_{map}$ may be calculated using resizing equation:

$$Width_{map1} = median(BF_{widths}),$$

$$Height_{map1} = median(BF_{heights}),$$

where $BF_{widths}$ and $BF_{heights}$ are the calculated bright field's bounding pixels' widths and heights, respectively. This scaling method calculates the new output image size as the median of the bright visual field size in each direction, centered at the new image center, found as above. The median measure was used rather than the mean value, to avoid any resizing skewness related to exceedingly large or small bright field dimensions. The mapping behavior of this method is to fit images within the largest possible bright area, but image stretching or squeezing could occur, as this method does not preserve the aspect ratio.

The $Height_{map}$ may be calculated using resizing equation:

$$Width_{map2} = \frac{\sum BF_{widths}}{Isize^2} \times BX_{Width},$$

$$Height_{map2} = \frac{\sum BF_{heights}}{Isize^2} \times BX_{height},$$

where $I_{size}$ is the interpolated image size (output image size), $BX_{widths}$, $BX_{heights}$ are the bounding box width and height. The summations in the numerators of the equation approximate the bright field area calculated with respect to the horizontal and vertical directions, respectively. Therefore, dividing those summations by the square of the output image's size provided an estimate of the proportional image areas to be mapped in each direction. These proportions are then multiplied by the corresponding bounding box dimension that was previously calculated. The mapping behavior of this method is to fit images in the largest bright visual field while trying to preserve the output image's aspect ratio. Incorporating the bounding box's dimensions into the calculations helped this effect to happen. Yet, preservation of the aspect ratio may not result in all defective visual field patterns.

In one embodiment, the AI system may utilized the two equations and tens if not hundreds of the difference equations in a process of optimization to see which one will allow fitting more of the seeing visual field with the image. Based on the feedback of the operators the system may learn to prefer an equation more than the others based on the specific visual field to be corrected.

Figure 38:
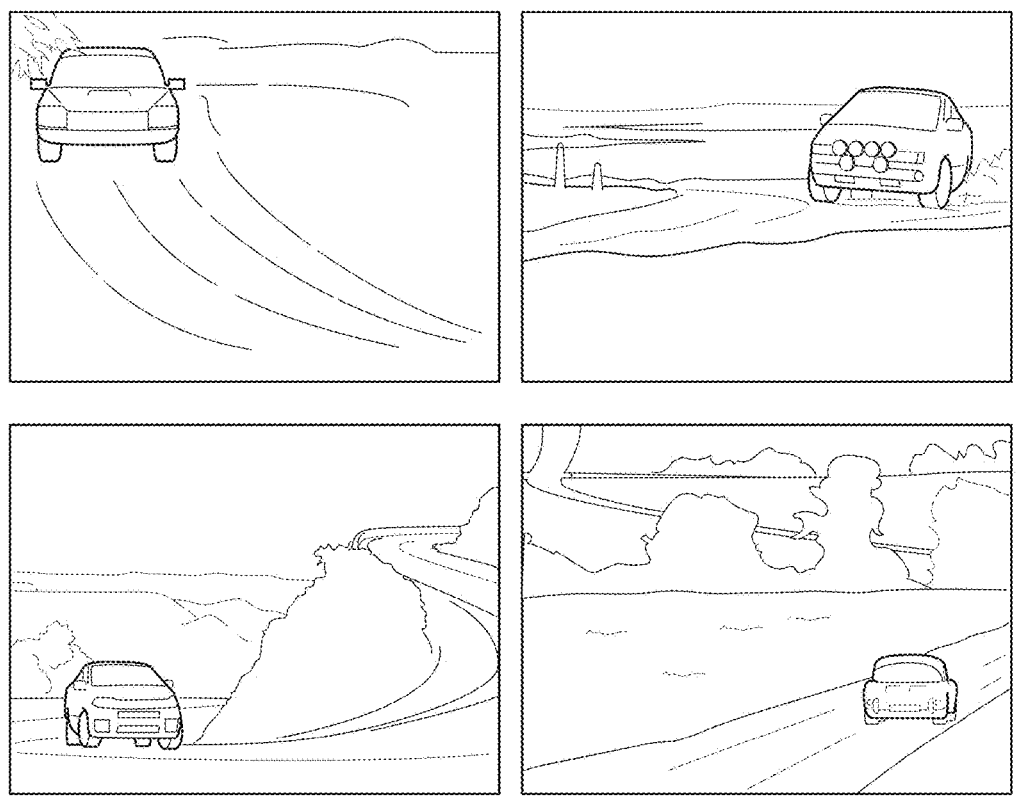
FIG. 38 illustrate test images used to test four main quadrants of a visual field according to various embodiments described herein.
Figure 39A:
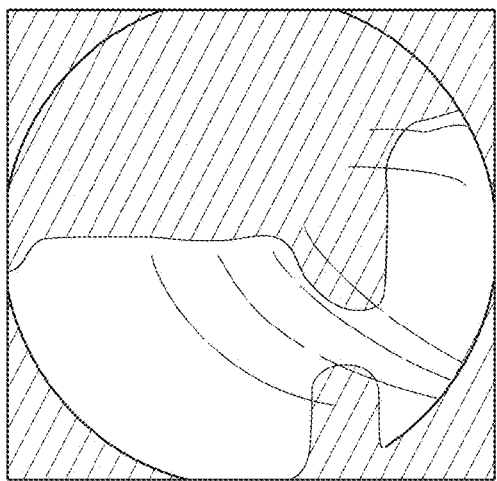
FIG. 39A illustrates an example visual field view prior to remapping according various embodiments described herein.
Figure 39B:
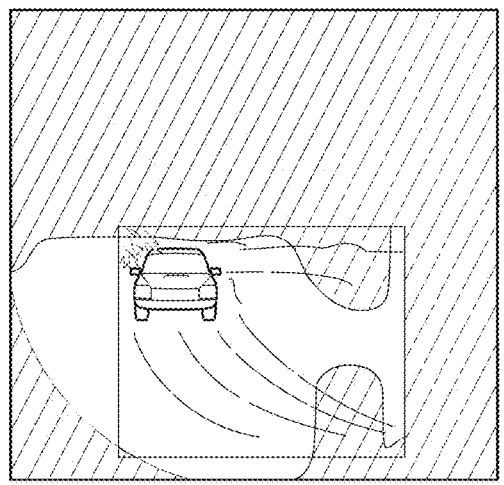
FIG. 39B illustrates an example visual field view following remapping according to various embodiments described herein.

These remapping techniques were used in an identifying hazardous objects test. The remapping methods were tested on 23 subjects using test images that included a safety hazard, a vehicle in this test. The test images were chosen to test the four main quadrants of the visual field, as shown in FIG. 38. A visual field example was used to remap the test images for display to the subject. The subject was tested by showing an image of an incoming car. The subject could not see the car before being shown the remapped image, as shown in FIG. 39A illustrating the image as seen by the subject without remapping and in FIG. 39B illustrating the image as seen after remapping. Our preliminary study demonstrated that 78% subjects (18 out of 23) were able to identify safety hazards that they could not do without our aid. Some subjects were tested on both eyes individually, so 33 eye tests were available. It was found that in 23 out of 33 eyes the visual aid was effective in helping the subject identify the simulated incoming hazard (P=0.023).

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information. In some embodiments, memory or computer readable storage medium of memory stores programs, modules and data structures, or a subset thereof for a processor to control and run the various systems and methods disclosed herein. In one embodiment, a non-transitory computer readable storage medium having stored thereon computer-executable instructions which, when executed by a processor, perform one or more of the methods disclosed herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible.

What is claimed:

1. A system for facilitating increased field of view of a scene via a wearable device, the system comprising:
   a computer system that comprises one or more processors executing computer program instructions that, when executed, cause the computer system to:
   obtain, via a wearable device, a plurality of images of a scene, the wearable device comprising one or more monitors to display one or more images to an eye of a user;
   determine a central region common to the plurality of images;
   for each image of the plurality of images, determine a peripheral region of the image divergent from a corresponding peripheral region of at least another image of the plurality of images;
   generate a combined image based on the common central region and the divergent peripheral regions such that the combined image comprises (i) a first region comprising a representation of the common central region and (ii) a second region comprising representations of the divergent peripheral regions, the second region being around the first region; and
   cause the combined image to be displayed on the one or more monitors of the wearable device.

2. The system of claim 1, wherein the computer system is caused to:
   perform shifting of each image of the plurality of images such that a size of the common central region is decreased and a size of at least one of the divergent peripheral regions is increased,
   wherein generating the combined image comprises generating the combined image based on the common central region and the divergent peripheral regions subsequent to the performance of the shifting.

3. The system of claim 1, wherein the computer system is caused to:
   perform resizing of one or more regions of the plurality of images such that an extent of any resizing of the common central region is different than an extent of any resizing of at least one of the divergent peripheral regions,
   wherein generating the combined image comprises generating the combined image based on the common central region and the divergent peripheral regions subsequent to the performance of the resizing.

4. The system of claim 3, wherein performing the resizing comprises performing the resizing of one or more regions of the plurality of images such that a percentage change in size of the common central region represented in the first region of the combined image is greater than or less than a percentage change in size of at least one of the divergent peripheral regions represented in the second region of the combined image.

5. The system of claim 4, wherein the percentage change in size of at least one of the divergent peripheral regions is zero, and wherein the percentage change in size of the common central region is greater than zero.

6. The system of claim 4, wherein the percentage change in size of at least one of the divergent peripheral regions is greater than zero, and wherein the percentage change in size of the common central region is zero.

7. The system of claim 1, wherein generating the combined image comprises generating the combined image based on the common central region, the divergent peripheral regions, and a peripheral region common to the plurality of images such that (i) the first region of the combined image comprises the representation of the common central region and a representation of the common peripheral region and (ii) the second region of the combined image comprises representations of the divergent peripheral regions.

8. The system of claim 1, wherein the wearable device comprises first and second cameras, and wherein obtaining the plurality of images comprises obtaining at least one of the plurality of images via the first camera of the wearable device and obtaining at least another one of the plurality of images via the second camera of the wearable device.

9. The system of claim 1, wherein the one or more monitors of the wearable device comprises first and second monitors, and wherein causing the combined image to be displayed comprises causing the combined image to be displayed via the first and second monitors.

10. The system of claim 1, wherein the computer system is a wearable computer system comprising the one or more processors executing the computer program instructions that, when executed, cause the wearable computer system to perform all the foregoing operations.

11. The system of claim 1, wherein the wearable device comprises a wearable spectacles device.

12. The system of claim 11, wherein the wearable spectacles device comprises the one or more processors executing the computer program instructions that, when executed, cause the wearable spectacles device to perform all the foregoing operations.

13. A method being implemented by one or more processors executing computer program instructions that, when executed, perform the method, the method comprising:
obtaining, via a wearable device, a plurality of images of a scene;
determining a central region common to the plurality of images;
for each image of the plurality of images, determining a peripheral region of the image divergent from a corresponding peripheral region of at least another image of the plurality of images;
generating an enhanced image based on the common central region and the divergent peripheral regions such that the enhanced image comprises (i) a first region comprising a representation of the common central region and (ii) a second region comprising representations of the divergent peripheral regions, the second region being around the first region; and
causing the enhanced image to be displayed via the wearable device.

14. The method of claim 13, further comprising:
performing shifting of each image of the plurality of images such that a size of the common central region is decreased and a size of at least one of the divergent peripheral regions is increased,
wherein generating the enhanced image comprises generating the enhanced image based on the common central region and the divergent peripheral regions subsequent to the performance of the shifting.

15. The method of claim 13, further comprising:
performing resizing of one or more regions of the plurality of images such that an extent of any resizing of the common central region is different than an extent of any resizing of at least one of the divergent peripheral regions,
wherein generating the enhanced image comprises generating the enhanced image based on the common central region and the divergent peripheral regions subsequent to the performance of the resizing.

16. The method of claim 15, wherein performing the resizing comprises performing the resizing of one or more regions of the plurality of images such that a percentage change in size of the common central region represented in the first region of the enhanced image is greater than or less than a percentage change in size of at least one of the divergent peripheral regions represented in the second region of the enhanced image.

17. The method of claim 16, wherein the percentage change in size of at least one of the divergent peripheral regions is zero, and wherein the percentage change in size of the common central region is greater than zero.

18. The method of claim 16, wherein the percentage change in size of at least one of the divergent peripheral regions is greater than zero, and wherein the percentage change in size of the common central region is zero.

19. The method of claim 13, wherein generating the enhanced image comprises generating the enhanced image based on the common central region, the divergent peripheral regions, and a peripheral region common to the plurality of images such that (i) the first region of the enhanced image comprises the representation of the common central region and a representation of the common peripheral region and (ii) the second region of the enhanced image comprises representations of the divergent peripheral regions.

20. The method of claim 13, wherein the wearable device comprises first and second cameras, and wherein obtaining the plurality of images comprises obtaining at least one of the plurality of images via the first camera of the wearable device and obtaining at least another one of the plurality of images via the second camera of the wearable device.

21. The method of claim 13, wherein causing the enhanced image to be displayed comprises causing the enhanced image to be displayed via first and second monitors of the wearable device.

22. The method of claim 13, wherein a wearable computer system comprising the one or more processors executing the computer program instructions that, when executed, perform the method.

23. The method of claim 13, wherein the wearable device comprises a wearable spectacles device.

24. One or more non-transitory computer-readable media comprising instructions that, when executed by one or more processors, cause operations comprising:
obtaining, via a wearable device, a plurality of images of a scene;
determining a central region common to the plurality of images;
for each image of the plurality of images, determining a peripheral region of the image divergent from a corresponding peripheral region of at least another image of the plurality of images;
generating an enhanced image based on the common central region and the divergent peripheral regions such that the enhanced image comprises (i) a first region comprising a representation of the common central region and (ii) a second region comprising representations of the divergent peripheral regions, the second region being around the first region; and
causing the enhanced image to be displayed via the wearable device.

25. The one or more non-transitory computer-readable media of claim 24, wherein the operations further comprise:
performing shifting of each image of the plurality of images such that a size of the common central region is decreased and a size of at least one of the divergent peripheral regions is increased,
wherein generating the enhanced image comprises generating the enhanced image based on the common central region and the divergent peripheral regions subsequent to the performance of the shifting.

26. The one or more non-transitory computer-readable media of claim 24, wherein the operations further comprise:

performing resizing of one or more regions of the plurality of images such that an extent of any resizing of the common central region is different than an extent of any resizing of at least one of the divergent peripheral regions, wherein generating the enhanced image comprises generating the enhanced image based on the common central region and the divergent peripheral regions subsequent to the performance of the resizing.

27. The one or more non-transitory computer-readable media of claim 26, wherein performing the resizing comprises performing the resizing of one or more regions of the plurality of images such that a percentage change in size of the common central region represented in the first region of the enhanced image is greater than or less than a percentage change in size of at least one of the divergent peripheral regions represented in the second region of the enhanced image.

28. The one or more non-transitory computer-readable media of claim 27, wherein the percentage change in size of at least one of the divergent peripheral regions is zero, and wherein the percentage change in size of the common central region is greater than zero.

29. The one or more non-transitory computer-readable media of claim 27, wherein the percentage change in size of at least one of the divergent peripheral regions is greater than zero, and wherein the percentage change in size of the common central region is zero.

30. The one or more non-transitory computer-readable media of claim 24, wherein generating the enhanced image comprises generating the enhanced image based on the common central region, the divergent peripheral regions, and a peripheral region common to the plurality of images such that (i) the first region of the enhanced image comprises the representation of the common central region and a representation of the common peripheral region and (ii) the second region of the enhanced image comprises representations of the divergent peripheral regions.

* * * * *